United States Patent
Gromada et al.

(10) Patent No.: US 11,834,500 B2
(45) Date of Patent: Dec. 5, 2023

(54) BISPECIFIC ANTIGEN BINDING MOLECULES THAT BIND LEPTIN RECEPTOR AND/OR GP130, AND METHODS OF USE THEREOF

(71) Applicant: Regeneron Pharmaceuticals, Inc., Tarrytown, NY (US)

(72) Inventors: Jesper Gromada, Scarsdale, NY (US); Panayiotis Stevis, West Orange, NJ (US); Judith Altarejos, Chappaqua, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 451 days.

(21) Appl. No.: 16/222,800

(22) Filed: Dec. 17, 2018

(65) Prior Publication Data
US 2019/0185562 A1     Jun. 20, 2019

Related U.S. Application Data

(60) Provisional application No. 62/635,406, filed on Feb. 26, 2018, provisional application No. 62/607,137, filed on Dec. 18, 2017.

(51) Int. Cl.
| | |
|---|---|
| C07K 16/28 | (2006.01) |
| C07K 16/46 | (2006.01) |
| A61K 45/06 | (2006.01) |
| A61P 5/04 | (2006.01) |
| A61K 39/395 | (2006.01) |
| A61P 3/10 | (2006.01) |
| A61P 3/04 | (2006.01) |
| A61K 39/00 | (2006.01) |

(52) U.S. Cl.
CPC ...... *C07K 16/2803* (2013.01); *A61K 39/3955* (2013.01); *A61K 45/06* (2013.01); *A61P 3/04* (2018.01); *A61P 3/10* (2018.01); *A61P 5/04* (2018.01); *C07K 16/2866* (2013.01); *C07K 16/2869* (2013.01); *C07K 16/468* (2013.01); *A61K 2039/505* (2013.01); *A61K 2039/54* (2013.01); *C07K 2317/21* (2013.01); *C07K 2317/31* (2013.01); *C07K 2317/33* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,717,073 | A | 2/1998 | Wijdenes et al. |
| 6,005,080 | A | 12/1999 | Snodgrass et al. |
| 6,380,363 | B1 | 4/2002 | Tartaglia et al. |
| 6,977,240 | B1 | 12/2005 | Tartaglia et al. |
| 7,067,472 | B1 | 6/2006 | Feng et al. |
| 7,067,477 | B2 | 6/2006 | MacLeod |
| 7,521,048 | B2 | 4/2009 | Gliniak et al. |
| 7,524,937 | B2 | 4/2009 | Carter et al. |
| 7,575,878 | B2 | 8/2009 | Tavernier et al. |
| 7,863,240 | B2 | 1/2011 | Ilan et al. |
| 8,697,396 | B2 | 4/2014 | Dall'Acqua et al. |
| 8,969,291 | B2 | 3/2015 | Ilan et al. |
| 9,221,902 | B2 | 12/2015 | Smider et al. |
| 9,332,742 | B2 | 5/2016 | McWhirter et al. |
| 9,334,331 | B2 | 5/2016 | Igawa et al. |
| 10,023,644 | B2 | 7/2018 | Gromada et al. |
| 10,253,102 | B2 | 4/2019 | Gromada et al. |
| 10,421,807 | B2 | 9/2019 | Gonzales et al. |
| 10,550,192 | B2 | 2/2020 | Gromada et al. |
| 10,618,968 | B2 | 4/2020 | Gromada et al. |
| 2002/0182676 | A1 | 12/2002 | Tartaglia et al. |
| 2004/0253242 | A1 | 12/2004 | Bowdish et al. |
| 2006/0068429 | A1 | 3/2006 | Bailleul et al. |
| 2007/0280945 | A1 | 12/2007 | Stevens et al. |

(Continued)

FOREIGN PATENT DOCUMENTS

| | | |
|---|---|---|
| AU | 2004201496 C1 | 8/2018 |
| EP | 981365 B1 | 12/2004 |

(Continued)

OTHER PUBLICATIONS

Paul (1993) Fundamental Immunology, #rd edition, pp. 292-295.*

(Continued)

*Primary Examiner* — Michael D Pak
(74) *Attorney, Agent, or Firm* — FisherBroyles, LLP; Cara L. Crowley-Weber; Thomas Triolo

(57) ABSTRACT

The present invention relates to antigen-binding molecules, including bispecific antigen-binding molecules that bind human GP130 and/or human leptin receptor (LEPR), and the use of such antigen-binding molecules for the treatment of conditions and disorders related to leptin deficiency or leptin resistance. The bispecific antigen-binding molecules of the present invention can be, e.g., bispecific antibodies comprising a first antigen-binding domain that specifically binds human GP130 and a second antigen-binding domain that specifically binds human LEPR. The bispecific antigen-binding molecules of the present invention are useful in therapeutic applications where induced leptin and/or LEPR-mediated signaling would be beneficial, e.g., in the treatment of obesity, lipodystrophies and other diseases and disorders associated with or caused by leptin deficiency or leptin resistance.

9 Claims, 1 Drawing Sheet

Specification includes a Sequence Listing.

(56) References Cited

U.S. PATENT DOCUMENTS

| | | |
|---|---|---|
| 2011/0092417 A1 | 4/2011 | Artymiuk et al. |
| 2012/0258073 A1 | 10/2012 | Gerdes et al. |
| 2014/0134162 A1 | 5/2014 | Stavenhagen et al. |
| 2014/0171623 A1 | 6/2014 | Dall'Acqua et al. |
| 2014/0243504 A1 | 8/2014 | Davis et al. |
| 2017/0101477 A1 | 4/2017 | Gromada et al. |
| 2018/0037648 A1 | 2/2018 | Ilan et al. |
| 2018/0127508 A1 | 5/2018 | Gromada et al. |
| 2019/0002569 A1 | 1/2019 | Belaid-Choucair et al. |
| 2019/0185562 A1 | 6/2019 | Gromada et al. |
| 2020/0031946 A1 | 1/2020 | Gromada et al. |

FOREIGN PATENT DOCUMENTS

| | | |
|---|---|---|
| EP | 0730606 B1 | 5/2005 |
| EP | 885299 B1 | 10/2005 |
| EP | 1619250 B1 | 11/2009 |
| EP | 1019432 B1 | 1/2012 |
| JP | 1991-219894 | 9/1991 |
| JP | 1991219894 | 9/1991 |
| WO | WO 1996/08510 | 3/1996 |
| WO | WO 1997/019952 | 6/1997 |
| WO | WO 1997/025425 | 7/1997 |
| WO | WO 1997/26272 | 7/1997 |
| WO | WO 1997/26370 | 7/1997 |
| WO | WO 1997/26523 | 7/1997 |
| WO | WO 1997/27286 | 7/1997 |
| WO | WO 1997/41263 | 11/1997 |
| WO | WO 1998/22128 A1 | 5/1998 |
| WO | WO 1998/48831 | 11/1998 |
| WO | WO 2005/049655 | 6/2005 |
| WO | WO 2006/053883 | 5/2006 |
| WO | WO 2014/043361 A1 | 3/2014 |
| WO | WO 2015/124588 | 8/2015 |
| WO | WO 2017/066204 | 4/2017 |

OTHER PUBLICATIONS

Bendig (1995) Methods: a companion. Methods in Enzymology 8: 83-93.*

MacCallum et al. (1996) J. Mol. Biol. 262: 732-745.*

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*

Skolnick and Fetrow. From genes to protein structure and function: novel applications of computational approaches in the genomic era. Trends in Biotechnology, 2000. vol. 18, pp. 34-39.*

Wu, Nie, Huse, and Watkins. Humanization of a murine monoclonal antibody by simultaneous optimization of framework and CDR residues. Journal of Molecular Biology, 1999. vol. 294, pp. 151-162.*

Bahrenberg et al., (2002) "Identification of the Critical Sequence Elements in the Cytoplasmic Domain of Leptin Receptor Isoforms Required for Janus Kinase/Signal Transducer and Activator of Transcription Activation by Receptor Heterodimers", Molecular Endocrinology, 16(4):859-872.

Barr et al. (1999) "Subcellular Localization and Internalization of the Four Human Leptin Receptor Isoforms", J Biol Chem, 274(30):21416-21424.

Barsh & Schwartz (2002) "Genetic Approaches to Studying Energy Balance: Perception and Integration" Nat Rev Genet, 3(8):589-600.

Bates et al. (2003) "STAT3 Signaling is Required for Leptin Regulation of Energy Balance but not Reproduction", Nature 421: 856-859.

Bates & Myers (2003) "The Role of Leptin Receptor Signaling in Feeding and Neuroendocrine Function", Trends in Endocrinology and Metabolism, 14(10):447-452.

Bjornholm et al., (2007) "Mice Lacking Inhibitory Leptin Receptor Signals are Lean with Normal Endocrine Function", J. Clin. Invest., 117:1354-1360.

Ceddia (2005) "Direct Metabolic Regulation in Skeletal Muscle and Fat Tissue by Leptin: Implications for Glucose and Fatty Acids Homeostasis", Int J Obes, 29(10):1175-83.

Chen et al. (1996) "Evidence That the Diabetes Gene Encodes the Leptin Receptor: Identification of a Mutation in the Leptin Receptor Gene in db/db Mice", Cell, 84(3):491-5.

Clément et al. (1998) "A Mutation in the Human Leptin Receptor Gene Causes Obesity and Pituitary Dysfunction", Nature, 392(6674):398-401.

Cohen et al. (2001) "Selective Deletion of Leptin Receptor in Neurons Leads to Obesity", J. Clin. Invest., 108:1113-1121.

Coppari & Bjørbæk (2012) "The Potential of Leptin for Treating Diabetes and Its Mechanism of Action", Nat Rev Drug Discov., 11(9): 692-708.

Dewall et al. (2008) "Collective and Individual Functions of Leptin Receptor Modulated Neurons Controlling Metabolism and Ingestion", Endocrinology, 149(4):1773-1785.

Heymsfield et al. (1999) "Recombinant Leptin for Weight Loss in Obese and Lean Adults" JAMA, 282(16):1568-1575.

Hukshorn et al. (2003) "Pegylated Human Recombinant Leptin (PEG-OB) Causes Additional Weight Loss in Severely Energy-Restricted, Overweight Men", Am J Clin Nutr, 77:771-776.

Janoschek et al., (2006) "gp130 Signaling in Proopiomelanocortin Neurons Mediates the Acute Anorectic Response to Centrally Applied Ciliary Neurotrophic Factor", PNAS, 103(28):10707-10712.

Kawahara et al., (2003) "Bypassing Antibiotic Selection: Positive Screening of Genetically Modified Cells with an Antigen-Dependent Proliferation Switch", Nucleic Acids Research, 31(No. 7 e32).

Lambert et al. (2001) "Ciliary Neurotrophic Factor Activates Leptin-like Pathways and Reduces Body Fat, Without Cachexia or Rebound Weight Gain, Even in Leptin-Resistant Obesity", PNAS, 98(8): 4652-4657.

Marsh et al., (1999) "Response of Melanocortin-4 Receptor-Deficient Mice to Anorectic and Orexigenic Peptides", Nature Genetics, 21: 119-122.

Marsh et al., (1999) "Effects of Neuropeptide Y Deficiency on Hypothalamic Agouti-Related Protein Expression and Responsiveness to Melanocortin Analogues", Brain Research 848:66-77.

Mori et al., (2004) "Socs3 Deficiency in the Brain Elevates Leptin Sensitivity and Confers Resistance to Diet-Induced Obesity", Nature Medicine, 10(7): 739-743.

Morris & Rui (2009) "Recent Advances in Understanding Leptin Signaling and Leptin Resistance", Am J Physiol Endocrinol Metab., 297(6):E1247-59.

O'Sullivan et al. (2007) "Cytokine Receptor Signaling Through the Jak-Stat-Socs Pathway in Disease", Mol Immunol, 44(10):2497-506.

Powell et al. (2011) "New Drug Targets for the Treatment of Obesity", Clin Pharmacol Ther., 90(1):40-51.

Ravussin et al., (2009) "Enhanced Weight Loss with Pramlintide/Metreleptin: An Integrated Neurohormonal Approach to Obesity", Pharmacotherapy Obesity, 17(9):1736-1743.

Shetty et al. (2011) "Leptin Administration to Overweight and Obese Subjects for Six Months Increases Free Leptin Concentrations but Does not Alter Circulating Hormones of the Thyroid and IGF Axes During Weight Loss Induced by a Mild Hypocaloric Diet", Eur J Endocrinol, 165(2):249-254.

Stefater et al. (2012) "The Anorectic Effect of CNTF Does Not Require Action in Leptin-Responsive Neurons", Endocrinology, 153(6):2647-54.

Suthaus et al. (2010) "Forced Homo- and Heterodimerization of all gp130-type Receptor Complexes Leads to Constitutive Ligand-Independent Signaling and Cytokine-Independent Growth", Mol Biol Cell, 1(15):2797-807.

Wauman & Tavernier (2011) "Leptin Receptor Signaling: Pathways to Leptin Resistance", Frontiers in Bioscience 16:2771-2793.

Zabeau et al. (2003) "The Ins and Outs of Leptin Receptor Activation", FEBS Letters, 546:45-50.

Accession No. NP_002175.2.

Accession No. NP_002294.2.

Accession No. XP_005543194.1.

(56) References Cited

OTHER PUBLICATIONS

Ahmann, et al. (2015) "Efficacy and safety of liraglutide versus placebo added to basal insulin analogues (with or without metformin) in patients with type 2 diabetes: a randomized, placebo-controlled trial," Diabetes, Obesity and Metabolism 17(11):1056-1064.
Al-Lazikani et al. (1997) "Standard Conformations for the Canonical Structures of Immunoglobulins", J. Mol. Biol., 273:927-948.
Allison, et al. (2014) "Connecting leptin signaling to biological function", Journal of Endocrinology, 223:T25-T35.
Altschul et al. (1990) "Basic Local Alignment Search Tool", J. Mol. Biol., 215:403-410.
Altschul et al. (1997) "Grapped BLAST and PSI-BLAST: a new generation of protein database search programs", Nucleic Acids Res., 25:3389-3402.
Bhaskar et al. (2016) "An Allosteric Antibody to the Leptin Receptor Reduces Body Weight and Reverses the Diabetic Phenotype in the Lep ob/Lep ob Mouse", Obesity, 24(8):1687-1694.
Boersma and Pluckthun (2011) "DARPins and other repeat protein scaffolds: advances in engineering and applications", Curr. Opin. Biotechnol., 22:849-857.
Bray and Wadden (2015) "Improving Long-Term Weight Loss Maintenance: Can We Do It?," Obesity, 23:2-3.
Carpenter et al. (1998) "Enhancing leptin response by preventing SH2-containing phosphate 2 interaction with Ob receptor", Proc. Natl. Acad. Sci. USA, 95:6061-6066.
Carpenter, et al. (2012) "Structure of the Human Obesity Receptor Leptin-Binding Domain Reveals the Mechanism of Leptin Antagonism by a Monoclonal Antibody", Structure 20:487-497.
Cron et al. (2016) "The role of gp130 receptor cytokines in the regulation of metabolic homeostasis", Journal of Experimental Biology, 219(2):259-265.
Deddish et al. (1990) "Carboxypeptidase M in Madin-Darby Canine Kidney Cells", J. Biological Chemistry, 265(25):15083-15089.
Ehring (1999) "Hydrogen Exchange / Electrospray Ionization Mass Spectrometry Studies of Structural Features of Proteins and Protein/Protein Interactions", Analytical Biochemistry, 267(2):252-259.
Engen and Smith (2001) "The Basics of Ion Chromatography", Anal. Chem., 73:256A-265A.
Farooqi, et al. (2007) "Clinical and Molecular Genetic Spectrum of Congenital Deficiency of the Leptin Receptor", N. Engl. J. Med., 356:237-247.
Farooqui, et al. (2002) "Beneficial effects of leptin on obesity, T cell hyporesponsiveness, and neuroendocrine/metabolic dysfunction of human congenital leptin deficiency", The Journal of Clinical Investigation, 110(8):1093-1103.
Fazeli, et al. (2006) "Identification of a monoclonal antibody against the leptin receptor that acts as an antagonist and blocks human monocyte and T cell activation", Journal of Immunological Methods, 312:190-200.
Febbraio (2007) "gp130 receptor ligands as potential therapeutic targets for obesity", Journal of Clinical Investigation, 117(4):841-849.
Friedman, et al. (2014) "20 Years of Leptin: Leptin at 20: an overview", J Endocrinol., 223(1):T1-T8.
Gonnet, et al. (1992) "Exhaustive Matching of the Entire Protein Sequence Database", Science, 256: 1443-1445.
Goodson J.M. (1984) "Dental Applications" in: Medical Applications of Controlled Release, vol. 2, Chapter 6, Langer R.S., et al., eds., CRC Press, pp. 115-138.
Halpern, et al. (2010) "Combinations of Drugs in the Treatment of Obesity", Pharmaceuticals, 3:2398-2415.
Haniu, et al. (1998) "Human Leptin Receptor, Determination of Disulfide Structure and N-Glycosylation Sites of the Extracellular Domain*", J Biol Chem, 273(44): 28691-28699.
Hochleitner (2000) "Characterization of a discontinous epitope of the human immunodeficiency virus (HIV) core protein p24 by epitope excision and differential chemical modification followed by mass spectrometric peptide mapping analysis", Protein Science, 9:487-496.
Iepsen, et al. (2014) "Treatment with a GLP-1 receptor agonist diminishes the decrease in free plasma leptin during maintenance of weight loss," International Journal of Obesity, 39(5):834-841.
Junghans, et al. (1990) "Anti-Tac-H, a Humanized Antibody to the Interleukin 2 Receptor with New Features for Immunotherapy in Malignant and Immune Disorders", Cancer Research, 50:1495-1502.
Kazane, et al. (2013) "Self-Assembled Antibody Multimers through Peptide Nucleic Acid Conjugation", Journal of the American Chemical Society, 135(1):340-346.
Klein, et al. (2012) "Progress in overcoming the chain association issue in bispecific heterodimeric IgG antibodies", mAbs, 4(6):653-663.
Kufer, et al. (2004) "A Revival of bispecific antibodies", Trends Biotechnology, 22(5):238-244.
Langer (1990) "New Methods of Drug Delivery", Science, 249:1527-1533.
Mancour, et al. (2012) "Ligand-Induced Architecture of the Leptin Receptor Signaling Complex", Molecular Cell, 48:655-661.
Martin, et al. (1989) "Modeling antibody hypervariable loops: A combined algorithm", Proc. Natl. Acad. Sci. USA, 86:9268-9272.
Mazen, et al. (2011) "Homozygosity for a novel missense mutation in the leptin receptor gene (P316T) in two Egyptian cousins with severe early onset obesity", Molecular Genetics and Metabolism, 102:461-464.
Meehan, et al. (2016) "Metreleptin for injection to treat the complications of leptin eficiency in patients with congenital or acquired generalized lipodystrophy", Clinical Pharmacology, 9(1):59-68.
Molek, et al. (2014) "Screening of synthetic phage display scFv libraries yields competitive ligands of human leptin receptor", Biochemical and Biophysical Research Communications, 452(3):479-483.
Mordenti, et al. (1991) "Interspecies Scaling of Clearance and Volume of Distribution Data for Five Therapeutic Protein", Pharmaceutical Research, 8:1351-1359.
NP_001003679.1 "Leptin receptor isoform 3 precursor [*Homo sapiens*]".
Paz-Filho, et al. (2014) "Leptin treatment: Facts and expectations", Metabolism, pp. 1-11, http://dx.doi.org/10.1016/j.metabol.2014.07.014.
PCT International Search Report and Written Opinion received for PCT/US2016/056465, dated Jan. 10, 2017.
PCT International Search Report and Written Opinion received for PCT/US2018/066075, dated Feb. 25, 2019.
Pearson (1994) "Using the FASTA Program to Search Protein and DNA Sequence Databases", Methods in Molecular Biology, 24:307-331.
Pearson (2000) "Flexible Sequence Similarity Searching with the FASTA3 Program Package", Methods in Molecular Biology, 132: 185-219.
Peelman, et al. (2014) "Insights into signaling assemblies of the leptin receptor", Journal of Endocrinology, 223:T9-T23.
Powell, et al. (1998) "Compendium of Excipients for Parenteral Formulations", PDA J Pharm Sci Technol, 52:238-311.
Procaccini, et al. (2015) "Leptin in autoimmune diseases", Metabolism Clinical and Experimental, 64:92-104.
Rebouissou, et al. (2009) "Frequent In-Frame Somatic Deletions Activate GP130 in Inflammatory Hepatocellular Tumours", Nature Letters 457(8): 200-205.
Reddy, et al. (2000) "Elimination of Fc Receptor-Dependent Effector Functions of a Modified IgG4 Monoclonal Antibody to Human CD4", J. Immunol., 164:1925-1933.
Reineke (2004) "Antibody Epitope Mapping Using Arrays of Synthetic Peptides", Methods Mol Biol, 248:443-463.
Rosenbaum, et al. (2002) "Low Dose Leptin Administration Reverse Effects of Sustained Weight-Reduction on Energy Expenditure and Circulating Concentrations of Thyroid Hormones", The Journal of Clinical Endocrinology & Metabolism, 87(5):2391-2394.
Rosenbaum, et al. (2005) "Low-dose leptin reverses skeletal muscle, autonomic, and neuroendocrine adaptations to maintenance of reduced weight", The Journal of Clinical Investigation, 115(12):3579-3586.
Sefton (1987) "Implantable Pumps", CRC Critical Reviews in Biomedical Engineering, 14(3):201-240.

(56) References Cited

OTHER PUBLICATIONS

Shields et al. (2002) "Lack of Fucose on Human IgG1 N-Linked Oligosaccharide Improves Binding to Human FcγRIII and Antibody-dependent Cellular Toxicity", JBC, 277:26733-26740.
Shimomura, et al. (1999) "Leptin reverses insulin resistance and diabetes mellitus in mice with congenital lipodystrophy", Nature, 401:73-76.
Taga et al. (1997) "Gp130 and the interleukin-6 family of cytokines", Annu. Rev. Immunol, 15:797-819.
Tartaglia et al., (1995) "Identification and Expression Cloning of a Leptin Receptor, OB-R", Cell, 83(7):1263-1271.
Tartaglia (1997) "The Leptin Receptor*", J. Biol Chem, 272(10):6093-6096.
Taylor et al. (1992) "A transgenic mouse that expresses a diversity of human sequence heavy and light chain immunoglobulins", Nucl. Acids Res., 20:6287-6295.
Tutt, et al. (1991) "Trispecific F(ab')3 Derivatives That use Cooperative Signaling Via the TCR/CD3 Complex and CD2 to Activate and Redirect Resting Cytotoxic T Cells", The Journal of Immunology, 147(1):60-69.
Ussar, et al. (2011) "Receptor Antibodies as Novel Therapeutics for Diabetes", Science Translational Medicine, 3(113):22-24.
Wu, et al. (1987) "Receptor-mediated in Vitro Gene Transformation by a Soluble DNA Carrier System", The Journal of Biological Chemistry, 262(10):4429-4432.
Zabeau, et al. (2015) "Leptin: From structural insights to the design of antagonists", Life Sciences, 140:49-56.
Zhao et al. (2014) "Leptin and IL-6 Family Cytokines Synergize to Stimulate Müller Glia Reprogramming and Retina Regeneration", Cell Reports, 9(1):272-284.
Al Qaraghuli, et al. (2020) "Antibody-Protein Binding and Conformational Changes: Identifying Allosteric Signaling Pathways to Engineer a Better Effector Response", Nature Scientific Reports, 10:13969.
Chagnon et al. (2000) "Associations Between the Leptin Receptor Gene and Adiposity in Middle-Aged Caucasian Males from the Heritage Family Study", Journal of Clinical Endocrinology & Metabolism 85(1):29-34.
Edwards, et al. (2003) "The Remarkable Flexibility of the Human Antibody Repertoire; Isolation of Over One Thousand Different Antibodies to a Single Protein", BLyS, Journal of Molecular Biology, 334:103-118.
Friedman and Halaas (1998) "Leptin and the regulation of body weight in mammals" Nature 395(6704):763-70.
Garg (2011) "Lipodystrophies: Genetic and Acquired Body Fat Disorders", Journal of Clinical Endocrinology and Metabolism, 96(11):3313-3325.
Goel, et al. (2004) "Plasticity Within The Antigen-Combining Site May Manifest as Molecular Mimicry in the Humoral Immune Response", J. Immunol., 173:7358-7367.
Gorska, et al. (2010) "Leptin Receptors", European Journal of Medical Research, 15(Supplemental II):50-54.
Justice, et al. (2016) "Using the Mouse to Model Human Disease: Increasing Validity and Reproducibility", Disease, Models & Mechanisms 9:101-103.
Kazane et al., (2012) "Synthesis of Bispecific Antibodies using Genetically Encoded Unnatural Amino Acids", J. Am. Chem. Soc., 134:9918-9921 [Epub: Dec. 4, 2012].
Khan, et al. (2014) "Adjustable Locks and Flexible Keys: Plasticity of Epitope-Paratope Interactions in Germline Antibodies", J. Immunol. 192:5398-5405.
Li, et al. (2016) "The Role of Leptin in Central Nervous System Diseases", NeuroReport 27(5):350-355.
Lin, et al. (2018) "Leptin Signaling Axis Specfically Associates with Clinical Prognosis and is Multifunctional in Regulating Cancer Progression", Oncontarget 9(24):17210-17219.
Lloyd, et al. (2009) "Modeling the Human Immune Response: Performance of a 10(11) Human Antibody Repertoire Against a Broad Panel of Therapeutically Relevant Antigens." Protein Engineering & Selection 22(3):159-168.
Mak, et al. (2014) "Exploiting The Therapeutic Potential of Leptin Signaling in Cachexia", Current Opinion in Supportive and Palliative Care 8(4):352-357.
Marcic et al. (2000) "Replacement of the Transmembrane Anchor in Angiotensin I-converting Enzyme (ACE) with a Glycosylphosphatidylinositol Tail Affects Activation of the B2 Bradykinin Receptor by ACE Inhibitors", J. Biol Chem. 275(21):16110-8.
Mayo Clinic (2015) "Lipodystrophy Syndromes: New Treatment, Newer Questions", Published online Sep. 1, 2015, 4 pages.
McMurphy et al., (2014) "The Anti-Tumor Activity of a Neutralizing Nanobody Targeting Leptin Receptor in a Mouse Model of Melanoma", PLoS One (2014) 9(2):e89895.
Moon et al. (2013) "Leptin's Role in Lipodystrophic and Nonlipodystrophic Insulin-Resistant and Diabetic Individuals", Endocrine Reviews, 34(3):377-412.
Morris, et al. (1996) "Epitope Mapping of Protein Antigens by Competition ELISA", The Protein Protocols Handbook, Humana Press, pp. 595-600.
Osorio (2014) "Leptin and Leptin Receptor Expressions in Prostate Tumors May Predict Disease Aggressiveness?", Acta Cirurgica Brasileira, 29(supl.3), 5 pages.
Padlan (1994) "Anatomy of the Antibody Molecule", Molecular Immunology, 31(3):169-217.
Park and Ahima (2014) "Leptin Signaling", F1000Prime Reports, 73(6), 8 pages.
Phillips (2001) "The Challenge of Gene Therapy and DNA Delivery", J. Pharm. Pharmacology 53:1169-1174.
International Search Report and Written Opinion received for PCT/US2017/060690 dated Jan. 10, 2018, 17pages.
Poosarla, et al. (2017) "Computational De Novo Design of Antibodies Binding to a Peptide With High Affinity", Biotechn. Bioeng., 114(6):1331-1342.
Rabia, et al. (2018) "Understanding and Overcoming Trade-Offs Between Antibody Affinity, Specificity, Stability and Solubility," Biochemical Engineer Journal, 137:365-374.
Sweeney (2002) "Leptin Signalling", Cell Signal 14(8):655-663.
University of Utah Healthcare (2014) "Knowing the Difference Between Inherited and Acquired Cancers Can Save Lives", Published online Sep. 5, 2014, 3 pages.
Zabeau et al. (2014) "Antagonizing Leptin: Current Status and Future Directions" Biol. Chem. 395(5):499-514.

\* cited by examiner

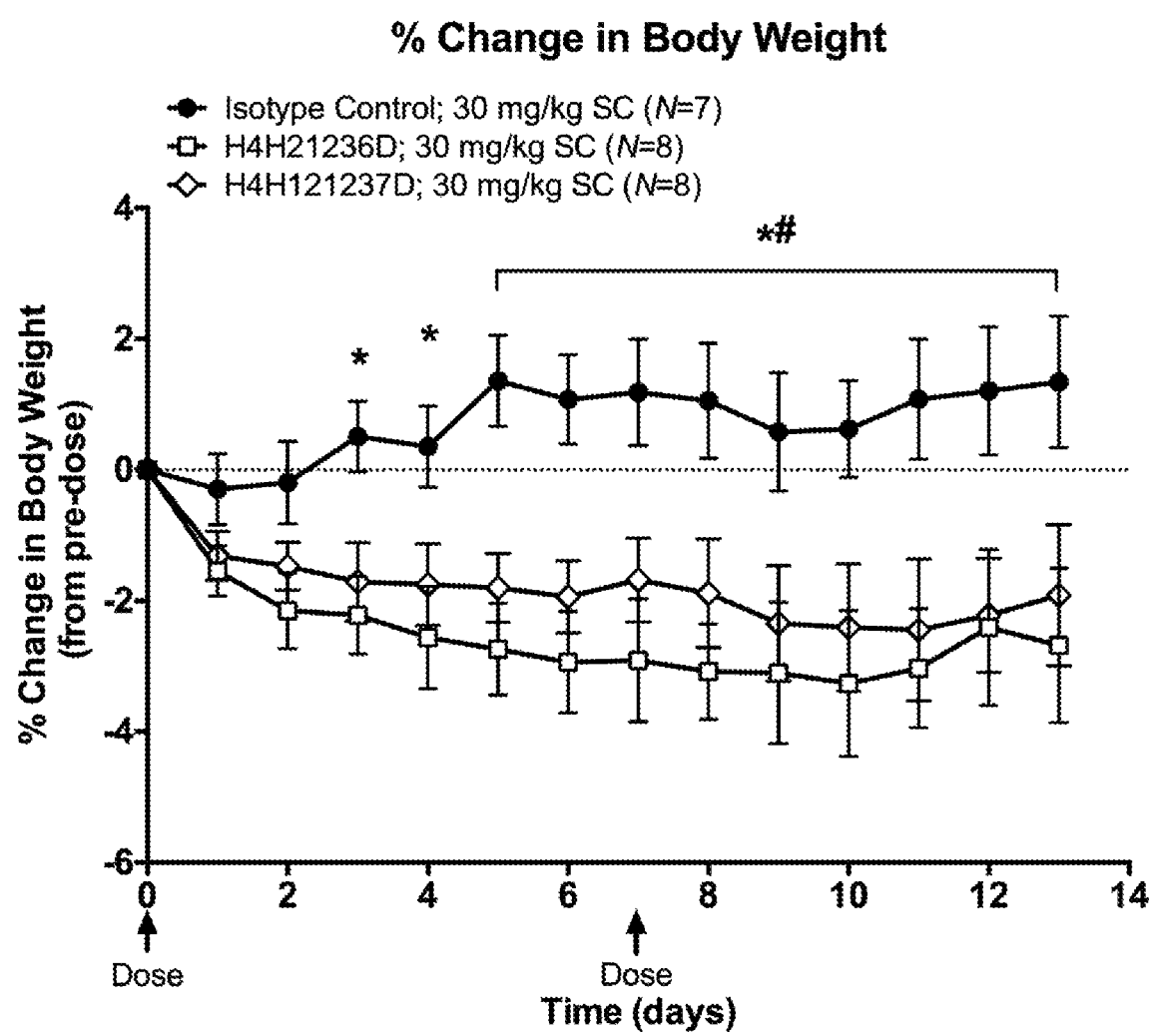

SEQUENCE LISTING

```
<160> NUMBER OF SEQ ID NOS: 198

<210> SEQ ID NO 1
<211> LENGTH: 357
<212> TYPE: DNA
<213> ORGANISM: Artificial Sequence
<220> FEATURE:
<223> OTHER INFORMATION: synthetic

<400> SEQUENCE: 1
caggtgcagc tggtggagtc cggggggaggc gtggtccagc ctgggaggtc cctgagactc      60
tcctgtacag cgtctggatt caccttcagt agttatgcca tgtactgggt ccgccaggct     120
ccaggcaagg ggctggagtg ggtgtcagtt atatactatg atggaagtta taaatactat     180
gcagactccg tgaagggccg attcaccatc tccagagaca attccaagaa cacgctgtat     240
ctgcaaatgg acagcctgag agccgaggac acggctgtct attactgtgc gagttataac     300
tggaactact ggtacttcga tttctggggc cgtggcaccc tggtcactgt ctcctca       357

<210> SEQ ID NO 2
<211> LENGTH: 119
<212> TYPE: PRT
<213> ORGANISM: Artificial Sequence
<220> FEATURE:
<223> OTHER INFORMATION: synthetic

<400> SEQUENCE: 2

Gln Val Gln Leu Val Glu Ser Gly Gly Gly Val Val Gln Pro Gly Arg
1               5                   10                  15
```

```
Ser Leu Arg Leu Ser Cys Thr Ala Ser Gly Phe Thr Phe Ser Ser Tyr
        20                  25                  30

Ala Met Tyr Trp Val Arg Gln Ala Pro Gly Lys Gly Leu Glu Trp Val
            35                  40                  45

Ser Val Ile Tyr Tyr Asp Gly Ser Tyr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Ser Tyr Asn Trp Asn Tyr Trp Tyr Phe Asp Phe Trp Gly Arg Gly
            100                 105                 110

Thr Leu Val Thr Val Ser Ser
        115
```

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggattcacct tcagtagtta tgcc                                          24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Phe Ser Ser Tyr Ala
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
atatactatg atggaagtta taaa                                          24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Tyr Tyr Asp Gly Ser Tyr Lys
1               5

<210> SEQ ID NO 7
<211> LENGTH: 36
<212> TYPE: DNA
<213> ORGANISM: Artificial Sequence
<220> FEATURE:
<223> OTHER INFORMATION: synthetic

<400> SEQUENCE: 7
gcgagttata actggaacta ctggtacttc gatttc                                    36

<210> SEQ ID NO 8
<211> LENGTH: 12
<212> TYPE: PRT
<213> ORGANISM: Artificial Sequence
<220> FEATURE:
<223> OTHER INFORMATION: synthetic

<400> SEQUENCE: 8

Ala Ser Tyr Asn Trp Asn Tyr Trp Tyr Phe Asp Phe
1               5                   10

<210> SEQ ID NO 9
<211> LENGTH: 324
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324

<210> SEQ ID NO 10
<211> LENGTH: 108
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cagagcatta gcagctat                                                          18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Ser Ile Ser Ser Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 gctgcatcc                                                                     9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Ser
1

<210> SEQ ID NO 15
<211> LENGTH: 30
<212> TYPE: DNA
<213> ORGANISM: Artificial Sequence
<220> FEATURE:
<223> OTHER INFORMATION: synthetic

<400> SEQUENCE: 15
caacagagtt acagtacccc tccgatcacc                                             30

<210> SEQ ID NO 16
<211> LENGTH: 10
<212> TYPE: PRT
<213> ORGANISM: Artificial Sequence
<220> FEATURE:
<223> OTHER INFORMATION: synthetic

<400> SEQUENCE: 16

Gln Gln Ser Tyr Ser Thr Pro Pro Ile Thr
1               5                   10

<210> SEQ ID NO 17
<211> LENGTH: 354
<212> TYPE: DNA
<213> ORGANISM: Artificial Sequence
<220> FEATURE:
<223> OTHER INFORMATION: synthetic

<400> SEQUENCE: 17
caggtgcagc tggtggagtc tgggggaggc gtggtccagc cggggggggtc cctgagactc           60

```
tcctgtgcag cctctggatt caccttcagt acttatgaca ttcactgggt ccgccaggct    120
ccaggcaagg ggctggagtg ggtggcagtc atatcttttg atggaagtaa tagaaattat    180
ggagactccg tgaagggccg attcaccatc tccagggaca attccgacaa taccctgttt    240
ctggaaatga acaatctgag atttgaagac acggctgtgt attactgtgc gaaagagggc    300
tacggtgttg acttccaaca ctggggccag ggcaccctgg tcaccgtctc ctca          354
```

```
<210> SEQ ID NO 18
<211> LENGTH: 118
<212> TYPE: PRT
<213> ORGANISM: Artificial Sequence
<220> FEATURE:
<223> OTHER INFORMATION: synthetic

<400> SEQUENCE: 18
```

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Thr Tyr
            20                  25                  30

Asp Ile His Trp Val Arg Gln Ala Pro Gly Lys Gly Leu Glu Trp Val
        35                  40                  45

Ala Val Ile Ser Phe Asp Gly Ser Asn Arg Asn Tyr Gly Asp Ser Val
    50                  55                  60

Lys Gly Arg Phe Thr Ile Ser Arg Asp Asn Ser Asp Asn Thr Leu Phe
65                  70                  75                  80

Leu Glu Met Asn Asn Leu Arg Phe Glu Asp Thr Ala Val Tyr Tyr Cys
                85                  90                  95

Ala Lys Glu Gly Tyr Gly Val Asp Phe Gln His Trp Gly Gln Gly Thr
            100                 105                 110

Leu Val Thr Val Ser Ser
        115

```
<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcacct tcagtactta tgac                                            24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20
```

Gly Phe Thr Phe Ser Thr Tyr Asp
1               5

```
<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
```
atatcttttg atggaagtaa taga                                                24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Ser Phe Asp Gly Ser Asn Arg
1               5

<210> SEQ ID NO 23
<211> LENGTH: 33
<212> TYPE: DNA
<213> ORGANISM: Artificial Sequence
<220> FEATURE:
<223> OTHER INFORMATION: synthetic

<400> SEQUENCE: 23
gcgaaagagg gctacggtgt tgacttccaa cac                                      33

<210> SEQ ID NO 24
<211> LENGTH: 11
<212> TYPE: PRT
<213> ORGANISM: Artificial Sequence
<220> FEATURE:
<223> OTHER INFORMATION: synthetic

<400> SEQUENCE: 24

Ala Lys Glu Gly Tyr Gly Val Asp Phe Gln His
1               5                   10

<210> SEQ ID NO 25
<211> LENGTH: 384
<212> TYPE: DNA
<213> ORGANISM: Artificial Sequence
<220> FEATURE:
<223> OTHER INFORMATION: synthetic

<400> SEQUENCE: 25
caggtgcagc tgcaggagtc gggcccagga ctggtgaagc cttcggagac cctgtccctc          60
acctgcactg tctctggtgg ctccatcagt aattactact ggacctggat ccggcagccc         120
ccagggaagg gactggagtg gattgggcat atctctaaca gtgggaccac caactataac         180
ccctccctca gagtcgagt caccatatca gtagacacgt ccaagaacca gttctccctg         240
aagctgacct ctgtgaccgc cgcagacacg gccgtgtatt actgtgcgag actccccctc         300
ggtattgcag cagttgatac agattattat tattacttcg gtatggacgt ctggggccaa         360
gggaccacgg tcaccgtctc ctca                                              384

<210> SEQ ID NO 26
<211> LENGTH: 128
<212> TYPE: PRT
<213> ORGANISM: Artificial Sequence
<220> FEATURE:
<223> OTHER INFORMATION: synthetic

<400> SEQUENCE: 26

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

```
Tyr Trp Thr Trp Ile Arg Gln Pro Pro Gly Lys Gly Leu Glu Trp Ile
            35                  40                  45
Gly His Ile Ser Asn Ser Gly Thr Thr Asn Tyr Asn Pro Ser Leu Lys
        50                  55                  60
Ser Arg Val Thr Ile Ser Val Asp Thr Ser Lys Asn Gln Phe Ser Leu
65                  70                  75                  80
Lys Leu Thr Ser Val Thr Ala Ala Asp Thr Ala Val Tyr Tyr Cys Ala
                85                  90                  95
Arg Leu Pro Leu Gly Ile Ala Ala Val Asp Thr Asp Tyr Tyr Tyr Tyr
            100                 105                 110
Phe Gly Met Asp Val Trp Gly Gln Gly Thr Thr Val Thr Val Ser Ser
        115                 120                 125
```

<210> SEQ ID NO 27
<211> LENGTH: 24
<212> TYPE: DNA
<213> ORGANISM: Artificial Sequence
<220> FEATURE:
<223> OTHER INFORMATION: synthetic

<400> SEQUENCE: 27
ggtggctcca tcagtaatta ctac                                            24

<210> SEQ ID NO 28
<211> LENGTH: 8
<212> TYPE: PRT
<213> ORGANISM: Artificial Sequence
<220> FEATURE:
<223> OTHER INFORMATION: synthetic

<400> SEQUENCE: 28

Gly Gly Ser Ile Ser Asn Tyr Tyr
1               5

<210> SEQ ID NO 29
<211> LENGTH: 21
<212> TYPE: DNA
<213> ORGANISM: Artificial Sequence
<220> FEATURE:
<223> OTHER INFORMATION: synthetic

<400> SEQUENCE: 29
atctctaaca gtgggaccac c                                               21

<210> SEQ ID NO 30
<211> LENGTH: 7
<212> TYPE: PRT
<213> ORGANISM: Artificial Sequence
<220> FEATURE:
<223> OTHER INFORMATION: synthetic

<400> SEQUENCE: 30

Ile Ser Asn Ser Gly Thr Thr
1               5

<210> SEQ ID NO 31
<211> LENGTH: 66
<212> TYPE: DNA
<213> ORGANISM: Artificial Sequence
<220> FEATURE:
<223> OTHER INFORMATION: synthetic

<400> SEQUENCE: 31

```
gcgagactcc ccctcggtat tgcagcagtt gatacagatt attattatta cttcggtatg    60
gacgtc                                                               66
```

<210> SEQ ID NO 32
<211> LENGTH: 22
<212> TYPE: PRT
<213> ORGANISM: Artificial Sequence
<220> FEATURE:
<223> OTHER INFORMATION: synthetic

<400> SEQUENCE: 32

```
Ala Arg Leu Pro Leu Gly Ile Ala Ala Val Asp Thr Asp Tyr Tyr Tyr
1               5                   10                  15

Tyr Phe Gly Met Asp Val
            20
```

<210> SEQ ID NO 33
<211> LENGTH: 348
<212> TYPE: DNA
<213> ORGANISM: Artificial Sequence
<220> FEATURE:
<223> OTHER INFORMATION: synthetic

<400> SEQUENCE: 33

```
gaggtgcagc tggtggagtc tgggggaggt gtggtacggc ctggggggtc cctgagactc    60
tcctgtacag cctctggatt cacctttgat gattatggca tgagctgggt ccgccaagct   120
ccagggaagg gactggagtg ggtctctggt attaattgga atggtggtag aacagaatat   180
gcagacgctg tgaagggccg attcatcatc tccagagaca cgccaagaa ctccctgtat    240 ctgcaaatga acagtctgag agccgaggac acggccttgt atttctgtgc gagaacggaa   300
ttacggtggg actactgggg ccagggaacc ctggtcaccg tctcctca               348
```

<210> SEQ ID NO 34
<211> LENGTH: 116
<212> TYPE: PRT
<213> ORGANISM: Artificial Sequence
<220> FEATURE:
<223> OTHER INFORMATION: synthetic

<400> SEQUENCE: 34

```
Glu Val Gln Leu Val Glu Ser Gly Gly Gly Val Val Arg Pro Gly Gly
1               5                   10                  15

Ser Leu Arg Leu Ser Cys Thr Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Arg Thr Glu Tyr Ala Asp Ala Val
    50                  55                  60

Lys Gly Arg Phe Ile Ile Ser Arg Asp Asn Ala Lys Asn Ser Leu Tyr
65                  70                  75                  80

Leu Gln Met Asn Ser Leu Arg Ala Glu Asp Thr Ala Leu Tyr Phe Cys
                85                  90                  95

Ala Arg Thr Glu Leu Arg Trp Asp Tyr Trp Gly Gln Gly Thr Leu Val
            100                 105                 110

Thr Val Ser Ser
        115
```

<210> SEQ ID NO 35
<211> LENGTH: 24

```
<212> TYPE: DNA
<213> ORGANISM: Artificial Sequence
<220> FEATURE:
<223> OTHER INFORMATION: synthetic

<400> SEQUENCE: 35
ggattcacct ttgatgatta tggc                                              24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Phe Thr Phe Asp Asp Tyr Gly
1               5

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
attaattgga atggtggtag aaca                                              24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Ile Asn Trp Asn Gly Gly Arg Thr
1               5

<210> SEQ ID NO 39
<211> LENGTH: 27
<212> TYPE: DNA
<213> ORGANISM: Artificial Sequence
<220> FEATURE:
<223> OTHER INFORMATION: synthetic

<400> SEQUENCE: 39
gcgagaacgg aattacggtg ggactac                                           27

<210> SEQ ID NO 40
<211> LENGTH: 9
<212> TYPE: PRT
<213> ORGANISM: Artificial Sequence
<220> FEATURE:
<223> OTHER INFORMATION: synthetic

<400> SEQUENCE: 40

Ala Arg Thr Glu Leu Arg Trp Asp Tyr
1               5

<210> SEQ ID NO 41
<211> LENGTH: 363
<212> TYPE: DNA
<213> ORGANISM: Artificial Sequence
<220> FEATURE:
<223> OTHER INFORMATION: synthetic
```

<400> SEQUENCE: 41

```
gaggtgcagc tggtggagtc tgggggaggc ttggtacagc ctggagggtc cctgagactc    60
tcctgtgcag cctctggact caccttcagt agttatgaaa tgaactgggt ccgccaggct   120
ccagggaagg ggctggagtg ggtttcacac attagtagtg ctggtagtac caaatactac   180
gcagactctg tgaagggccg attcaccatc tccagagaca acgccaagaa ctcactgttt   240
ctgcaaatga acagcctgag agccgaggac acggctattt attactgtgc gggctataac   300
tacgcctact actacttcgg tgtggacgtc tggggccaag gaccacggt caccgtctcc   360
tca                                                                 363
```

<210> SEQ ID NO 42
<211> LENGTH: 121
<212> TYPE: PRT
<213> ORGANISM: Artificial Sequence
<220> FEATURE:
<223> OTHER INFORMATION: synthetic

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Glu Met Asn Trp Val Arg Gln Ala Pro Gly Lys Gly Leu Glu Trp Val
        35                  40                  45

Ser His Ile Ser Ser Ala Gly Ser Thr Lys Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Ile Tyr Tyr Cys
                85                  90                  95

Ala Gly Tyr Asn Tyr Ala Tyr Tyr Tyr Phe Gly Val Asp Val Trp Gly
            100                 105                 110

Gln Gly Thr Thr Val Thr Val Ser Ser
        115                 120
```

<210> SEQ ID NO 43
<211> LENGTH: 24
<212> TYPE: DNA
<213> ORGANISM: Artificial Sequence
<220> FEATURE:
<223> OTHER INFORMATION: synthetic

<400> SEQUENCE: 43

```
ggactcacct tcagtagtta tgaa                                           24
```

<210> SEQ ID NO 44
<211> LENGTH: 8
<212> TYPE: PRT
<213> ORGANISM: Artificial Sequence
<220> FEATURE:
<223> OTHER INFORMATION: synthetic

<400> SEQUENCE: 44

```
Gly Leu Thr Phe Ser Ser Tyr Glu
1               5
```

<210> SEQ ID NO 45
<211> LENGTH: 24

```
<212> TYPE: DNA
<213> ORGANISM: Artificial Sequence
<220> FEATURE:
<223> OTHER INFORMATION: synthetic

<400> SEQUENCE: 45
attagtagtg ctggtagtac caaa                                             24

<210> SEQ ID NO 46
<211> LENGTH: 8
<212> TYPE: PRT
<213> ORGANISM: Artificial Sequence
<220> FEATURE:
<223> OTHER INFORMATION: synthetic

<400> SEQUENCE: 46

Ile Ser Ser Ala Gly Ser Thr Lys
1               5

<210> SEQ ID NO 47
<211> LENGTH: 42
<212> TYPE: DNA
<213> ORGANISM: Artificial Sequence
<220> FEATURE:
<223> OTHER INFORMATION: synthetic

<400> SEQUENCE: 47
gcgggctata actacgccta ctactacttc ggtgtggacg tc                         42

<210> SEQ ID NO 48
<211> LENGTH: 14
<212> TYPE: PRT
<213> ORGANISM: Artificial Sequence
<220> FEATURE:
<223> OTHER INFORMATION: synthetic

<400> SEQUENCE: 48

Ala Gly Tyr Asn Tyr Ala Tyr Tyr Phe Gly Val Asp Val
1               5                   10

<210> SEQ ID NO 49
<211> LENGTH: 360
<212> TYPE: DNA
<213> ORGANISM: Artificial Sequence
<220> FEATURE:
<223> OTHER INFORMATION: synthetic

<400> SEQUENCE: 49
cagctgcagc tgcaggagtc gggcccagga ctggtgaagc cttcggagac cctgtccctc       60
atttgcactg tctctggtgg ctccatcagc agtaataatt actactgggg ctggatccgc      120
cagcccccag ggaaggggct ggaatggatt gggaatttgt atggtagtgg gagtacctac      180
tacaacccgt ccctcaagag tcgagtcacc atatccgtag acacgtccaa gaaccagttc      240
tccctgaagc tgagttttgt gaccgccgca gacacggctg tgtatcactg tgcgagatgg      300
gacactaacg gggggctttt tgatatctgg ggccaaggga caatggtcac cgtctcttca      360

<210> SEQ ID NO 50
<211> LENGTH: 120
<212> TYPE: PRT
<213> ORGANISM: Artificial Sequence
<220> FEATURE:
<223> OTHER INFORMATION: synthetic

<400> SEQUENCE: 50
```

```
Gln Leu Gln Leu Gln Glu Ser Gly Pro Gly Leu Val Lys Pro Ser Glu
1               5                   10                  15

Thr Leu Ser Leu Ile Cys Thr Val Ser Gly Gly Ser Ile Ser Ser Asn
            20                  25                  30

Asn Tyr Tyr Trp Gly Trp Ile Arg Gln Pro Pro Gly Lys Gly Leu Glu
        35                  40                  45

Trp Ile Gly Asn Leu Tyr Gly Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Phe Val Thr Ala Ala Asp Thr Ala Val Tyr His
                85                  90                  95

Cys Ala Arg Trp Asp Thr Asn Gly Gly Ala Phe Asp Ile Trp Gly Gln
            100                 105                 110

Gly Thr Met Val Thr Val Ser Ser
            115                 120

<210> SEQ ID NO 51
<211> LENGTH: 30
<212> TYPE: DNA
<213> ORGANISM: Artificial Sequence
<220> FEATURE:
<223> OTHER INFORMATION: synthetic

<400> SEQUENCE: 51
ggtggctcca tcagcagtaa taattactac                                      30

<210> SEQ ID NO 52
<211> LENGTH: 10
<212> TYPE: PRT
<213> ORGANISM: Artificial Sequence
<220> FEATURE:
<223> OTHER INFORMATION: synthetic

<400> SEQUENCE: 52

Gly Gly Ser Ile Ser Ser Asn Asn Tyr Tyr
1               5                   10

<210> SEQ ID NO 53
<211> LENGTH: 21
<212> TYPE: DNA
<213> ORGANISM: Artificial Sequence
<220> FEATURE:
<223> OTHER INFORMATION: synthetic

<400> SEQUENCE: 53
ttgtatggta gtgggagtac c                                               21

<210> SEQ ID NO 54
<211> LENGTH: 7
<212> TYPE: PRT
<213> ORGANISM: Artificial Sequence
<220> FEATURE:
<223> OTHER INFORMATION: synthetic

<400> SEQUENCE: 54

Leu Tyr Gly Ser Gly Ser Thr
1               5

<210> SEQ ID NO 55
<211> LENGTH: 36
<212> TYPE: DNA
<213> ORGANISM: Artificial Sequence
```

```
<220> FEATURE:
<223> OTHER INFORMATION: synthetic

<400> SEQUENCE: 55
gcgagatggg acactaacgg gggggctttt gatatc                                    36

<210> SEQ ID NO 56
<211> LENGTH: 12
<212> TYPE: PRT
<213> ORGANISM: Artificial Sequence
<220> FEATURE:
<223> OTHER INFORMATION: synthetic

<400> SEQUENCE: 56

Ala Arg Trp Asp Thr Asn Gly Gly Ala Phe Asp Ile
1               5                   10

<210> SEQ ID NO 57
<211> LENGTH: 345
<212> TYPE: DNA
<213> ORGANISM: Artificial Sequence
<220> FEATURE:
<223> OTHER INFORMATION: synthetic

<400> SEQUENCE: 57
caggttcagc tggtgcagtc tggagctgag gtgaagaagc ctggggcctc agtgaaggtc          60
tcctgcaagg cttctggtta cacctttacc agccttggaa tcagctgggt gcgacaggcc         120
cctggacaag gcttgagtg atgggatgg atcagcgcct acagtggtaa tagagactat          180
gcacagaagt tccagggcag agtcaccatg accacagaca catccacgag cacagcctat         240
atggagctga ggagcctgag atctgacgac acggccgtgt attattgtgc gagatctcta         300
cgttttgact actggggcca gggaaccctg gtcaccgtct cctca                         345

<210> SEQ ID NO 58
<211> LENGTH: 115
<212> TYPE: PRT
<213> ORGANISM: Artificial Sequence
<220> FEATURE:
<223> OTHER INFORMATION: synthetic

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Leu
                20                  25                  30

Gly Ile Ser Trp Val Arg Gln Ala Pro Gly Gln Gly Leu Glu Trp Met
            35                  40                  45

Gly Trp Ile Ser Ala Tyr Ser Gly Asn Arg Asp Tyr Ala Gln Lys Phe
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Leu Arg Phe Asp Tyr Trp Gly Gln Gly Thr Leu Val Thr
            100                 105                 110

Val Ser Ser
        115

<210> SEQ ID NO 59
<211> LENGTH: 24
```

<212> TYPE: DNA
<213> ORGANISM: Artificial Sequence
<220> FEATURE:
<223> OTHER INFORMATION: synthetic

<400> SEQUENCE: 59
ggttacacct ttaccagcct tgga                                              24

<210> SEQ ID NO 60
<211> LENGTH: 8
<212> TYPE: PRT
<213> ORGANISM: Artificial Sequence
<220> FEATURE:
<223> OTHER INFORMATION: synthetic

<400> SEQUENCE: 60

Gly Tyr Thr Phe Thr Ser Leu Gly
1               5

<210> SEQ ID NO 61
<211> LENGTH: 24
<212> TYPE: DNA
<213> ORGANISM: Artificial Sequence
<220> FEATURE:
<223> OTHER INFORMATION: synthetic

<400> SEQUENCE: 61
atcagcgcct acagtggtaa taga                                              24

<210> SEQ ID NO 62
<211> LENGTH: 8
<212> TYPE: PRT
<213> ORGANISM: Artificial Sequence
<220> FEATURE:
<223> OTHER INFORMATION: synthetic

<400> SEQUENCE: 62

Ile Ser Ala Tyr Ser Gly Asn Arg
1               5

<210> SEQ ID NO 63
<211> LENGTH: 24
<212> TYPE: DNA
<213> ORGANISM: Artificial Sequence
<220> FEATURE:
<223> OTHER INFORMATION: synthetic

<400> SEQUENCE: 63
gcgagatctc tacgttttga ctac                                              24

<210> SEQ ID NO 64
<211> LENGTH: 8
<212> TYPE: PRT
<213> ORGANISM: Artificial Sequence
<220> FEATURE:
<223> OTHER INFORMATION: synthetic

<400> SEQUENCE: 64

Ala Arg Ser Leu Arg Phe Asp Tyr
1               5

<210> SEQ ID NO 65
<211> LENGTH: 357
<212> TYPE: DNA
<213> ORGANISM: Artificial Sequence
<220> FEATURE:
<223> OTHER INFORMATION: synthetic

<400> SEQUENCE: 65

```
gaggtgcagc tggtggagtc tgggggaggc ttggtacagc ctggcaggtc cctgagactc    60
tcctgtgcag cctcaggatt caccttggat gattttgcca tgcactgggt ccggcaagct   120
ccagggaagg gcctggagtg gtctcaggt attagttgga atagcggtaa tataggttat   180
gcggactctg tgaagggccg cttcaccatc tccagagaca acgccaggaa ctccctgtat   240
ctgcaaatga acagtctgag agcggaagac acggccttgt attactgcac ctcgggatac   300
tacctctact acgctatgga cgtctggggc caggggacca cggtcaccgt ctcctca      357
```

<210> SEQ ID NO 66
<211> LENGTH: 119
<212> TYPE: PRT
<213> ORGANISM: Artificial Sequence
<220> FEATURE:
<223> OTHER INFORMATION: synthetic

<400> SEQUENCE: 66

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Leu Asp Asp Phe
            20                  25                  30

Ala Met His Trp Val Arg Gln Ala Pro Gly Lys Gly Leu Glu Trp Val
        35                  40                  45

Ser Gly Ile Ser Trp Asn Ser Gly Asn Ile Gly Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Leu Tyr Tyr Cys
                85                  90                  95

Thr Ser Gly Tyr Tyr Leu Tyr Tyr Ala Met Asp Val Trp Gly Gln Gly
            100                 105                 110

Thr Thr Val Thr Val Ser Ser
        115

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67

```
ggattcacct tggatgattt tgcc                                            24
```

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

Gly Phe Thr Leu Asp Asp Phe Ala
1               5

<210> SEQ ID NO 69
<211> LENGTH: 24
<212> TYPE: DNA
<213> ORGANISM: Artificial Sequence

```
<220> FEATURE:
<223> OTHER INFORMATION: synthetic

<400> SEQUENCE: 69
attagttgga atagcggtaa tata                                              24

<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

Ile Ser Trp Asn Ser Gly Asn Ile
1               5

<210> SEQ ID NO 71
<211> LENGTH: 36
<212> TYPE: DNA
<213> ORGANISM: Artificial Sequence
<220> FEATURE:
<223> OTHER INFORMATION: synthetic

<400> SEQUENCE: 71
acctcgggat actacctcta ctacgctatg gacgtc                                 36

<210> SEQ ID NO 72
<211> LENGTH: 12
<212> TYPE: PRT
<213> ORGANISM: Artificial Sequence
<220> FEATURE:
<223> OTHER INFORMATION: synthetic

<400> SEQUENCE: 72

Thr Ser Gly Tyr Tyr Leu Tyr Tyr Ala Met Asp Val
1               5                   10

<210> SEQ ID NO 73
<211> LENGTH: 357
<212> TYPE: DNA
<213> ORGANISM: Artificial Sequence
<220> FEATURE:
<223> OTHER INFORMATION: synthetic

<400> SEQUENCE: 73
caggtgcagc tggtgcagtc tgggcctgag gtgaagaagc ctgggtcttc ggtgaaggtc        60
tcctgcaagg cttctggagg caccatcgac agaaatgaaa tcacctgggt gcgacaggcc      120
cctggacaag ggcttgagtg gatgggagta atcatcccta tcttaggtga ggcacactac      180
gaacgaaaat tccagggcag actcacgatt accatggacg agtccacgag tacagcctat      240
atggaactga gtaatctgag atctgaggac acggccgtat attactgtgc gagagagagg      300
gcagctcgag gctaccttga ctactggggc cagggaaccc tggtcaccgt ctcctca        357

<210> SEQ ID NO 74
<211> LENGTH: 119
<212> TYPE: PRT
<213> ORGANISM: Artificial Sequence
<220> FEATURE:
<223> OTHER INFORMATION: synthetic

<400> SEQUENCE: 74

Gln Val Gln Leu Val Gln Ser Gly Pro Glu Val Lys Lys Pro Gly Ser
1               5                   10                  15
```

```
Ser Val Lys Val Ser Cys Lys Ala Ser Gly Gly Thr Ile Asp Arg Asn
         20                  25                  30

Glu Ile Thr Trp Val Arg Gln Ala Pro Gly Gln Gly Leu Glu Trp Met
     35                  40                  45

Gly Val Ile Ile Pro Ile Leu Gly Glu Ala His Tyr Glu Arg Lys Phe
 50                  55                  60

Gln Gly Arg Leu Thr Ile Thr Met Asp Glu Ser Thr Ser Thr Ala Tyr
65                  70                  75                  80

Met Glu Leu Ser Asn Leu Arg Ser Glu Asp Thr Ala Val Tyr Tyr Cys
                 85                  90                  95

Ala Arg Glu Arg Ala Ala Arg Gly Tyr Leu Asp Tyr Trp Gly Gln Gly
            100                 105                 110

Thr Leu Val Thr Val Ser Ser
        115

<210> SEQ ID NO 75
<211> LENGTH: 24
<212> TYPE: DNA
<213> ORGANISM: Artificial Sequence
<220> FEATURE:
<223> OTHER INFORMATION: synthetic

<400> SEQUENCE: 75
ggaggcacca tcgacagaaa tgaa                                          24

<210> SEQ ID NO 76
<211> LENGTH: 8
<212> TYPE: PRT
<213> ORGANISM: Artificial Sequence
<220> FEATURE:
<223> OTHER INFORMATION: synthetic

<400> SEQUENCE: 76

Gly Gly Thr Ile Asp Arg Asn Glu
1               5

<210> SEQ ID NO 77
<211> LENGTH: 24
<212> TYPE: DNA
<213> ORGANISM: Artificial Sequence
<220> FEATURE:
<223> OTHER INFORMATION: synthetic

<400> SEQUENCE: 77
atcatcccta tcttaggtga ggca                                          24

<210> SEQ ID NO 78
<211> LENGTH: 8
<212> TYPE: PRT
<213> ORGANISM: Artificial Sequence
<220> FEATURE:
<223> OTHER INFORMATION: synthetic

<400> SEQUENCE: 78

Ile Ile Pro Ile Leu Gly Glu Ala
1               5

<210> SEQ ID NO 79
<211> LENGTH: 36
<212> TYPE: DNA
<213> ORGANISM: Artificial Sequence
<220> FEATURE:
<223> OTHER INFORMATION: synthetic
```

<400> SEQUENCE: 79
gcgagagaga gggcagctcg aggctacctt gactac                               36

<210> SEQ ID NO 80
<211> LENGTH: 12
<212> TYPE: PRT
<213> ORGANISM: Artificial Sequence
<220> FEATURE:
<223> OTHER INFORMATION: synthetic

<400> SEQUENCE: 80

Ala Arg Glu Arg Ala Ala Arg Gly Tyr Leu Asp Tyr
1               5                   10

<210> SEQ ID NO 81
<211> LENGTH: 360
<212> TYPE: DNA
<213> ORGANISM: Artificial Sequence
<220> FEATURE:
<223> OTHER INFORMATION: synthetic

<400> SEQUENCE: 81
gaggtgcagc tggtggagtc tgggggaggc ttggtccagc cggggggtc cctgagactc      60 tcctgtacag cctctggatt caccttcagt aattatgcta tattctgggt ccgccaggct    120
ccagggaagg gactggaata tgtttcaggt attagtaata tgggggttac taaatattat    180
gcagactctg tgagggacag attcaccatc tccagagaca attccaggaa cacggtgtct    240
attcaaatgg acagcctgag aactgaggac atggctgtgt attactgtgc gcgagaaaac    300
tggggatcgg acgatggttt tgatatctgg ggccaaggaa caatggtcac cgtctcttca    360

<210> SEQ ID NO 82
<211> LENGTH: 120
<212> TYPE: PRT
<213> ORGANISM: Artificial Sequence
<220> FEATURE:
<223> OTHER INFORMATION: synthetic

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Asn Tyr
            20                  25                  30

Ala Ile Phe Trp Val Arg Gln Ala Pro Gly Lys Gly Leu Glu Tyr Val
        35                  40                  45

Ser Gly Ile Ser Asn Asn Gly Val Thr Lys Tyr Tyr Ala Asp Ser Val
    50                  55                  60

Arg Asp Arg Phe Thr Ile Ser Arg Asp Asn Arg Asn Thr Val Ser
65                  70                  75                  80

Ile Gln Met Asp Ser Leu Arg Thr Glu Asp Met Ala Val Tyr Tyr Cys
                85                  90                  95

Ala Arg Glu Asn Trp Gly Ser Asp Asp Gly Phe Asp Ile Trp Gly Gln
            100                 105                 110

Gly Thr Met Val Thr Val Ser Ser
        115                 120

<210> SEQ ID NO 83
<211> LENGTH: 24
<212> TYPE: DNA
<213> ORGANISM: Artificial Sequence

```
<220> FEATURE:
<223> OTHER INFORMATION: synthetic

<400> SEQUENCE: 83
ggattcacct tcagtaatta tgct                                              24

<210> SEQ ID NO 84
<211> LENGTH: 8
<212> TYPE: PRT
<213> ORGANISM: Artificial Sequence
<220> FEATURE:
<223> OTHER INFORMATION: synthetic

<400> SEQUENCE: 84

Gly Phe Thr Phe Ser Asn Tyr Ala
1               5

<210> SEQ ID NO 85
<211> LENGTH: 24
<212> TYPE: DNA
<213> ORGANISM: Artificial Sequence
<220> FEATURE:
<223> OTHER INFORMATION: synthetic

<400> SEQUENCE: 85
attagtaata atgggggttac taaa                                             24

<210> SEQ ID NO 86
<211> LENGTH: 8
<212> TYPE: PRT
<213> ORGANISM: Artificial Sequence
<220> FEATURE:
<223> OTHER INFORMATION: synthetic

<400> SEQUENCE: 86

Ile Ser Asn Asn Gly Val Thr Lys
1               5

<210> SEQ ID NO 87
<211> LENGTH: 39
<212> TYPE: DNA
<213> ORGANISM: Artificial Sequence
<220> FEATURE:
<223> OTHER INFORMATION: synthetic

<400> SEQUENCE: 87
gcgcgagaaa actggggatc ggacgatggt tttgatatc                              39

<210> SEQ ID NO 88
<211> LENGTH: 13
<212> TYPE: PRT
<213> ORGANISM: Artificial Sequence
<220> FEATURE:
<223> OTHER INFORMATION: synthetic

<400> SEQUENCE: 88

Ala Arg Glu Asn Trp Gly Ser Asp Asp Gly Phe Asp Ile
1               5                   10

<210> SEQ ID NO 89
<211> LENGTH: 357
<212> TYPE: DNA
<213> ORGANISM: Artificial Sequence
<220> FEATURE:
<223> OTHER INFORMATION: synthetic

<400> SEQUENCE: 89
```

```
caggtgcagt tggtgcagtc tgggactgag gtgaagaagc ctgggtcctc ggtgaaggtc      60
tcctgcaagg cttctggagg caccttcagc acctatccta tcaattgggt gcgacaggcc     120
cctggacaag ggcttgagtg gatgggaggg atcatcccta tctttggtac ggcaagctac     180
gcacagaagt tccagggcag agtcgcgatt accacgacg aatccacgag cacagcctac      240
atggagctga acagcctgag atctgaggac acggccgtgt attattgtgc gagagagagg     300
ccgaactggg gatctaatga ctactggggc cagggaaccc tggtcaccgt ctcctca       357
```

```
<210> SEQ ID NO 90
<211> LENGTH: 119
<212> TYPE: PRT
<213> ORGANISM: Artificial Sequence
<220> FEATURE:
<223> OTHER INFORMATION: synthetic

<400> SEQUENCE: 90

Gln Val Gln Leu Val Gln Ser Gly Thr Glu Val Lys Lys Pro Gly Ser
1               5                   10                  15

Ser Val Lys Val Ser Cys Lys Ala Ser Gly Gly Thr Phe Ser Thr Tyr
            20                  25                  30

Pro Ile Asn Trp Val Arg Gln Ala Pro Gly Gln Gly Leu Glu Trp Met
        35                  40                  45

Gly Gly Ile Ile Pro Ile Phe Gly Thr Ala Ser Tyr Ala Gln Lys Phe
    50                  55                  60

Gln Gly Arg Val Ala Ile Thr Thr Asp Glu Ser Thr Ser Thr Ala Tyr
65                  70                  75                  80

Met Glu Leu Asn Ser Leu Arg Ser Glu Asp Thr Ala Val Tyr Tyr Cys
                85                  90                  95

Ala Arg Glu Arg Pro Asn Trp Gly Ser Asn Asp Tyr Trp Gly Gln Gly
            100                 105                 110

Thr Leu Val Thr Val Ser Ser
        115
```

```
<210> SEQ ID NO 91
<211> LENGTH: 24
<212> TYPE: DNA
<213> ORGANISM: Artificial Sequence
<220> FEATURE:
<223> OTHER INFORMATION: synthetic

<400> SEQUENCE: 91
ggaggcacct tcagcaccta tcct                                             24
```

```
<210> SEQ ID NO 92
<211> LENGTH: 8
<212> TYPE: PRT
<213> ORGANISM: Artificial Sequence
<220> FEATURE:
<223> OTHER INFORMATION: synthetic

<400> SEQUENCE: 92

Gly Gly Thr Phe Ser Thr Tyr Pro
1               5
```

```
<210> SEQ ID NO 93
<211> LENGTH: 24
<212> TYPE: DNA
<213> ORGANISM: Artificial Sequence
<220> FEATURE:
<223> OTHER INFORMATION: synthetic
```

<400> SEQUENCE: 93
atcatcccta tctttggtac ggca                                              24

<210> SEQ ID NO 94
<211> LENGTH: 8
<212> TYPE: PRT
<213> ORGANISM: Artificial Sequence
<220> FEATURE:
<223> OTHER INFORMATION: synthetic

<400> SEQUENCE: 94

Ile Ile Pro Ile Phe Gly Thr Ala
1               5

<210> SEQ ID NO 95
<211> LENGTH: 36
<212> TYPE: DNA
<213> ORGANISM: Artificial Sequence
<220> FEATURE:
<223> OTHER INFORMATION: synthetic

<400> SEQUENCE: 95
gcgagagaga ggccgaactg gggatctaat gactac                                 36

<210> SEQ ID NO 96
<211> LENGTH: 12
<212> TYPE: PRT
<213> ORGANISM: Artificial Sequence
<220> FEATURE:
<223> OTHER INFORMATION: synthetic

<400> SEQUENCE: 96

Ala Arg Glu Arg Pro Asn Trp Gly Ser Asn Asp Tyr
1               5                   10

<210> SEQ ID NO 97
<211> LENGTH: 366
<212> TYPE: DNA
<213> ORGANISM: Artificial Sequence
<220> FEATURE:
<223> OTHER INFORMATION: synthetic

<400> SEQUENCE: 97
caggtgcagc tggtggagtc tgggggaggc gtggtccagc ctggggaggtc cctgagactc      60 gcctgtgcag cgtctggatt cacctttaga agttatggca tgcactgggt ccgccaggct     120
ccaggcaagg ggctggagtg gtggcagtt atctggtatg atggaagtaa taatactat       180 acagactccg tgaagggccg attcaccatc tccagagaca attccaagaa cacgctgtat    240
ctgcaaatga acagcctgag agccgaggac acggctatgt attactgtgc gatagacaaa    300
tgggctacgg tgactacgta cctgtttgac tactggggcc agggaacccct ggtcaccgtc    360 tcctca                                                                366

<210> SEQ ID NO 98
<211> LENGTH: 122
<212> TYPE: PRT
<213> ORGANISM: Artificial Sequence
<220> FEATURE:
<223> OTHER INFORMATION: synthetic

<400> SEQUENCE: 98

Gln Val Gln Leu Val Glu Ser Gly Gly Gly Val Val Gln Pro Gly Arg
1               5                   10                  15

-continued

```
Ser Leu Arg Leu Ala Cys Ala Ala Ser Gly Phe Thr Phe Arg Ser Tyr
        20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Ile Asp Lys Trp Ala Thr Val Thr Thr Tyr Leu Phe Asp Tyr Trp
            100                 105                 110

Gly Gln Gly Thr Leu Val Thr Val Ser Ser
        115                 120
```

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99
ggattcacct ttagaagtta tggc                                     24

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

Gly Phe Thr Phe Arg Ser Tyr Gly
1               5

<210> SEQ ID NO 101
<211> LENGTH: 24
<212> TYPE: DNA
<213> ORGANISM: Artificial Sequence
<220> FEATURE:
<223> OTHER INFORMATION: synthetic

<400> SEQUENCE: 101
atctggtatg atggaagtaa taaa                                     24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile Trp Tyr Asp Gly Ser Asn Lys
1               5

<210> SEQ ID NO 103
<211> LENGTH: 45
<212> TYPE: DNA
<213> ORGANISM: Artificial Sequence
<220> FEATURE:
<223> OTHER INFORMATION: synthetic -continued

<400> SEQUENCE: 103
gcgatagaca aatgggctac ggtgactacg tacctgtttg actac                     45

<210> SEQ ID NO 104
<211> LENGTH: 15
<212> TYPE: PRT
<213> ORGANISM: Artificial Sequence
<220> FEATURE:
<223> OTHER INFORMATION: synthetic

<400> SEQUENCE: 104

Ala Ile Asp Lys Trp Ala Thr Val Thr Thr Tyr Leu Phe Asp Tyr
1               5                   10                  15

<210> SEQ ID NO 105
<211> LENGTH: 363
<212> TYPE: DNA
<213> ORGANISM: Artificial Sequence
<220> FEATURE:
<223> OTHER INFORMATION: synthetic

<400> SEQUENCE: 105
gaggtgcagc tggtggagtc tgggggaggc ttggtacagt ctggagggtc cctgagactc     60
tcttgtgcag cctctggatt caccttcagt cgttatgaaa tgaactgggt ccgccaggct    120
ccagggaagg ggctggagtg ggttgcatat attagtaata ctggtactac cagggactat    180
tcagactctg tgaagggccg attcaccatc tccagagaca acgccaagaa ctcactatat    240
ctacaaatga gcagcctgag agtcgaggac acggctgttt attattgtgt gagagagaaa    300
tttagtggga cctctgactg gttcgacccc tggggccagg aaccctggt caccgtctcc    360 tca                                                                  363

<210> SEQ ID NO 106
<211> LENGTH: 121
<212> TYPE: PRT
<213> ORGANISM: Artificial Sequence
<220> FEATURE:
<223> OTHER INFORMATION: synthetic

<400> SEQUENCE: 106

Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Thr Phe Ser Arg Tyr
                20                  25                  30

Glu Met Asn Trp Val Arg Gln Ala Pro Gly Lys Gly Leu Glu Trp Val
            35                  40                  45

Ala Tyr Ile Ser Asn Thr Gly Thr Thr Arg Asp Tyr Ser Asp Ser Val
        50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Val Glu Asp Thr Ala Val Tyr Tyr Cys
                85                  90                  95

Val Arg Glu Lys Phe Ser Gly Thr Ser Asp Trp Phe Asp Pro Trp Gly
            100                 105                 110

Gln Gly Thr Leu Val Thr Val Ser Ser
        115                 120

<210> SEQ ID NO 107
<211> LENGTH: 24

```
<212> TYPE: DNA
<213> ORGANISM: Artificial Sequence
<220> FEATURE:
<223> OTHER INFORMATION: synthetic

<400> SEQUENCE: 107
ggattcacct tcagtcgtta tgaa                                              24

<210> SEQ ID NO 108
<211> LENGTH: 8
<212> TYPE: PRT
<213> ORGANISM: Artificial Sequence
<220> FEATURE:
<223> OTHER INFORMATION: synthetic

<400> SEQUENCE: 108

Gly Phe Thr Phe Ser Arg Tyr Glu
1               5

<210> SEQ ID NO 109
<211> LENGTH: 24
<212> TYPE: DNA
<213> ORGANISM: Artificial Sequence
<220> FEATURE:
<223> OTHER INFORMATION: synthetic

<400> SEQUENCE: 109
attagtaata ctggtactac cagg                                              24

<210> SEQ ID NO 110
<211> LENGTH: 8
<212> TYPE: PRT
<213> ORGANISM: Artificial Sequence
<220> FEATURE:
<223> OTHER INFORMATION: synthetic

<400> SEQUENCE: 110

Ile Ser Asn Thr Gly Thr Thr Arg
1               5

<210> SEQ ID NO 111
<211> LENGTH: 42
<212> TYPE: DNA
<213> ORGANISM: Artificial Sequence
<220> FEATURE:
<223> OTHER INFORMATION: synthetic

<400> SEQUENCE: 111
gtgagagaga aatttagtgg gacctctgac tggttcgacc cc                          42

<210> SEQ ID NO 112
<211> LENGTH: 14
<212> TYPE: PRT
<213> ORGANISM: Artificial Sequence
<220> FEATURE:
<223> OTHER INFORMATION: synthetic

<400> SEQUENCE: 112

Val Arg Glu Lys Phe Ser Gly Thr Ser Asp Trp Phe Asp Pro
1               5                   10

<210> SEQ ID NO 113
<211> LENGTH: 375
<212> TYPE: DNA
<213> ORGANISM: Artificial Sequence
<220> FEATURE:
<223> OTHER INFORMATION: synthetic
```

-continued

<400> SEQUENCE: 113

```
gaggtgcagc tggtggagtc tgggggaggc ttggtgcagc ctggggggtc cctgagactc      60
tcctgtgcag cctctggatt cacctttagt agctatgcca tgaactgggt ccgccaggct     120
ccagggaagg ggctggaatg ggtctcagct attagtggta gtggtgatag cacatactac     180
acagactccg tgaagggccg gttcaccatc tccagagaca attccaagaa cacgctgtat     240
ctgcaaatga acaccctgag agccgaggac acggccgtat attactgtgc gaaagaggag     300
attgttatgt tggtaggtgc taccccgggg tggttcgacc cctggggcca gggaaccctg     360
gtcaccgtct cctca                                                     375
```

<210> SEQ ID NO 114
<211> LENGTH: 125
<212> TYPE: PRT
<213> ORGANISM: Artificial Sequence
<220> FEATURE:
<223> OTHER INFORMATION: synthetic

<400> SEQUENCE: 114

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Asp Ser Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys
                85                  90                  95

Ala Lys Glu Glu Ile Val Met Leu Val Gly Ala Thr Pro Gly Trp Phe
            100                 105                 110

Asp Pro Trp Gly Gln Gly Thr Leu Val Thr Val Ser Ser
        115                 120                 125
```

<210> SEQ ID NO 115
<211> LENGTH: 24
<212> TYPE: DNA
<213> ORGANISM: Artificial Sequence
<220> FEATURE:
<223> OTHER INFORMATION: synthetic

<400> SEQUENCE: 115

```
ggattcacct ttagtagcta tgcc                                            24
```

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

```
Gly Phe Thr Phe Ser Ser Tyr Ala
1               5
```

<210> SEQ ID NO 117
<211> LENGTH: 24

```
<212> TYPE: DNA
<213> ORGANISM: Artificial Sequence
<220> FEATURE:
<223> OTHER INFORMATION: synthetic

<400> SEQUENCE: 117
attagtggta gtggtgatag caca                                           24

<210> SEQ ID NO 118
<211> LENGTH: 8
<212> TYPE: PRT
<213> ORGANISM: Artificial Sequence
<220> FEATURE:
<223> OTHER INFORMATION: synthetic

<400> SEQUENCE: 118

Ile Ser Gly Ser Gly Asp Ser Thr
1               5

<210> SEQ ID NO 119
<211> LENGTH: 54
<212> TYPE: DNA
<213> ORGANISM: Artificial Sequence
<220> FEATURE:
<223> OTHER INFORMATION: synthetic

<400> SEQUENCE: 119
gcgaaagagg agattgttat gttggtaggt gctaccccgg ggtggttcga cccc          54

<210> SEQ ID NO 120
<211> LENGTH: 18
<212> TYPE: PRT
<213> ORGANISM: Artificial Sequence
<220> FEATURE:
<223> OTHER INFORMATION: synthetic

<400> SEQUENCE: 120

Ala Lys Glu Glu Ile Val Met Leu Val Gly Ala Thr Pro Gly Trp Phe
1               5                   10                  15

Asp Pro

<210> SEQ ID NO 121
<211> LENGTH: 387
<212> TYPE: DNA
<213> ORGANISM: Artificial Sequence
<220> FEATURE:
<223> OTHER INFORMATION: synthetic

<400> SEQUENCE: 121
gaggtgcagc tggtgcagtc tggagcagag gtgaaaaagc ccggggagtc tctgaagatc    60
tcctgtaagg gttctggata cagttttacc agttactgga tcgactgggt gcgccagatg   120
cccgggaaag gcctggagtg gatggggatc atctatcctg atgactctga taccagatac   180
agtccgtcct tccaaggcca ggtcaccatg tcagtcgaca gtccatcag caccgcctac    240 ctgcagtgga gcagcctgaa ggcctcggac accgccatat attactgtgc gagacatgag   300
agaggtatag tagaagctgg tacggattac tactactact acggtatgga cgtctgggc    360 caagggacca cggtcaccgt ctcctca                                       387

<210> SEQ ID NO 122
<211> LENGTH: 129
<212> TYPE: PRT
<213> ORGANISM: Artificial Sequence
<220> FEATURE:
```

<223> OTHER INFORMATION: synthetic

<400> SEQUENCE: 122

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Asp Trp Val Arg Gln Met Pro Gly Lys Gly Leu Glu Trp Met
        35                  40                  45

Gly Ile Ile Tyr Pro Asp Asp Ser Asp Thr Arg Tyr Ser Pro Ser Phe
    50                  55                  60

Gln Gly Gln Val Thr Met Ser Val Asp Lys Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Arg His Glu Arg Gly Ile Val Glu Ala Gly Thr Asp Tyr Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 123
<211> LENGTH: 24
<212> TYPE: DNA
<213> ORGANISM: Artificial Sequence
<220> FEATURE:
<223> OTHER INFORMATION: synthetic

<400> SEQUENCE: 123
ggatacagtt ttaccagtta ctgg         24

<210> SEQ ID NO 124
<211> LENGTH: 8
<212> TYPE: PRT
<213> ORGANISM: Artificial Sequence
<220> FEATURE:
<223> OTHER INFORMATION: synthetic

<400> SEQUENCE: 124

Gly Tyr Ser Phe Thr Ser Tyr Trp
1               5

<210> SEQ ID NO 125
<211> LENGTH: 24
<212> TYPE: DNA
<213> ORGANISM: Artificial Sequence
<220> FEATURE:
<223> OTHER INFORMATION: synthetic

<400> SEQUENCE: 125
atctatcctg atgactctga tacc         24

<210> SEQ ID NO 126
<211> LENGTH: 8
<212> TYPE: PRT
<213> ORGANISM: Artificial Sequence
<220> FEATURE:
<223> OTHER INFORMATION: synthetic

<400> SEQUENCE: 126

Ile Tyr Pro Asp Asp Ser Asp Thr
1               5

```
<210> SEQ ID NO 127
<211> LENGTH: 66
<212> TYPE: DNA
<213> ORGANISM: Artificial Sequence
<220> FEATURE:
<223> OTHER INFORMATION: synthetic

<400> SEQUENCE: 127
gcgagacatg agagaggtat agtagaagct ggtacggatt actactacta ctacggtatg    60
gacgtc                                                               66

<210> SEQ ID NO 128
<211> LENGTH: 22
<212> TYPE: PRT
<213> ORGANISM: Artificial Sequence
<220> FEATURE:
<223> OTHER INFORMATION: synthetic

<400> SEQUENCE: 128

Ala Arg His Glu Arg Gly Ile Val Glu Ala Gly Thr Asp Tyr Tyr Tyr
1               5                   10                  15

Tyr Tyr Gly Met Asp Val
            20

<210> SEQ ID NO 129
<211> LENGTH: 357
<212> TYPE: DNA
<213> ORGANISM: Artificial Sequence
<220> FEATURE:
<223> OTHER INFORMATION: synthetic

<400> SEQUENCE: 129
caggttcagc tggtgcagtc tggagctgag gtgatgaagc ctggggcctc agtgaaggtc    60
tcctgcaggg cttctggtta cacctttagc agctatgata tcaactgggt gcgacaggcc   120
cctggacaag gacttgagtg gatgggatgg atcagcactg ccactggtaa cacaaactat   180
ccacagaagg tccagggcag agtcaccatg accacagaca catcaacgaa cacagcctac   240
atggagctga ggagcctgag atctgacgac acggccgtat attattgtac gagagagggc   300
aattcgaagg gctggctcga cccctggggc cagggaaccc tggtcaccgt ctcctca      357

<210> SEQ ID NO 130
<211> LENGTH: 119
<212> TYPE: PRT
<213> ORGANISM: Artificial Sequence
<220> FEATURE:
<223> OTHER INFORMATION: synthetic

<400> SEQUENCE: 130

Gln Val Gln Leu Val Gln Ser Gly Ala Glu Val Met Lys Pro Gly Ala
1               5                   10                  15

Ser Val Lys Val Ser Cys Arg Ala Ser Gly Tyr Thr Phe Ser Ser Tyr
            20                  25                  30

Asp Ile Asn Trp Val Arg Gln Ala Pro Gly Gln Gly Leu Glu Trp Met
        35                  40                  45

Gly Trp Ile Ser Thr Ala Thr Gly Asn Thr Asn Tyr Pro Gln Lys Val
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
```

```
                85                  90                  95
Thr Arg Glu Gly Asn Ser Lys Gly Trp Leu Asp Pro Trp Gly Gln Gly
            100                 105                 110
Thr Leu Val Thr Val Ser Ser
        115

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131
ggttacacct ttagcagcta tgat                                          24

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

Gly Tyr Thr Phe Ser Ser Tyr Asp
1               5

<210> SEQ ID NO 133
<211> LENGTH: 24
<212> TYPE: DNA
<213> ORGANISM: Artificial Sequence
<220> FEATURE:
<223> OTHER INFORMATION: synthetic

<400> SEQUENCE: 133
atcagcactg ccactggtaa caca                                          24

<210> SEQ ID NO 134
<211> LENGTH: 8
<212> TYPE: PRT
<213> ORGANISM: Artificial Sequence
<220> FEATURE:
<223> OTHER INFORMATION: synthetic

<400> SEQUENCE: 134

Ile Ser Thr Ala Thr Gly Asn Thr
1               5

<210> SEQ ID NO 135
<211> LENGTH: 36
<212> TYPE: DNA
<213> ORGANISM: Artificial Sequence
<220> FEATURE:
<223> OTHER INFORMATION: synthetic

<400> SEQUENCE: 135
acgagagagg gcaattcgaa gggctggctc gacccc                             36

<210> SEQ ID NO 136
<211> LENGTH: 12
<212> TYPE: PRT
<213> ORGANISM: Artificial Sequence
<220> FEATURE:
<223> OTHER INFORMATION: synthetic

<400> SEQUENCE: 136
```

Thr Arg Glu Gly Asn Ser Lys Gly Trp Leu Asp Pro
1               5                   10

<210> SEQ ID NO 137
<211> LENGTH: 363
<212> TYPE: DNA
<213> ORGANISM: Artificial Sequence
<220> FEATURE:
<223> OTHER INFORMATION: synthetic

<400> SEQUENCE: 137
caggtacagc tgcagcagtc aggtcccgga caaatgaagt cctcgcagac cctcacactc     60
acctgtgcca tctccgggga cagtgtctct agcaacagtg ctatttggta ctggatcagg    120
cagtccccat cgagaggcct tgagtggctg gggaggacaa agttcaggtc caaatggtat    180
aatgattttg cactatctat gaaaagtcga ataaccatca cccagacac atccaagaac    240 cagttctccc tgcacctgaa ctctgtgact cccgaggaca cggctgtata ttactgtgca    300
agatataagt gggaactta ctttgactac tggggccagg gaaccctggt caccgtctcc    360
tca                                                                 363

<210> SEQ ID NO 138
<211> LENGTH: 121
<212> TYPE: PRT
<213> ORGANISM: Artificial Sequence
<220> FEATURE:
<223> OTHER INFORMATION: synthetic

<400> SEQUENCE: 138

Gln Val Gln Leu Gln Gln Ser Gly Pro Gly Gln Met Lys Ser Ser Gln
1               5                   10                  15

Thr Leu Thr Leu Thr Cys Ala Ile Ser Gly Asp Ser Val Ser Ser Asn
            20                  25                  30

Ser Ala Ile Trp Tyr Trp Ile Arg Gln Ser Pro Ser Arg Gly Leu Glu
        35                  40                  45

Trp Leu Gly Arg Thr Lys Phe Arg Ser Lys Trp Tyr Asn Asp Phe Ala
    50                  55                  60

Leu Ser Met Lys Ser Arg Ile Thr Ile Asn Pro Asp Thr Ser Lys Asn
65                  70                  75                  80

Gln Phe Ser Leu His Leu Asn Ser Val Thr Pro Glu Asp Thr Ala Val
                85                  90                  95

Tyr Tyr Cys Ala Arg Tyr Lys Trp Glu Leu Tyr Phe Asp Tyr Trp Gly
            100                 105                 110

Gln Gly Thr Leu Val Thr Val Ser Ser
        115                 120

<210> SEQ ID NO 139
<211> LENGTH: 30
<212> TYPE: DNA
<213> ORGANISM: Artificial Sequence
<220> FEATURE:
<223> OTHER INFORMATION: synthetic

<400> SEQUENCE: 139
ggggacagtg tctctagcaa cagtgctatt                                     30

<210> SEQ ID NO 140
<211> LENGTH: 10
<212> TYPE: PRT
<213> ORGANISM: Artificial Sequence
<220> FEATURE:
<223> OTHER INFORMATION: synthetic

<400> SEQUENCE: 140

Gly Asp Ser Val Ser Ser Asn Ser Ala Ile
1               5                   10

<210> SEQ ID NO 141
<211> LENGTH: 27
<212> TYPE: DNA
<213> ORGANISM: Artificial Sequence
<220> FEATURE:
<223> OTHER INFORMATION: synthetic

<400> SEQUENCE: 141
acaaagttca ggtccaaatg gtataat                                        27

<210> SEQ ID NO 142
<211> LENGTH: 9
<212> TYPE: PRT
<213> ORGANISM: Artificial Sequence
<220> FEATURE:
<223> OTHER INFORMATION: synthetic

<400> SEQUENCE: 142

Thr Lys Phe Arg Ser Lys Trp Tyr Asn
1               5

<210> SEQ ID NO 143
<211> LENGTH: 33
<212> TYPE: DNA
<213> ORGANISM: Artificial Sequence
<220> FEATURE:
<223> OTHER INFORMATION: synthetic

<400> SEQUENCE: 143
gcaagatata agtgggaact ttactttgac tac                                 33

<210> SEQ ID NO 144
<211> LENGTH: 11
<212> TYPE: PRT
<213> ORGANISM: Artificial Sequence
<220> FEATURE:
<223> OTHER INFORMATION: synthetic

<400> SEQUENCE: 144

Ala Arg Tyr Lys Trp Glu Leu Tyr Phe Asp Tyr
1               5                   10

<210> SEQ ID NO 145
<211> LENGTH: 354
<212> TYPE: DNA
<213> ORGANISM: Artificial Sequence
<220> FEATURE:
<223> OTHER INFORMATION: synthetic

<400> SEQUENCE: 145
gaggtgcagc tggtggagtc tgggggaggc ttggtccagc ctggggggtc cctgagactc     60
tcctgtgcag cctctggatt caccttagt acctattgga tgaactgggt ccgccaggct    120
ccagggaagg ggctggagtg ggtggccaac ataaaggaag atggaagtga aaatactat    180 gtggactctg tgaagggccg attcaccatc tccagagaca acgccaagaa ctcactgtat    240
ctgcaaatga acagcctgag agccgaggac acggctgtgt attactgtgc gagagagggt    300
tttggagtgg ttacctatat ctgggggccaa gggacaatgg tcaccgtctc ttca         354

```
<210> SEQ ID NO 146
<211> LENGTH: 118
<212> TYPE: PRT
<213> ORGANISM: Artificial Sequence
<220> FEATURE:
<223> OTHER INFORMATION: synthetic

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Trp Met Asn Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Phe Gly Val Val Thr Tyr Ile Trp Gly Gln Gly Thr
            100                 105                 110

Met Val Thr Val Ser Ser
        115

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147
ggattcacct ttagtaccta ttgg                                              24

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

Gly Phe Thr Phe Ser Thr Tyr Trp
1               5

<210> SEQ ID NO 149
<211> LENGTH: 24
<212> TYPE: DNA
<213> ORGANISM: Artificial Sequence
<220> FEATURE:
<223> OTHER INFORMATION: synthetic

<400> SEQUENCE: 149
ataaaggaag atggaagtga gaaa                                              24

<210> SEQ ID NO 150
<211> LENGTH: 8
<212> TYPE: PRT
<213> ORGANISM: Artificial Sequence
<220> FEATURE:
<223> OTHER INFORMATION: synthetic
```

<400> SEQUENCE: 150

Ile Lys Glu Asp Gly Ser Glu Lys
1               5

<210> SEQ ID NO 151
<211> LENGTH: 33
<212> TYPE: DNA
<213> ORGANISM: Artificial Sequence
<220> FEATURE:
<223> OTHER INFORMATION: synthetic

<400> SEQUENCE: 151
gcgagagagg gttttggagt ggttacctat atc                                  33

<210> SEQ ID NO 152
<211> LENGTH: 11
<212> TYPE: PRT
<213> ORGANISM: Artificial Sequence
<220> FEATURE:
<223> OTHER INFORMATION: synthetic

<400> SEQUENCE: 152

Ala Arg Glu Gly Phe Gly Val Val Thr Tyr Ile
1               5                   10

<210> SEQ ID NO 153
<211> LENGTH: 351
<212> TYPE: DNA
<213> ORGANISM: Artificial Sequence
<220> FEATURE:
<223> OTHER INFORMATION: synthetic

<400> SEQUENCE: 153
caggtgcagc tggtggagtc tgggggaggc ttggtcaagc ctggagggtc cctgagactc      60
tcctgtgcag cctctggatt caccttcagt gactactata tgacctggat ccgccagact     120
ccagggaagg ggctggattg ggtttcatac attagttcta gtggtactaa caaatacaac     180
gcagactctg tgaagggccg attcaccatc tccagggaca acgccaagaa ctcactgtat     240
ctgcaaatga acagcctgcg agccgaggac acggccgtat attactgtgt gagagacccc     300
ccctggggta tggacgtctg gggccaaggg accacggtca ccgtctcctc a              351

<210> SEQ ID NO 154
<211> LENGTH: 117
<212> TYPE: PRT
<213> ORGANISM: Artificial Sequence
<220> FEATURE:
<223> OTHER INFORMATION: synthetic

<400> SEQUENCE: 154

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Thr Pro Gly Lys Gly Leu Asp Trp Val
        35                  40                  45

Ser Tyr Ile Ser Ser Ser Gly Thr Asn Lys Tyr Asn Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys

```
                85                  90                  95
Val Arg Asp Pro Pro Trp Gly Met Asp Val Trp Gly Gln Gly Thr Thr
            100                 105                 110

Val Thr Val Ser Ser
        115

<210> SEQ ID NO 155
<211> LENGTH: 24
<212> TYPE: DNA
<213> ORGANISM: Artificial Sequence
<220> FEATURE:
<223> OTHER INFORMATION: synthetic

<400> SEQUENCE: 155
ggattcacct tcagtgacta ctat                                          24

<210> SEQ ID NO 156
<211> LENGTH: 8
<212> TYPE: PRT
<213> ORGANISM: Artificial Sequence
<220> FEATURE:
<223> OTHER INFORMATION: synthetic

<400> SEQUENCE: 156

Gly Phe Thr Phe Ser Asp Tyr Tyr
1               5

<210> SEQ ID NO 157
<211> LENGTH: 24
<212> TYPE: DNA
<213> ORGANISM: Artificial Sequence
<220> FEATURE:
<223> OTHER INFORMATION: synthetic

<400> SEQUENCE: 157
attagttcta gtggtactaa caaa                                          24

<210> SEQ ID NO 158
<211> LENGTH: 8
<212> TYPE: PRT
<213> ORGANISM: Artificial Sequence
<220> FEATURE:
<223> OTHER INFORMATION: synthetic

<400> SEQUENCE: 158

Ile Ser Ser Ser Gly Thr Asn Lys
1               5

<210> SEQ ID NO 159
<211> LENGTH: 30
<212> TYPE: DNA
<213> ORGANISM: Artificial Sequence
<220> FEATURE:
<223> OTHER INFORMATION: synthetic

<400> SEQUENCE: 159
gtgagagacc ccccctgggg tatggacgtc                                    30

<210> SEQ ID NO 160
<211> LENGTH: 10
<212> TYPE: PRT
<213> ORGANISM: Artificial Sequence
<220> FEATURE:
<223> OTHER INFORMATION: synthetic

<400> SEQUENCE: 160
```

```
Val Arg Asp Pro Pro Trp Gly Met Asp Val
1               5                   10
```

<210> SEQ ID NO 161
<211> LENGTH: 360
<212> TYPE: DNA
<213> ORGANISM: Artificial Sequence
<220> FEATURE:
<223> OTHER INFORMATION: synthetic

<400> SEQUENCE: 161

```
gaggtgcagc tggtggagtc tgggggaggc ttggtacagc ctgggggtc cctgagactc      60 tcctgtgttg cctctggatt caccttcaat aaatacgaca tgcactgggt ccgccaaact     120
actggaaaag gtctagagtg ggtctcaggt attgatactg atggtgacac atactatcca    180
ggctccgtga agggccgatt caccatctcc agagaaaatg ccgagaactc cctgtatctt    240
caaatgaacg gcctgagagt cggggacacg gctgtgtatt actgtgcaag atggccttgg    300
agtggtttct atggtgcttt tgatatctgg ggccaaggga caatggtcac cgtctcttca    360
```

<210> SEQ ID NO 162
<211> LENGTH: 120
<212> TYPE: PRT
<213> ORGANISM: Artificial Sequence
<220> FEATURE:
<223> OTHER INFORMATION: synthetic

<400> SEQUENCE: 162

```
Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Asn Lys Tyr
            20                  25                  30

Asp Met His Trp Val Arg Gln Thr Thr Gly Lys Gly Leu Glu Trp Val
        35                  40                  45

Ser Gly Ile Asp Thr Asp Gly Asp Thr Tyr Tyr Pro Gly Ser Val Lys
    50                  55                  60

Gly Arg Phe Thr Ile Ser Arg Glu Asn Ala Glu Asn Ser Leu Tyr Leu
65                  70                  75                  80

Gln Met Asn Gly Leu Arg Val Gly Asp Thr Ala Val Tyr Tyr Cys Ala
                85                  90                  95

Arg Trp Pro Trp Ser Gly Phe Tyr Gly Ala Phe Asp Ile Trp Gly Gln
            100                 105                 110

Gly Thr Met Val Thr Val Ser Ser
        115                 120
```

<210> SEQ ID NO 163
<211> LENGTH: 24
<212> TYPE: DNA
<213> ORGANISM: Artificial Sequence
<220> FEATURE:
<223> OTHER INFORMATION: synthetic

<400> SEQUENCE: 163

```
ggattcacct tcaataaata cgac                                            24
```

<210> SEQ ID NO 164
<211> LENGTH: 8
<212> TYPE: PRT
<213> ORGANISM: Artificial Sequence
<220> FEATURE:
<223> OTHER INFORMATION: synthetic

<400> SEQUENCE: 164

Gly Phe Thr Phe Asn Lys Tyr Asp
1               5

<210> SEQ ID NO 165
<211> LENGTH: 21
<212> TYPE: DNA
<213> ORGANISM: Artificial Sequence
<220> FEATURE:
<223> OTHER INFORMATION: synthetic

<400> SEQUENCE: 165
attgatactg atggtgacac a                                          21

<210> SEQ ID NO 166
<211> LENGTH: 7
<212> TYPE: PRT
<213> ORGANISM: Artificial Sequence
<220> FEATURE:
<223> OTHER INFORMATION: synthetic

<400> SEQUENCE: 166

Ile Asp Thr Asp Gly Asp Thr
1               5

<210> SEQ ID NO 167
<211> LENGTH: 42
<212> TYPE: DNA
<213> ORGANISM: Artificial Sequence
<220> FEATURE:
<223> OTHER INFORMATION: synthetic

<400> SEQUENCE: 167
gcaagatggc cttggagtgg tttctatggt gcttttgata tc                   42

<210> SEQ ID NO 168
<211> LENGTH: 14
<212> TYPE: PRT
<213> ORGANISM: Artificial Sequence
<220> FEATURE:
<223> OTHER INFORMATION: synthetic

<400> SEQUENCE: 168

Ala Arg Trp Pro Trp Ser Gly Phe Tyr Gly Ala Phe Asp Ile
1               5                   10

<210> SEQ ID NO 169
<211> LENGTH: 372
<212> TYPE: DNA
<213> ORGANISM: Artificial Sequence
<220> FEATURE:
<223> OTHER INFORMATION: synthetic

<400> SEQUENCE: 169
caggtgcagc tgcaggagtc gggcccagga ctggtgaagc cttcacagac cctgtccctc    60
acctgcactg tctctggtgg ctccatcagc agcggtggtg actactggag ctggatccgc   120
cagctcccag ggaagggcct ggagtggatt gggtacatct attacagtgg gagcgcctac   180
tataatccgt ccctcaagag tcgaggtacc atatcaatag acacgtctaa gaaccagttc   240
tccctgaagc tgacctctgt gactgccgcg gacacggccg tatatttctg tgtgaaatta   300
cgatttttgg agtggttctt gggggcggg ttcggcccct ggggccaggg aaccctggtc   360
accgtctcct ca                                                      372

<210> SEQ ID NO 170
<211> LENGTH: 124
<212> TYPE: PRT
<213> ORGANISM: Artificial Sequence
<220> FEATURE:
<223> OTHER INFORMATION: synthetic

<400> SEQUENCE: 170

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Asp Tyr Trp Ser Trp Ile Arg Gln Leu Pro Gly Lys Gly Leu Glu
        35                  40                  45

Trp Ile Gly Tyr Ile Tyr Tyr Ser Gly Ser Ala Tyr Tyr Asn Pro Ser
    50                  55                  60

Leu Lys Ser Arg Gly Thr Ile Ser Ile Asp Thr Ser Lys Asn Gln Phe
65                  70                  75                  80

Ser Leu Lys Leu Thr Ser Val Thr Ala Ala Asp Thr Ala Val Tyr Phe
                85                  90                  95

Cys Val Lys Leu Arg Phe Leu Glu Trp Phe Leu Gly Gly Trp Phe Gly
            100                 105                 110

Pro Trp Gly Gln Gly Thr Leu Val Thr Val Ser Ser
        115                 120

<210> SEQ ID NO 171
<211> LENGTH: 30
<212> TYPE: DNA
<213> ORGANISM: Artificial Sequence
<220> FEATURE:
<223> OTHER INFORMATION: synthetic

<400> SEQUENCE: 171
ggtggctcca tcagcagcgg tggtgactac                                       30

<210> SEQ ID NO 172
<211> LENGTH: 10
<212> TYPE: PRT
<213> ORGANISM: Artificial Sequence
<220> FEATURE:
<223> OTHER INFORMATION: synthetic

<400> SEQUENCE: 172

Gly Gly Ser Ile Ser Ser Gly Gly Asp Tyr
1               5                   10

<210> SEQ ID NO 173
<211> LENGTH: 21
<212> TYPE: DNA
<213> ORGANISM: Artificial Sequence
<220> FEATURE:
<223> OTHER INFORMATION: synthetic

<400> SEQUENCE: 173
atctattaca gtgggagcgc c                                                21

<210> SEQ ID NO 174
<211> LENGTH: 7
<212> TYPE: PRT
<213> ORGANISM: Artificial Sequence
<220> FEATURE:
<223> OTHER INFORMATION: synthetic

```
<400> SEQUENCE: 174

Ile Tyr Tyr Ser Gly Ser Ala
1               5

<210> SEQ ID NO 175
<211> LENGTH: 48
<212> TYPE: DNA
<213> ORGANISM: Artificial Sequence
<220> FEATURE:
<223> OTHER INFORMATION: synthetic

<400> SEQUENCE: 175
gtgaaattac gatttttgga gtggttcttg gggggctggt tcggcccc                    48

<210> SEQ ID NO 176
<211> LENGTH: 16
<212> TYPE: PRT
<213> ORGANISM: Artificial Sequence
<220> FEATURE:
<223> OTHER INFORMATION: synthetic

<400> SEQUENCE: 176

Val Lys Leu Arg Phe Leu Glu Trp Phe Leu Gly Gly Trp Phe Gly Pro
1               5                   10                  15

<210> SEQ ID NO 177
<211> LENGTH: 351
<212> TYPE: DNA
<213> ORGANISM: Artificial Sequence
<220> FEATURE:
<223> OTHER INFORMATION: synthetic

<400> SEQUENCE: 177
gaggtgcagc tggtggagtc tgggggaggc ttggtacagc cggggggtc cctgagactc         60 tcctgtgcag cctctggatt cacctttagc aactatggca tgacctgggt ccgccaggct       120
ccagggaagg gcctggaatg ggtctcagct attactggtg gtggtggtag cacatactac       180
tcaaactccg tgaagggccg gttcaccatc tccagagaca attccaagaa cacggtgtat       240
ctgcgaatga acagtgtgag agccgaggac acggccgtat attactgtgc gaaatataag       300
tggaacttcg tggacgactg gggccaggga accacggtca ccgtctcctc a                351

<210> SEQ ID NO 178
<211> LENGTH: 117
<212> TYPE: PRT
<213> ORGANISM: Artificial Sequence
<220> FEATURE:
<223> OTHER INFORMATION: synthetic

<400> SEQUENCE: 178

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Gly Met Thr Trp Val Arg Gln Ala Pro Gly Lys Gly Leu Glu Trp Val
            35                  40                  45

Ser Ala Ile Thr Gly Gly Gly Gly Ser Thr Tyr Tyr Ser Asn Ser Val
        50                  55                  60

Lys Gly Arg Phe Thr Ile Ser Arg Asp Asn Ser Lys Asn Thr Val Tyr
65                  70                  75                  80

Leu Arg Met Asn Ser Val Arg Ala Glu Asp Thr Ala Val Tyr Tyr Cys
```

85                  90                  95
Ala Lys Tyr Lys Trp Asn Phe Val Asp Asp Trp Gly Gln Gly Thr Thr
            100                 105                 110

Val Thr Val Ser Ser
        115

<210> SEQ ID NO 179
<211> LENGTH: 24
<212> TYPE: DNA
<213> ORGANISM: Artificial Sequence
<220> FEATURE:
<223> OTHER INFORMATION: synthetic

<400> SEQUENCE: 179
ggattcacct ttagcaacta tggc                                           24

<210> SEQ ID NO 180
<211> LENGTH: 8
<212> TYPE: PRT
<213> ORGANISM: Artificial Sequence
<220> FEATURE:
<223> OTHER INFORMATION: synthetic

<400> SEQUENCE: 180

Gly Phe Thr Phe Ser Asn Tyr Gly
1               5

<210> SEQ ID NO 181
<211> LENGTH: 24
<212> TYPE: DNA
<213> ORGANISM: Artificial Sequence
<220> FEATURE:
<223> OTHER INFORMATION: synthetic

<400> SEQUENCE: 181
attactggtg gtggtggtag caca                                           24

<210> SEQ ID NO 182
<211> LENGTH: 8
<212> TYPE: PRT
<213> ORGANISM: Artificial Sequence
<220> FEATURE:
<223> OTHER INFORMATION: synthetic

<400> SEQUENCE: 182

Ile Thr Gly Gly Gly Gly Ser Thr
1               5

<210> SEQ ID NO 183
<211> LENGTH: 30
<212> TYPE: DNA
<213> ORGANISM: Artificial Sequence
<220> FEATURE:
<223> OTHER INFORMATION: synthetic

<400> SEQUENCE: 183
gcgaaatata agtggaactt cgtggacgac                                     30

<210> SEQ ID NO 184
<211> LENGTH: 10
<212> TYPE: PRT
<213> ORGANISM: Artificial Sequence
<220> FEATURE:
<223> OTHER INFORMATION: synthetic

<400> SEQUENCE: 184

```
Ala Lys Tyr Lys Trp Asn Phe Val Asp Asp
1               5                   10
```

<210> SEQ ID NO 185
<211> LENGTH: 918
<212> TYPE: PRT
<213> ORGANISM: Artificial Sequence
<220> FEATURE:
<223> OTHER INFORMATION: human GP130  UniProtKB - Q17RA0

<400> SEQUENCE: 185

```
Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
        50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350
```

```
Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
        370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
            435                 440                 445

Ser Val Lys Lys Tyr Ile Leu Glu Trp Cys Val Leu Ser Asp Lys Ala
        450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
        530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
        610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
        690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765
```

-continued

```
His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
        915
```

<210> SEQ ID NO 186
<211> LENGTH: 1165
<212> TYPE: PRT
<213> ORGANISM: Artificial Sequence
<220> FEATURE:
<223> OTHER INFORMATION: human LEPR (UniProtKB/Swiss-Prot Accession No. P48357)

<400> SEQUENCE: 186

```
Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205
```

```
Leu Leu Met Cys Leu Lys Ile Thr Ser Gly Val Ile Phe Gln Ser
    210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
                260                 265                 270

Tyr Ser Glu Asn Ser Thr Thr Val Ile Arg Glu Ala Asp Lys Ile Val
            275                 280                 285

Ser Ala Thr Ser Leu Leu Val Asp Ser Ile Leu Pro Gly Ser Ser Tyr
    290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
                340                 345                 350

Ile Tyr Lys Lys Glu Asn Lys Ile Val Pro Ser Lys Glu Ile Val Trp
            355                 360                 365

Trp Met Asn Leu Ala Glu Lys Ile Pro Gln Ser Gln Tyr Asp Val Val
    370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
                420                 425                 430

Asn Ile Ser Cys Glu Thr Asp Gly Tyr Leu Thr Lys Met Thr Cys Arg
            435                 440                 445

Trp Ser Thr Ser Thr Ile Gln Ser Leu Ala Glu Ser Thr Leu Gln Leu
    450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
                500                 505                 510

Ile Arg Ile Asn His Ser Leu Gly Ser Leu Asp Ser Pro Pro Thr Cys
            515                 520                 525

Val Leu Pro Asp Ser Val Val Lys Pro Leu Pro Pro Ser Ser Val Lys
    530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Cys Ala Val Tyr Ala
        595                 600                 605

Val Gln Val Arg Cys Lys Arg Leu Asp Gly Leu Gly Tyr Trp Ser Asn
    610                 615                 620
```

-continued

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
            645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
            675                 680                 685

Gly Thr Trp Ser Glu Asp Val Gly Asn His Thr Lys Phe Thr Phe Leu
690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
            725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
            755                 760                 765

Tyr Phe Ile Ile Glu Trp Lys Asn Leu Asn Glu Asp Gly Glu Ile Lys
770                 775                 780

Trp Leu Arg Ile Ser Ser Val Lys Lys Tyr Tyr Ile His Asp His Phe
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
835                 840                 845

Ile Ile Ser Ser Ser Ile Leu Leu Leu Gly Thr Leu Leu Ile Ser His
850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Pro Glu Thr Phe Glu
            885                 890                 895

His Leu Phe Ile Lys His Thr Ala Ser Val Thr Cys Gly Pro Leu Leu
            900                 905                 910

Leu Glu Pro Glu Thr Ile Ser Glu Asp Ile Ser Val Asp Thr Ser Trp
915                 920                 925

Lys Asn Lys Asp Glu Met Met Pro Thr Thr Val Val Ser Leu Leu Ser
930                 935                 940

Thr Thr Asp Leu Glu Lys Gly Ser Val Cys Ile Ser Asp Gln Phe Asn
945                 950                 955                 960

Ser Val Asn Phe Ser Glu Ala Glu Gly Thr Glu Val Thr Tyr Glu Asp
                965                 970                 975

Glu Ser Gln Arg Gln Pro Phe Val Lys Tyr Ala Thr Leu Ile Ser Asn
            980                 985                 990

Ser Lys Pro Ser Glu Thr Gly Glu Glu Gln Gly Leu Ile Asn Ser Ser
            995                 1000                1005

Val Thr Lys Cys Phe Ser Ser Lys Asn Ser Pro Leu Lys Asp Ser
        1010                1015                1020

Phe Ser Asn Ser Ser Trp Glu Ile Glu Ala Gln Ala Phe Phe Ile
        1025                1030                1035

Leu Ser Asp Gln His Pro Asn Ile Ile Ser Pro His Leu Thr Phe

```
                    1040                1045                1050

Ser Glu Gly Leu Asp Glu Leu Leu Lys Leu Gly Asn Phe Pro
    1055                1060                1065

Glu Glu Asn Asn Asp Lys Lys Ser Ile Tyr Tyr Leu Gly Val Thr
    1070                1075                1080

Ser Ile Lys Lys Arg Glu Ser Gly Val Leu Leu Thr Asp Lys Ser
    1085                1090                1095

Arg Val Ser Cys Pro Phe Pro Ala Pro Cys Leu Phe Thr Asp Ile
    1100                1105                1110

Arg Val Leu Gln Asp Ser Cys Ser His Phe Val Glu Asn Asn Ile
    1115                1120                1125

Asn Leu Gly Thr Ser Ser Lys Lys Thr Phe Ala Ser Tyr Met Pro
    1130                1135                1140

Gln Phe Gln Thr Cys Ser Thr Gln Thr His Lys Ile Met Glu Asn
    1145                1150                1155

Lys Met Cys Asp Leu Thr Val
    1160                1165

<210> SEQ ID NO 187
<211> LENGTH: 846
<212> TYPE: PRT
<213> ORGANISM: Artificial Sequence
<220> FEATURE:
<223> OTHER INFORMATION: hLEPR-MMH

<400> SEQUENCE: 187

Phe Asn Leu Ser Tyr Pro Ile Thr Pro Trp Arg Phe Lys Leu Ser Cys
1               5                   10                  15

Met Pro Pro Asn Ser Thr Tyr Asp Tyr Phe Leu Leu Pro Ala Gly Leu
                20                  25                  30

Ser Lys Asn Thr Ser Asn Ser Asn Gly His Tyr Glu Thr Ala Val Glu
            35                  40                  45

Pro Lys Phe Asn Ser Ser Gly Thr His Phe Ser Asn Leu Ser Lys Thr
        50                  55                  60

Thr Phe His Cys Cys Phe Arg Ser Glu Gln Asp Arg Asn Cys Ser Leu
65                  70                  75                  80

Cys Ala Asp Asn Ile Glu Gly Lys Thr Phe Val Ser Thr Val Asn Ser
                85                  90                  95

Leu Val Phe Gln Gln Ile Asp Ala Asn Trp Asn Ile Gln Cys Trp Leu
                100                 105                 110

Lys Gly Asp Leu Lys Leu Phe Ile Cys Tyr Val Glu Ser Leu Phe Lys
            115                 120                 125

Asn Leu Phe Arg Asn Tyr Asn Tyr Lys Val His Leu Leu Tyr Val Leu
        130                 135                 140

Pro Glu Val Leu Glu Asp Ser Pro Leu Val Pro Gln Lys Gly Ser Phe
145                 150                 155                 160

Gln Met Val His Cys Asn Cys Ser Val His Glu Cys Cys Glu Cys Leu
                165                 170                 175

Val Pro Val Pro Thr Ala Lys Leu Asn Asp Thr Leu Leu Met Cys Leu
                180                 185                 190

Lys Ile Thr Ser Gly Gly Val Ile Phe Gln Ser Pro Leu Met Ser Val
            195                 200                 205

Gln Pro Ile Asn Met Val Lys Pro Asp Pro Pro Leu Gly Leu His Met
        210                 215                 220

Glu Ile Thr Asp Asp Gly Asn Leu Lys Ile Ser Trp Ser Ser Pro Pro
```

```
            225                 230                 235                 240
Leu Val Pro Phe Pro Leu Gln Tyr Gln Val Lys Tyr Ser Glu Asn Ser
                245                 250                 255
Thr Thr Val Ile Arg Glu Ala Asp Lys Ile Val Ser Ala Thr Ser Leu
                260                 265                 270
Leu Val Asp Ser Ile Leu Pro Gly Ser Ser Tyr Glu Val Gln Val Arg
                275                 280                 285
Gly Lys Arg Leu Asp Gly Pro Gly Ile Trp Ser Asp Trp Ser Thr Pro
290                 295                 300
Arg Val Phe Thr Thr Gln Asp Val Ile Tyr Phe Pro Pro Lys Ile Leu
305                 310                 315                 320
Thr Ser Val Gly Ser Asn Val Ser Phe His Cys Ile Tyr Lys Lys Glu
                325                 330                 335
Asn Lys Ile Val Pro Ser Lys Glu Ile Val Trp Trp Met Asn Leu Ala
                340                 345                 350
Glu Lys Ile Pro Gln Ser Gln Tyr Asp Val Val Ser Asp His Val Ser
                355                 360                 365
Lys Val Thr Phe Phe Asn Leu Asn Glu Thr Lys Pro Arg Gly Lys Phe
                370                 375                 380
Thr Tyr Asp Ala Val Tyr Cys Cys Asn Glu His Glu Cys His His Arg
385                 390                 395                 400
Tyr Ala Glu Leu Tyr Val Ile Asp Val Asn Ile Asn Ile Ser Cys Glu
                405                 410                 415
Thr Asp Gly Tyr Leu Thr Lys Met Thr Cys Arg Trp Ser Thr Ser Thr
                420                 425                 430
Ile Gln Ser Leu Ala Glu Ser Thr Leu Gln Leu Arg Tyr His Arg Ser
                435                 440                 445
Ser Leu Tyr Cys Ser Asp Ile Pro Ser Ile His Pro Ile Ser Glu Pro
                450                 455                 460
Lys Asp Cys Tyr Leu Gln Ser Asp Gly Phe Tyr Glu Cys Ile Phe Gln
465                 470                 475                 480
Pro Ile Phe Leu Leu Ser Gly Tyr Thr Met Trp Ile Arg Ile Asn His
                485                 490                 495
Ser Leu Gly Ser Leu Asp Ser Pro Pro Thr Cys Val Leu Pro Asp Ser
                500                 505                 510
Val Val Lys Pro Leu Pro Pro Ser Ser Val Lys Ala Glu Ile Thr Ile
                515                 520                 525
Asn Ile Gly Leu Leu Lys Ile Ser Trp Glu Lys Pro Val Phe Pro Glu
                530                 535                 540
Asn Asn Leu Gln Phe Gln Ile Arg Tyr Gly Leu Ser Gly Lys Glu Val
545                 550                 555                 560
Gln Trp Lys Met Tyr Glu Val Tyr Asp Ala Lys Ser Lys Ser Val Ser
                565                 570                 575
Leu Pro Val Pro Asp Leu Cys Ala Val Tyr Ala Val Gln Val Arg Cys
                580                 585                 590
Lys Arg Leu Asp Gly Leu Gly Tyr Trp Ser Asn Trp Ser Asn Pro Ala
                595                 600                 605
Tyr Thr Val Val Met Asp Ile Lys Val Pro Met Arg Gly Pro Glu Phe
                610                 615                 620
Trp Arg Ile Ile Asn Gly Asp Thr Met Lys Lys Glu Lys Asn Val Thr
625                 630                 635                 640
Leu Leu Trp Lys Pro Leu Met Lys Asn Asp Ser Leu Cys Ser Val Gln
                645                 650                 655
```

```
Arg Tyr Val Ile Asn His His Thr Ser Cys Asn Gly Thr Trp Ser Glu
            660                 665                 670

Asp Val Gly Asn His Thr Lys Phe Thr Phe Leu Trp Thr Glu Gln Ala
            675                 680                 685

His Thr Val Thr Val Leu Ala Ile Asn Ser Ile Gly Ala Ser Val Ala
            690                 695                 700

Asn Phe Asn Leu Thr Phe Ser Trp Pro Met Ser Lys Val Asn Ile Val
705                 710                 715                 720

Gln Ser Leu Ser Ala Tyr Pro Leu Asn Ser Ser Cys Val Ile Val Ser
                725                 730                 735

Trp Ile Leu Ser Pro Ser Asp Tyr Lys Leu Met Tyr Phe Ile Ile Glu
            740                 745                 750

Trp Lys Asn Leu Asn Glu Asp Gly Glu Ile Lys Trp Leu Arg Ile Ser
            755                 760                 765

Ser Ser Val Lys Lys Tyr Tyr Ile His Asp His Phe Ile Pro Ile Glu
        770                 775                 780

Lys Tyr Gln Phe Ser Leu Tyr Pro Ile Phe Met Glu Gly Val Gly Lys
785                 790                 795                 800

Pro Lys Ile Ile Asn Ser Phe Thr Gln Asp Asp Ile Glu Lys His Gln
            805                 810                 815

Ser Asp Glu Gln Lys Leu Ile Ser Glu Glu Asp Leu Gly Gly Glu Gln
            820                 825                 830

Lys Leu Ile Ser Glu Glu Asp Leu His His His His His His
            835                 840                 845

<210> SEQ ID NO 188
<211> LENGTH: 844
<212> TYPE: PRT
<213> ORGANISM: Artificial Sequence
<220> FEATURE:
<223> OTHER INFORMATION: MfLEPR-MMH

<400> SEQUENCE: 188

Phe Asn Leu Ser Tyr Pro Ile Thr Pro Trp Arg Phe Lys Leu Ser Cys
1               5                   10                  15

Met Pro Pro Asn Ser Thr Tyr Asp Tyr Phe Leu Leu Pro Ala Gly Leu
            20                  25                  30

Ser Lys Asn Thr Ser Asn Leu Asn Gly His Tyr Glu Thr Ala Val Glu
            35                  40                  45

Phe Asn Ser Ser Asp Thr His Phe Ser Asn Leu Ser Lys Thr Thr Phe
50                  55                  60

His Cys Cys Phe Arg Ser Glu Gln Asp Arg Asn Cys Ser Leu Cys Ala
65                  70                  75                  80

Asp Asn Ile Glu Gly Lys Thr Phe Val Ser Thr Val Asn Ser Ser Val
            85                  90                  95

Phe Gln Gln Met Gly Ala Asn Trp Asn Ile Gln Cys Trp Leu Lys Gly
            100                 105                 110

Asp Leu Lys Leu Phe Ile Cys Tyr Val Glu Ser Leu Phe Lys Asn Pro
            115                 120                 125

Phe Lys Asn Tyr Lys His Lys Val His Leu Leu Tyr Val Leu Pro Glu
            130                 135                 140

Val Leu Glu Asp Ser Pro Leu Val Pro Gln Lys Gly Ser Phe Gln Met
145                 150                 155                 160

Val His Cys Asn Cys Ser Val His Glu Arg Cys Glu Cys Leu Val Pro
            165                 170                 175
```

```
Val Pro Thr Ala Lys Leu Asn Asp Thr Leu Met Cys Leu Lys Ile
            180                 185                 190

Thr Ser Gly Gly Val Ile Phe Gln Ser Pro Leu Met Ser Val Gln Pro
            195                 200                 205

Ile Asn Met Val Lys Pro Asp Pro Leu Gly Leu Arg Met Glu Ile
            210                 215                 220

Thr Asp Asp Gly Asn Leu Lys Ile Ser Trp Ser Ser Pro Leu Val
225                 230                 235                 240

Pro Phe Pro Leu Gln Tyr Glu Val Lys Tyr Ser Glu Asn Ser Thr Thr
                245                 250                 255

Val Ile Arg Glu Ala Asp Lys Ile Val Ser Ala Thr Ser Leu Leu Val
            260                 265                 270

Asp Gly Ile Leu Pro Gly Ser Ser Tyr Glu Val Gln Val Arg Gly Lys
            275                 280                 285

Arg Leu Asp Gly Pro Gly Ile Trp Ser Asp Trp Ser Thr Pro His Val
            290                 295                 300

Phe Thr Thr Gln Asp Val Ile Tyr Phe Pro Pro Lys Ile Leu Thr Ser
305                 310                 315                 320

Val Gly Ser Asn Val Ser Phe His Cys Ile Tyr Lys Asn Glu Asn Lys
            325                 330                 335

Ile Val Ser Ser Lys Lys Ile Val Trp Trp Met Asn Leu Ala Glu Lys
            340                 345                 350

Ile Pro Gln Ser Gln Tyr Asp Val Val Ser Asp His Val Ser Lys Val
            355                 360                 365

Thr Phe Phe Asn Leu Asn Glu Thr Lys Pro Arg Gly Lys Phe Thr Tyr
            370                 375                 380

Asp Ala Val Tyr Cys Cys Asn Glu His Glu Cys His His Arg Tyr Ala
385                 390                 395                 400

Glu Leu Tyr Val Ile Asp Val Asn Ile Asn Ile Ser Cys Glu Thr Asp
                405                 410                 415

Gly His Leu Thr Lys Met Thr Cys Arg Trp Ser Thr Asn Thr Ile Gln
            420                 425                 430

Ser Leu Ala Gly Ser Thr Leu Gln Leu Arg Tyr Arg Arg Ser Ser Leu
            435                 440                 445

Tyr Cys Phe Asp Ile Pro Ser Ile His Pro Ile Ser Lys Pro Lys Asp
            450                 455                 460

Cys Tyr Leu Gln Ser Asp Gly Phe Tyr Glu Cys Val Phe Gln Pro Ile
465                 470                 475                 480

Phe Leu Leu Ser Gly Tyr Thr Met Trp Ile Arg Ile Asn His Pro Leu
                485                 490                 495

Gly Ser Leu Asp Ser Pro Pro Thr Cys Val Leu Pro Asp Ser Val Val
            500                 505                 510

Lys Pro Leu Pro Pro Ser Ser Val Lys Ala Glu Ile Ile Lys Asn Ile
            515                 520                 525

Gly Leu Leu Lys Ile Ser Trp Glu Lys Pro Val Phe Pro Glu Asn Asn
            530                 535                 540

Leu Gln Phe Gln Ile Arg Tyr Gly Leu Ser Gly Lys Glu Ile Gln Trp
545                 550                 555                 560

Lys Met Tyr Asp Val Tyr Asp Ala Lys Ser Lys Ser Val Ser Leu Pro
                565                 570                 575

Val Pro Asp Phe Cys Ala Val Tyr Ala Val Gln Val Arg Cys Lys Arg
            580                 585                 590
```

Ser Asp Gly Leu Gly Leu Trp Ser Asn Trp Ser Asn Pro Ala Tyr Thr
                595                 600                 605

Val Val Met Asp Ile Lys Val Pro Met Arg Gly Pro Glu Phe Trp Arg
            610                 615                 620

Ile Ile Asn Gly Asp Thr Met Lys Lys Glu Lys Asn Val Thr Leu Leu
625                 630                 635                 640

Trp Lys Pro Leu Met Lys Asn Asp Ser Leu Cys Ser Val Gln Arg Tyr
                645                 650                 655

Val Ile Asn His His Thr Ser Cys Asn Gly Thr Trp Ser Glu Asp Val
            660                 665                 670

Gly Asn His Thr Lys Phe Thr Phe Leu Trp Thr Glu Gln Ala His Thr
675                 680                 685

Val Thr Val Leu Ala Ile Asn Ser Ile Gly Ala Ser Val Ala Asn Phe
            690                 695                 700

Asn Leu Thr Phe Ser Trp Pro Met Ser Lys Val Asn Ile Val Gln Ser
705                 710                 715                 720

Leu Ser Ala Tyr Pro Leu Asn Ser Ser Cys Val Ile Leu Ser Trp Ile
                725                 730                 735

Leu Ser Pro Ser Asp Tyr Lys Leu Met Tyr Phe Ile Ile Glu Trp Lys
            740                 745                 750

Asn Leu Asn Glu Asp Gly Glu Ile Lys Trp Leu Arg Ile Ser Ser Ser
                755                 760                 765

Val Lys Lys Tyr Tyr Ile His Asp His Phe Ile Pro Ile Glu Lys Tyr
770                 775                 780

Gln Phe Ser Leu Tyr Pro Ile Phe Met Glu Gly Val Gly Lys Pro Lys
785                 790                 795                 800

Ile Ile Asn Ser Phe Ala Gln Asp Asn Thr Glu Lys His Gln Asn Asp
                805                 810                 815

Glu Gln Lys Leu Ile Ser Glu Glu Asp Leu Gly Gly Glu Gln Lys Leu
            820                 825                 830

Ile Ser Glu Glu Asp Leu His His His His His
            835                 840

<210> SEQ ID NO 189
<211> LENGTH: 1045
<212> TYPE: PRT
<213> ORGANISM: Artificial Sequence
<220> FEATURE:
<223> OTHER INFORMATION: hLEPR-hFc

<400> SEQUENCE: 189

Phe Asn Leu Ser Tyr Pro Ile Thr Pro Trp Arg Phe Lys Leu Ser Cys
1               5                   10                  15

Met Pro Pro Asn Ser Thr Tyr Asp Tyr Phe Leu Leu Pro Ala Gly Leu
            20                  25                  30

Ser Lys Asn Thr Ser Asn Ser Asn Gly His Tyr Glu Thr Ala Val Glu
        35                  40                  45

Pro Lys Phe Asn Ser Ser Gly Thr His Phe Ser Asn Leu Ser Lys Thr
    50                  55                  60

Thr Phe His Cys Cys Phe Arg Ser Glu Gln Asp Arg Asn Cys Ser Leu
65                  70                  75                  80

Cys Ala Asp Asn Ile Glu Gly Lys Thr Phe Val Ser Thr Val Asn Ser
                85                  90                  95

Leu Val Phe Gln Gln Ile Asp Ala Asn Trp Asn Ile Gln Cys Trp Leu
            100                 105                 110

```
Lys Gly Asp Leu Lys Leu Phe Ile Cys Tyr Val Glu Ser Leu Phe Lys
            115                 120                 125

Asn Leu Phe Arg Asn Tyr Asn Tyr Lys Val His Leu Leu Tyr Val Leu
        130                 135                 140

Pro Glu Val Leu Glu Asp Ser Pro Leu Val Pro Gln Lys Gly Ser Phe
145                 150                 155                 160

Gln Met Val His Cys Asn Cys Ser Val His Glu Cys Cys Glu Cys Leu
                165                 170                 175

Val Pro Val Pro Thr Ala Lys Leu Asn Asp Thr Leu Leu Met Cys Leu
            180                 185                 190

Lys Ile Thr Ser Gly Gly Val Ile Phe Gln Ser Pro Leu Met Ser Val
        195                 200                 205

Gln Pro Ile Asn Met Val Lys Pro Asp Pro Leu Gly Leu His Met
210                 215                 220

Glu Ile Thr Asp Asp Gly Asn Leu Lys Ile Ser Trp Ser Ser Pro Pro
225                 230                 235                 240

Leu Val Pro Phe Pro Leu Gln Tyr Gln Val Lys Tyr Ser Glu Asn Ser
                245                 250                 255

Thr Thr Val Ile Arg Glu Ala Asp Lys Ile Val Ser Ala Thr Ser Leu
            260                 265                 270

Leu Val Asp Ser Ile Leu Pro Gly Ser Ser Tyr Glu Val Gln Val Arg
        275                 280                 285

Gly Lys Arg Leu Asp Gly Pro Gly Ile Trp Ser Asp Trp Ser Thr Pro
    290                 295                 300

Arg Val Phe Thr Thr Gln Asp Val Ile Tyr Phe Pro Pro Lys Ile Leu
305                 310                 315                 320

Thr Ser Val Gly Ser Asn Val Ser Phe His Cys Ile Tyr Lys Lys Glu
                325                 330                 335

Asn Lys Ile Val Pro Ser Lys Glu Ile Val Trp Trp Met Asn Leu Ala
            340                 345                 350

Glu Lys Ile Pro Gln Ser Gln Tyr Asp Val Val Ser Asp His Val Ser
        355                 360                 365

Lys Val Thr Phe Phe Asn Leu Asn Glu Thr Lys Pro Arg Gly Lys Phe
    370                 375                 380

Thr Tyr Asp Ala Val Tyr Cys Cys Asn Glu His Glu Cys His His Arg
385                 390                 395                 400

Tyr Ala Glu Leu Tyr Val Ile Asp Val Asn Ile Asn Ile Ser Cys Glu
                405                 410                 415

Thr Asp Gly Tyr Leu Thr Lys Met Thr Cys Arg Trp Ser Thr Ser Thr
            420                 425                 430

Ile Gln Ser Leu Ala Glu Ser Thr Leu Gln Leu Arg Tyr His Arg Ser
        435                 440                 445

Ser Leu Tyr Cys Ser Asp Ile Pro Ser Ile His Pro Ile Ser Glu Pro
    450                 455                 460

Lys Asp Cys Tyr Leu Gln Ser Asp Gly Phe Tyr Glu Cys Ile Phe Gln
465                 470                 475                 480

Pro Ile Phe Leu Leu Ser Gly Tyr Thr Met Trp Ile Arg Ile Asn His
                485                 490                 495

Ser Leu Gly Ser Leu Asp Ser Pro Thr Cys Val Leu Pro Asp Ser
            500                 505                 510

Val Val Lys Pro Leu Pro Pro Ser Ser Val Lys Ala Glu Ile Thr Ile
        515                 520                 525

Asn Ile Gly Leu Leu Lys Ile Ser Trp Glu Lys Pro Val Phe Pro Glu
```

-continued

```
                530             535             540
Asn Asn Leu Gln Phe Gln Ile Arg Tyr Gly Leu Ser Gly Lys Glu Val
545                 550                 555                 560

Gln Trp Lys Met Tyr Glu Val Tyr Asp Ala Lys Ser Lys Ser Val Ser
                565                 570                 575

Leu Pro Val Pro Asp Leu Cys Ala Val Tyr Ala Val Gln Val Arg Cys
                580                 585                 590

Lys Arg Leu Asp Gly Leu Gly Tyr Trp Ser Asn Trp Ser Asn Pro Ala
                595                 600                 605

Tyr Thr Val Val Met Asp Ile Lys Val Pro Met Arg Gly Pro Glu Phe
                610                 615                 620

Trp Arg Ile Ile Asn Gly Asp Thr Met Lys Lys Glu Lys Asn Val Thr
625                 630                 635                 640

Leu Leu Trp Lys Pro Leu Met Lys Asn Asp Ser Leu Cys Ser Val Gln
                645                 650                 655

Arg Tyr Val Ile Asn His His Thr Ser Cys Asn Gly Thr Trp Ser Glu
                660                 665                 670

Asp Val Gly Asn His Thr Lys Phe Thr Phe Leu Trp Thr Glu Gln Ala
                675                 680                 685

His Thr Val Thr Val Leu Ala Ile Asn Ser Ile Gly Ala Ser Val Ala
690                 695                 700

Asn Phe Asn Leu Thr Phe Ser Trp Pro Met Ser Lys Val Asn Ile Val
705                 710                 715                 720

Gln Ser Leu Ser Ala Tyr Pro Leu Asn Ser Ser Cys Val Ile Val Ser
                725                 730                 735

Trp Ile Leu Ser Pro Ser Asp Tyr Lys Leu Met Tyr Phe Ile Ile Glu
                740                 745                 750

Trp Lys Asn Leu Asn Glu Asp Gly Glu Ile Lys Trp Leu Arg Ile Ser
                755                 760                 765

Ser Ser Val Lys Lys Tyr Tyr Ile His Asp His Phe Ile Pro Ile Glu
                770                 775                 780

Lys Tyr Gln Phe Ser Leu Tyr Pro Ile Phe Met Glu Gly Val Gly Lys
785                 790                 795                 800

Pro Lys Ile Ile Asn Ser Phe Thr Gln Asp Ile Glu Lys His Gln
                805                 810                 815

Ser Asp Asp Lys Thr His Thr Cys Pro Pro Cys Pro Ala Pro Glu Leu
                820                 825                 830

Leu Gly Gly Pro Ser Val Phe Leu Phe Pro Pro Lys Pro Lys Asp Thr
                835                 840                 845

Leu Met Ile Ser Arg Thr Pro Glu Val Thr Cys Val Val Val Asp Val
850                 855                 860

Ser His Glu Asp Pro Glu Val Lys Phe Asn Trp Tyr Val Asp Gly Val
865                 870                 875                 880

Glu Val His Asn Ala Lys Thr Lys Pro Arg Glu Glu Gln Tyr Asn Ser
                885                 890                 895

Thr Tyr Arg Val Val Ser Val Leu Thr Val Leu His Gln Asp Trp Leu
                900                 905                 910

Asn Gly Lys Glu Tyr Lys Cys Lys Val Ser Asn Lys Ala Leu Pro Ala
                915                 920                 925

Pro Ile Glu Lys Thr Ile Ser Lys Ala Lys Gly Gln Pro Arg Glu Pro
                930                 935                 940

Gln Val Tyr Thr Leu Pro Pro Ser Arg Asp Glu Leu Thr Lys Asn Gln
945                 950                 955                 960
```

Val Ser Leu Thr Cys Leu Val Lys Gly Phe Tyr Pro Ser Asp Ile Ala
            965                 970                 975

Val Glu Trp Glu Ser Asn Gly Gln Pro Glu Asn Asn Tyr Lys Thr Thr
            980                 985                 990

Pro Pro Val Leu Asp Ser Asp Gly Ser Phe Phe Leu Tyr Ser Lys Leu
            995                 1000                1005

Thr Val Asp Lys Ser Arg Trp Gln Gln Gly Asn Val Phe Ser Cys
            1010                1015                1020

Ser Val Met His Glu Ala Leu His Asn His Tyr Thr Gln Lys Ser
            1025                1030                1035

Leu Ser Leu Ser Pro Gly Lys
            1040                1045

<210> SEQ ID NO 190
<211> LENGTH: 830
<212> TYPE: PRT
<213> ORGANISM: Artificial Sequence
<220> FEATURE:
<223> OTHER INFORMATION: hGP130-mFc

<400> SEQUENCE: 190

Glu Leu Leu Asp Pro Cys Gly Tyr Ile Ser Pro Glu Ser Pro Val Val
1               5                   10                  15

Gln Leu His Ser Asn Phe Thr Ala Val Cys Val Leu Lys Glu Lys Cys
            20                  25                  30

Met Asp Tyr Phe His Val Asn Ala Asn Tyr Ile Val Trp Lys Thr Asn
            35                  40                  45

His Phe Thr Ile Pro Lys Glu Gln Tyr Thr Ile Ile Asn Arg Thr Ala
    50                  55                  60

Ser Ser Val Thr Phe Thr Asp Ile Ala Ser Leu Asn Ile Gln Leu Thr
65                  70                  75                  80

Cys Asn Ile Leu Thr Phe Gly Gln Leu Glu Gln Asn Val Tyr Gly Ile
                85                  90                  95

Thr Ile Ile Ser Gly Leu Pro Pro Glu Lys Pro Lys Asn Leu Ser Cys
            100                 105                 110

Ile Val Asn Glu Gly Lys Lys Met Arg Cys Glu Trp Asp Gly Gly Arg
            115                 120                 125

Glu Thr His Leu Glu Thr Asn Phe Thr Leu Lys Ser Glu Trp Ala Thr
            130                 135                 140

His Lys Phe Ala Asp Cys Lys Ala Lys Arg Asp Thr Pro Thr Ser Cys
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
            180                 185                 190

Asp Pro Val Tyr Lys Val Lys Pro Asn Pro Pro His Asn Leu Ser Val
            195                 200                 205

Ile Asn Ser Glu Glu Leu Ser Ser Ile Leu Lys Leu Thr Trp Thr Asn
            210                 215                 220

Pro Ser Ile Lys Ser Val Ile Ile Leu Lys Tyr Asn Ile Gln Tyr Arg
225                 230                 235                 240

Thr Lys Asp Ala Ser Thr Trp Ser Gln Ile Pro Pro Glu Asp Thr Ala
                245                 250                 255

Ser Thr Arg Ser Ser Phe Thr Val Gln Asp Leu Lys Pro Phe Thr Glu
            260                 265                 270

```
Tyr Val Phe Arg Ile Arg Cys Met Lys Glu Asp Gly Lys Gly Tyr Trp
            275                 280                 285

Ser Asp Trp Ser Glu Glu Ala Ser Gly Ile Thr Tyr Glu Asp Arg Pro
        290                 295                 300

Ser Lys Ala Pro Ser Phe Trp Tyr Lys Ile Asp Pro Ser His Thr Gln
305                 310                 315                 320

Gly Tyr Arg Thr Val Gln Leu Val Trp Lys Thr Leu Pro Pro Phe Glu
            325                 330                 335

Ala Asn Gly Lys Ile Leu Asp Tyr Glu Val Thr Leu Thr Arg Trp Lys
            340                 345                 350

Ser His Leu Gln Asn Tyr Thr Val Asn Ala Thr Lys Leu Thr Val Asn
            355                 360                 365

Leu Thr Asn Asp Arg Tyr Leu Ala Thr Leu Thr Val Arg Asn Leu Val
            370                 375                 380

Gly Lys Ser Asp Ala Ala Val Leu Thr Ile Pro Ala Cys Asp Phe Gln
385                 390                 395                 400

Ala Thr His Pro Val Met Asp Leu Lys Ala Phe Pro Lys Asp Asn Met
            405                 410                 415

Leu Trp Val Glu Trp Thr Thr Pro Arg Glu Ser Val Lys Lys Tyr Ile
            420                 425                 430

Leu Glu Trp Cys Val Leu Ser Asp Lys Ala Pro Cys Ile Thr Asp Trp
            435                 440                 445

Gln Gln Glu Asp Gly Thr Val His Arg Thr Tyr Leu Arg Gly Asn Leu
            450                 455                 460

Ala Glu Ser Lys Cys Tyr Leu Ile Thr Val Thr Pro Val Tyr Ala Asp
465                 470                 475                 480

Gly Pro Gly Ser Pro Glu Ser Ile Lys Ala Tyr Leu Lys Gln Ala Pro
            485                 490                 495

Pro Ser Lys Gly Pro Thr Val Arg Thr Lys Lys Val Gly Lys Asn Glu
            500                 505                 510

Ala Val Leu Glu Trp Asp Gln Leu Pro Val Asp Val Gln Asn Gly Phe
            515                 520                 525

Ile Arg Asn Tyr Thr Ile Phe Tyr Arg Thr Ile Ile Gly Asn Glu Thr
            530                 535                 540

Ala Val Asn Val Asp Ser Ser His Thr Glu Tyr Thr Leu Ser Ser Leu
545                 550                 555                 560

Thr Ser Asp Thr Leu Tyr Met Val Arg Met Ala Ala Tyr Thr Asp Glu
            565                 570                 575

Gly Gly Lys Asp Gly Pro Glu Phe Thr Phe Thr Thr Pro Lys Phe Ala
            580                 585                 590

Gln Gly Glu Ile Glu Glu Pro Arg Gly Pro Thr Ile Lys Pro Cys Pro
            595                 600                 605

Pro Cys Lys Cys Pro Ala Pro Asn Leu Leu Gly Gly Pro Ser Val Phe
            610                 615                 620

Ile Phe Pro Pro Lys Ile Lys Asp Val Leu Met Ile Ser Leu Ser Pro
625                 630                 635                 640

Ile Val Thr Cys Val Val Val Asp Val Ser Glu Asp Asp Pro Asp Val
            645                 650                 655

Gln Ile Ser Trp Phe Val Asn Asn Val Glu Val His Thr Ala Gln Thr
            660                 665                 670

Gln Thr His Arg Glu Asp Tyr Asn Ser Thr Leu Arg Val Val Ser Ala
            675                 680                 685
```

```
Leu Pro Ile Gln His Gln Asp Trp Met Ser Gly Lys Glu Phe Lys Cys
690                 695                 700

Lys Val Asn Asn Lys Asp Leu Pro Ala Pro Ile Glu Arg Thr Ile Ser
705                 710                 715                 720

Lys Pro Lys Gly Ser Val Arg Ala Pro Gln Val Tyr Val Leu Pro Pro
            725                 730                 735

Pro Glu Glu Glu Met Thr Lys Lys Gln Val Thr Leu Thr Cys Met Val
            740                 745                 750

Thr Asp Phe Met Pro Glu Asp Ile Tyr Val Glu Trp Thr Asn Asn Gly
            755                 760                 765

Lys Thr Glu Leu Asn Tyr Lys Asn Thr Glu Pro Val Leu Asp Ser Asp
770                 775                 780

Gly Ser Tyr Phe Met Tyr Ser Lys Leu Arg Val Glu Lys Lys Asn Trp
785                 790                 795                 800

Val Glu Arg Asn Ser Tyr Ser Cys Ser Val Val His Glu Gly Leu His
                805                 810                 815

Asn His His Thr Thr Lys Ser Phe Ser Arg Thr Pro Gly Lys
                820                 825                 830

<210> SEQ ID NO 191
<211> LENGTH: 625
<212> TYPE: PRT
<213> ORGANISM: Artificial Sequence
<220> FEATURE:
<223> OTHER INFORMATION: hGP130-MMH

<400> SEQUENCE: 191

Glu Leu Leu Asp Pro Cys Gly Tyr Ile Ser Pro Glu Ser Pro Val Val
1               5                   10                  15

Gln Leu His Ser Asn Phe Thr Ala Val Cys Val Leu Lys Glu Lys Cys
                20                  25                  30

Met Asp Tyr Phe His Val Asn Ala Asn Tyr Ile Val Trp Lys Thr Asn
            35                  40                  45

His Phe Thr Ile Pro Lys Glu Gln Tyr Thr Ile Ile Asn Arg Thr Ala
    50                  55                  60

Ser Ser Val Thr Phe Thr Asp Ile Ala Ser Leu Asn Ile Gln Leu Thr
65                  70                  75                  80

Cys Asn Ile Leu Thr Phe Gly Gln Leu Glu Gln Asn Val Tyr Gly Ile
                85                  90                  95

Thr Ile Ile Ser Gly Leu Pro Pro Glu Lys Pro Lys Asn Leu Ser Cys
            100                 105                 110

Ile Val Asn Glu Gly Lys Lys Met Arg Cys Glu Trp Asp Gly Gly Arg
        115                 120                 125

Glu Thr His Leu Glu Thr Asn Phe Thr Leu Lys Ser Glu Trp Ala Thr
    130                 135                 140

His Lys Phe Ala Asp Cys Lys Ala Lys Arg Asp Thr Pro Thr Ser Cys
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
            180                 185                 190

Asp Pro Val Tyr Lys Val Lys Pro Asn Pro Pro His Asn Leu Ser Val
        195                 200                 205

Ile Asn Ser Glu Glu Leu Ser Ser Ile Leu Lys Leu Thr Trp Thr Asn
    210                 215                 220
```

```
Pro Ser Ile Lys Ser Val Ile Ile Leu Lys Tyr Asn Ile Gln Tyr Arg
225                 230                 235                 240

Thr Lys Asp Ala Ser Thr Trp Ser Gln Ile Pro Pro Glu Asp Thr Ala
            245                 250                 255

Ser Thr Arg Ser Ser Phe Thr Val Gln Asp Leu Lys Pro Phe Thr Glu
        260                 265                 270

Tyr Val Phe Arg Ile Arg Cys Met Lys Glu Asp Gly Lys Gly Tyr Trp
    275                 280                 285

Ser Asp Trp Ser Glu Glu Ala Ser Gly Ile Thr Tyr Glu Asp Arg Pro
290                 295                 300

Ser Lys Ala Pro Ser Phe Trp Tyr Lys Ile Asp Pro Ser His Thr Gln
305                 310                 315                 320

Gly Tyr Arg Thr Val Gln Leu Val Trp Lys Thr Leu Pro Pro Phe Glu
            325                 330                 335

Ala Asn Gly Lys Ile Leu Asp Tyr Glu Val Thr Leu Thr Arg Trp Lys
            340                 345                 350

Ser His Leu Gln Asn Tyr Thr Val Asn Ala Thr Lys Leu Thr Val Asn
        355                 360                 365

Leu Thr Asn Asp Arg Tyr Leu Ala Thr Leu Thr Val Arg Asn Leu Val
    370                 375                 380

Gly Lys Ser Asp Ala Ala Val Leu Thr Ile Pro Ala Cys Asp Phe Gln
385                 390                 395                 400

Ala Thr His Pro Val Met Asp Leu Lys Ala Phe Pro Lys Asp Asn Met
            405                 410                 415

Leu Trp Val Glu Trp Thr Thr Pro Arg Glu Ser Val Lys Lys Tyr Ile
            420                 425                 430

Leu Glu Trp Cys Val Leu Ser Asp Lys Ala Pro Cys Ile Thr Asp Trp
            435                 440                 445

Gln Gln Glu Asp Gly Thr Val His Arg Thr Tyr Leu Arg Gly Asn Leu
450                 455                 460

Ala Glu Ser Lys Cys Tyr Leu Ile Thr Val Thr Pro Val Tyr Ala Asp
465                 470                 475                 480

Gly Pro Gly Ser Pro Glu Ser Ile Lys Ala Tyr Leu Lys Gln Ala Pro
            485                 490                 495

Pro Ser Lys Gly Pro Thr Val Arg Thr Lys Lys Val Gly Lys Asn Glu
        500                 505                 510

Ala Val Leu Glu Trp Asp Gln Leu Pro Val Asp Val Gln Asn Gly Phe
        515                 520                 525

Ile Arg Asn Tyr Thr Ile Phe Tyr Arg Thr Ile Ile Gly Asn Glu Thr
530                 535                 540

Ala Val Asn Val Asp Ser Ser His Thr Glu Tyr Thr Leu Ser Ser Leu
545                 550                 555                 560

Thr Ser Asp Thr Leu Tyr Met Val Arg Met Ala Ala Tyr Thr Asp Glu
            565                 570                 575

Gly Gly Lys Asp Gly Pro Glu Phe Thr Phe Thr Thr Pro Lys Phe Ala
            580                 585                 590

Gln Gly Glu Ile Glu Glu Gln Lys Leu Ile Ser Glu Glu Asp Leu Gly
        595                 600                 605

Gly Glu Gln Lys Leu Ile Ser Glu Glu Asp Leu His His His His His
            610                 615                 620

His
625
```

```
<210> SEQ ID NO 192
<211> LENGTH: 524
<212> TYPE: PRT
<213> ORGANISM: Artificial Sequence
<220> FEATURE:
<223> OTHER INFORMATION: hGP130 delta D1-MMH

<400> SEQUENCE: 192

Leu Pro Pro Glu Lys Pro Lys Asn Leu Ser Cys Ile Val Asn Glu Gly
1               5                   10                  15

Lys Lys Met Arg Cys Glu Trp Asp Gly Gly Arg Glu Thr His Leu Glu
            20                  25                  30

Thr Asn Phe Thr Leu Lys Ser Glu Trp Ala Thr His Lys Phe Ala Asp
        35                  40                  45

Cys Lys Ala Lys Arg Asp Thr Pro Thr Ser Cys Thr Val Asp Tyr Ser
    50                  55                  60

Thr Val Tyr Phe Val Asn Ile Glu Val Trp Val Glu Ala Glu Asn Ala
65                  70                  75                  80

Leu Gly Lys Val Thr Ser Asp His Ile Asn Phe Asp Pro Val Tyr Lys
                85                  90                  95

Val Lys Pro Asn Pro Pro His Asn Leu Ser Val Ile Asn Ser Glu Glu
            100                 105                 110

Leu Ser Ser Ile Leu Lys Leu Thr Trp Thr Asn Pro Ser Ile Lys Ser
        115                 120                 125

Val Ile Ile Leu Lys Tyr Asn Ile Gln Tyr Arg Thr Lys Asp Ala Ser
    130                 135                 140

Thr Trp Ser Gln Ile Pro Pro Glu Asp Thr Ala Ser Thr Arg Ser Ser
145                 150                 155                 160

Phe Thr Val Gln Asp Leu Lys Pro Phe Thr Glu Tyr Val Phe Arg Ile
                165                 170                 175

Arg Cys Met Lys Glu Asp Gly Lys Gly Tyr Trp Ser Asp Trp Ser Glu
            180                 185                 190

Glu Ala Ser Gly Ile Thr Tyr Glu Asp Arg Pro Ser Lys Ala Pro Ser
        195                 200                 205

Phe Trp Tyr Lys Ile Asp Pro Ser His Thr Gln Gly Tyr Arg Thr Val
    210                 215                 220

Gln Leu Val Trp Lys Thr Leu Pro Pro Phe Glu Ala Asn Gly Lys Ile
225                 230                 235                 240

Leu Asp Tyr Glu Val Thr Leu Thr Arg Trp Lys Ser His Leu Gln Asn
                245                 250                 255

Tyr Thr Val Asn Ala Thr Lys Leu Thr Val Asn Leu Thr Asn Asp Arg
            260                 265                 270

Tyr Leu Ala Thr Leu Thr Val Arg Asn Leu Val Gly Lys Ser Asp Ala
        275                 280                 285

Ala Val Leu Thr Ile Pro Ala Cys Asp Phe Gln Ala Thr His Pro Val
    290                 295                 300

Met Asp Leu Lys Ala Phe Pro Lys Asp Asn Met Leu Trp Val Glu Trp
305                 310                 315                 320

Thr Thr Pro Arg Glu Ser Val Lys Lys Tyr Ile Leu Glu Trp Cys Val
                325                 330                 335

Leu Ser Asp Lys Ala Pro Cys Ile Thr Asp Trp Gln Gln Glu Asp Gly
            340                 345                 350

Thr Val His Arg Thr Tyr Leu Arg Gly Asn Leu Ala Glu Ser Lys Cys
        355                 360                 365

Tyr Leu Ile Thr Val Thr Pro Val Tyr Ala Asp Gly Pro Gly Ser Pro
```

```
                    370                 375                 380
Glu Ser Ile Lys Ala Tyr Leu Lys Gln Ala Pro Pro Ser Lys Gly Pro
385                 390                 395                 400

Thr Val Arg Thr Lys Lys Val Gly Lys Asn Glu Ala Val Leu Glu Trp
                    405                 410                 415

Asp Gln Leu Pro Val Asp Val Gln Asn Gly Phe Ile Arg Asn Tyr Thr
                420                 425                 430

Ile Phe Tyr Arg Thr Ile Ile Gly Asn Glu Thr Ala Val Asn Val Asp
                435                 440                 445

Ser Ser His Thr Glu Tyr Thr Leu Ser Ser Leu Thr Ser Asp Thr Leu
            450                 455                 460

Tyr Met Val Arg Met Ala Ala Tyr Thr Asp Glu Gly Lys Asp Gly
465                 470                 475                 480

Pro Glu Phe Thr Phe Thr Thr Pro Lys Phe Ala Gln Gly Glu Ile Glu
                485                 490                 495

Glu Gln Lys Leu Ile Ser Glu Glu Asp Leu Gly Gly Glu Gln Lys Leu
                500                 505                 510

Ile Ser Glu Glu Asp Leu His His His His His His
            515                 520

<210> SEQ ID NO 193
<211> LENGTH: 319
<212> TYPE: PRT
<213> ORGANISM: Artificial Sequence
<220> FEATURE:
<223> OTHER INFORMATION: hGP130 delta D1-D3-MMH

<400> SEQUENCE: 193

Ala Pro Ser Phe Trp Tyr Lys Ile Asp Pro Ser His Thr Gln Gly Tyr
1               5                   10                  15

Arg Thr Val Gln Leu Val Trp Lys Thr Leu Pro Pro Phe Glu Ala Asn
                20                  25                  30

Gly Lys Ile Leu Asp Tyr Glu Val Thr Leu Thr Arg Trp Lys Ser His
                35                  40                  45

Leu Gln Asn Tyr Thr Val Asn Ala Thr Lys Leu Thr Val Asn Leu Thr
            50                  55                  60

Asn Asp Arg Tyr Leu Ala Thr Leu Thr Val Arg Asn Leu Val Gly Lys
65              70                  75                  80

Ser Asp Ala Ala Val Leu Thr Ile Pro Ala Cys Asp Phe Gln Ala Thr
                85                  90                  95

His Pro Val Met Asp Leu Lys Ala Phe Pro Lys Asp Asn Met Leu Trp
                100                 105                 110

Val Glu Trp Thr Thr Pro Arg Glu Ser Val Lys Lys Tyr Ile Leu Glu
            115                 120                 125

Trp Cys Val Leu Ser Asp Lys Ala Pro Cys Ile Thr Asp Trp Gln Gln
            130                 135                 140

Glu Asp Gly Thr Val His Arg Thr Tyr Leu Arg Gly Asn Leu Ala Glu
145                 150                 155                 160

Ser Lys Cys Tyr Leu Ile Thr Val Thr Pro Val Tyr Ala Asp Gly Pro
                165                 170                 175

Gly Ser Pro Glu Ser Ile Lys Ala Tyr Leu Lys Gln Ala Pro Pro Ser
                180                 185                 190

Lys Gly Pro Thr Val Arg Thr Lys Lys Val Gly Lys Asn Glu Ala Val
                195                 200                 205

Leu Glu Trp Asp Gln Leu Pro Val Asp Val Gln Asn Gly Phe Ile Arg
```

```
            210                 215                 220
Asn Tyr Thr Ile Phe Tyr Arg Thr Ile Ile Gly Asn Glu Thr Ala Val
225                 230                 235                 240

Asn Val Asp Ser Ser His Thr Glu Tyr Thr Leu Ser Ser Leu Thr Ser
                245                 250                 255

Asp Thr Leu Tyr Met Val Arg Met Ala Ala Tyr Thr Asp Glu Gly Gly
                260                 265                 270

Lys Asp Gly Pro Glu Phe Thr Phe Thr Thr Pro Lys Phe Ala Gln Gly
            275                 280                 285

Glu Ile Glu Glu Gln Lys Leu Ile Ser Glu Glu Asp Leu Gly Gly Glu
        290                 295                 300

Gln Lys Leu Ile Ser Glu Glu Asp Leu His His His His His His
305                 310                 315
```

<210> SEQ ID NO 194
<211> LENGTH: 625
<212> TYPE: PRT
<213> ORGANISM: Artificial Sequence
<220> FEATURE:
<223> OTHER INFORMATION: MfGP130-MMH

<400> SEQUENCE: 194

```
Glu Leu Leu Asp Pro Cys Gly Tyr Ile Ser Pro Glu Ser Pro Val Val
1               5                   10                  15

Gln Leu His Ser Asn Phe Thr Ala Val Cys Val Leu Lys Glu Lys Cys
                20                  25                  30

Met Asp Tyr Phe His Val Asn Ala Asn Tyr Ile Val Trp Lys Thr Asn
            35                  40                  45

His Phe Thr Ile Pro Lys Glu Gln Tyr Thr Ile Asn Arg Thr Ala
        50                  55                  60

Ser Ser Val Thr Phe Thr Asp Ile Ser Ser Leu Asn Ile Gln Leu Thr
65                  70                  75                  80

Cys Asn Ile Leu Thr Phe Gly Gln Leu Glu Gln Asn Val Tyr Gly Ile
                85                  90                  95

Thr Ile Ile Ser Gly Leu Pro Pro Glu Lys Pro Lys Asn Leu Ser Cys
            100                 105                 110

Ile Val Asn Glu Gly Lys Lys Met Arg Cys Glu Trp Asn Arg Gly Arg
        115                 120                 125

Glu Thr His Leu Glu Thr Asn Phe Thr Leu Lys Ser Glu Trp Ala Thr
130                 135                 140

His Lys Phe Ala Asp Cys Lys Ala Lys Arg Asp Thr Pro Thr Ser Cys
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
            180                 185                 190

Asp Pro Val Tyr Lys Val Lys Pro Asn Pro His Asn Leu Ser Val
        195                 200                 205

Ile Asn Ser Glu Glu Leu Ser Ser Ile Leu Lys Leu Thr Trp Thr Asn
    210                 215                 220

Pro Ser Ile Lys Ser Val Ile Arg Leu Lys Tyr Asn Ile Gln Tyr Arg
225                 230                 235                 240

Thr Lys Asp Ala Ser Thr Trp Ser Gln Ile Pro Pro Glu Asp Thr Ala
                245                 250                 255

Ser Thr Arg Ser Ser Phe Thr Val Gln Asp Leu Lys Pro Phe Thr Glu
```

```
                260                 265                 270
Tyr Val Phe Arg Ile Cys Cys Met Lys Glu Asp Gly Lys Gly Tyr Trp
            275                 280                 285
Ser Asp Trp Ser Glu Glu Ala Asn Gly Ile Thr Tyr Glu Asp Arg Pro
        290                 295                 300
Ser Lys Ala Pro Ser Phe Trp Tyr Lys Ile Asp Pro Ser His Ala Gln
305                 310                 315                 320
Gly Tyr Arg Thr Val Gln Leu Met Trp Lys Thr Leu Pro Pro Phe Glu
                325                 330                 335
Ala Asn Gly Lys Ile Leu Asp Tyr Glu Val Thr Leu Thr Arg Trp Lys
            340                 345                 350
Ser His Leu Gln Asn Tyr Thr Val Asn Asp Thr Lys Leu Thr Val Asn
        355                 360                 365
Leu Thr Asn Asp Arg Tyr Val Ala Thr Leu Thr Ala Arg Asn Leu Val
        370                 375                 380
Gly Lys Ser Asp Ala Ala Val Leu Thr Ile Pro Ala Cys Asp Phe Gln
385                 390                 395                 400
Ala Thr His Pro Val Met Asp Leu Lys Ala Phe Pro Lys Asp Asn Met
                405                 410                 415
Leu Trp Val Glu Trp Thr Thr Pro Arg Glu Ser Val Lys Lys Tyr Ile
            420                 425                 430
Leu Glu Trp Cys Val Leu Ser Asp Lys Ala Pro Cys Ile Ala Asp Trp
        435                 440                 445
Gln Gln Glu Asp Gly Thr Val His Arg Thr His Leu Arg Gly Asn Leu
    450                 455                 460
Ala Glu Ser Lys Cys Tyr Leu Ile Thr Val Thr Pro Val Tyr Ala Asp
465                 470                 475                 480
Gly Pro Gly Ser Pro Glu Ser Ile Lys Ala Tyr Leu Lys Gln Ala Pro
                485                 490                 495
Pro Ser Lys Gly Pro Thr Val Arg Thr Lys Lys Val Gly Lys Asn Glu
            500                 505                 510
Ala Val Leu Glu Trp Asp Gln Leu Pro Val Asp Val Gln Asn Gly Phe
        515                 520                 525
Ile Arg Asn Tyr Thr Ile Phe Tyr Arg Thr Ile Ile Gly Asn Glu Thr
    530                 535                 540
Ala Val Asn Val Asp Ser Ser His Thr Glu Tyr Thr Leu Ser Ser Leu
545                 550                 555                 560
Thr Ser Asp Thr Leu Tyr Met Val Arg Met Ala Ala Tyr Thr Asp Glu
                565                 570                 575
Gly Gly Lys Asp Gly Pro Glu Phe Thr Phe Thr Thr Pro Lys Phe Ala
            580                 585                 590
Gln Gly Glu Ile Glu Glu Gln Lys Leu Ile Ser Glu Glu Asp Leu Gly
        595                 600                 605
Gly Glu Gln Lys Leu Ile Ser Glu Glu Asp Leu His His His His
    610                 615                 620
His
625

<210> SEQ ID NO 195
<211> LENGTH: 624
<212> TYPE: PRT
<213> ORGANISM: Artificial Sequence
<220> FEATURE:
<223> OTHER INFORMATION: rGP130-MMH
```

<400> SEQUENCE: 195

```
Gln Leu Val Glu Pro Cys Gly Tyr Ile Tyr Pro Glu Phe Pro Val Val
1               5                   10                  15

Gln Arg Gly Ser Asn Phe Thr Ala Thr Cys Val Leu Lys Glu Lys Cys
            20                  25                  30

Leu Gln Val Tyr Ser Val Asn Ala Thr Tyr Ile Val Trp Lys Thr Asn
        35                  40                  45

His Val Ala Val Pro Lys Glu Gln Val Thr Val Ile Asn Arg Thr Ala
    50                  55                  60

Ser Ser Val Thr Phe Thr Asp Val Val Phe Gln Asn Val Gln Leu Thr
65                  70                  75                  80

Cys Asn Ile Leu Ser Phe Gly Gln Ile Glu Gln Asn Val Tyr Gly Ile
                85                  90                  95

Thr Ile Leu Ser Gly Tyr Pro Pro Asp Ile Pro Thr Asn Leu Ser Cys
            100                 105                 110

Ile Val Asn Glu Gly Lys Asn Met Leu Cys Gln Trp Asp Pro Gly Arg
        115                 120                 125

Glu Thr Tyr Leu Glu Thr Asn Tyr Thr Leu Lys Ser Glu Trp Ala Thr
    130                 135                 140

Glu Lys Phe Pro Asp Cys Arg Thr Lys His Gly Thr Ser Ser Cys Met
145                 150                 155                 160

Met Gly Tyr Thr Pro Ile Tyr Phe Val Asn Ile Glu Val Trp Val Glu
                165                 170                 175

Ala Glu Asn Ala Leu Gly Asn Val Ser Ser Glu Pro Ile Asn Phe Asp
            180                 185                 190

Pro Val Asp Lys Val Lys Pro Ser Pro Pro His Asn Leu Ser Val Thr
        195                 200                 205

Asn Ser Glu Glu Leu Ser Ser Ile Leu Lys Leu Ala Trp Val Asn Ser
    210                 215                 220

Gly Leu Asp Ser Ile Leu Arg Leu Lys Ser Asp Ile Gln Tyr Arg Thr
225                 230                 235                 240

Lys Asp Ala Ser Thr Trp Ile Gln Val Pro Leu Glu Asp Thr Val Ser
                245                 250                 255

Pro Arg Thr Ser Phe Thr Val Gln Asp Leu Lys Pro Phe Thr Glu Tyr
            260                 265                 270

Val Phe Arg Ile Arg Ser Ile Lys Glu Asn Gly Lys Gly Tyr Trp Ser
        275                 280                 285

Asp Trp Ser Glu Glu Ala Ser Gly Thr Thr Tyr Glu Asp Arg Pro Ser
    290                 295                 300

Lys Ala Pro Ser Phe Trp Tyr Lys Val Asn Ala Asn His Pro Gln Glu
305                 310                 315                 320

Tyr Arg Ser Ala Arg Leu Ile Trp Lys Thr Leu Pro Leu Ser Glu Ala
                325                 330                 335

Asn Gly Lys Ile Leu Asp Tyr Glu Val Val Leu Thr Gln Ser Lys Ser
            340                 345                 350

Val Ser Gln Thr Tyr Thr Val Asn Gly Thr Glu Leu Ile Val Asn Leu
        355                 360                 365

Thr Asn Asn Arg Tyr Val Ala Ser Leu Ala Ala Arg Asn Val Val Gly
    370                 375                 380

Lys Ser Pro Ala Thr Val Leu Thr Ile Pro Gly Ser His Phe Lys Ala
385                 390                 395                 400

Ser His Pro Val Val Asp Leu Lys Ala Phe Pro Lys Asp Asn Leu Leu
                405                 410                 415
```

Trp Val Glu Trp Thr Pro Pro Ser Lys Pro Val Asn Lys Tyr Ile Leu
            420             425             430

Glu Trp Cys Val Leu Ser Glu Asn Ser Pro Cys Ile Pro Asp Trp Gln
        435             440             445

Gln Glu Asp Gly Thr Val Asn Arg Thr His Leu Arg Gly Ser Leu Leu
450             455             460

Glu Ser Lys Cys Tyr Leu Ile Thr Val Thr Pro Val Phe Pro Gly Gly
465             470             475             480

Pro Gly Ser Pro Glu Ser Met Lys Ala Tyr Leu Lys Gln Ala Ala Pro
            485             490             495

Ser Lys Gly Pro Thr Val Arg Thr Lys Val Gly Lys Asn Glu Ala
            500             505             510

Val Leu Glu Trp Asp His Leu Pro Val Asp Val Gln Asn Gly Phe Ile
            515             520             525

Arg Asn Tyr Ser Ile Ser Tyr Arg Thr Ser Val Gly Lys Glu Met Val
530             535             540

Val Arg Val Asp Ser Ser His Thr Glu Tyr Thr Leu Ser Ser Leu Ser
545             550             555             560

Ser Asp Thr Leu Tyr Met Val His Met Ala Ala Tyr Thr Glu Glu Gly
            565             570             575

Gly Lys Asp Gly Pro Glu Phe Thr Phe Thr Thr Leu Lys Phe Ala Gln
            580             585             590

Gly Glu Ile Glu Glu Gln Lys Leu Ile Ser Glu Glu Asp Leu Gly Gly
            595             600             605

Glu Gln Lys Leu Ile Ser Glu Glu Asp Leu His His His His His His
            610             615             620

<210> SEQ ID NO 196
<211> LENGTH: 623
<212> TYPE: PRT
<213> ORGANISM: Artificial Sequence
<220> FEATURE:
<223> OTHER INFORMATION: mGP130-MMH

<400> SEQUENCE: 196

Gln Leu Leu Glu Pro Cys Gly Tyr Ile Tyr Pro Glu Phe Pro Val Val
1               5               10              15

Gln Arg Gly Ser Asn Phe Thr Ala Ile Cys Val Leu Lys Glu Ala Cys
            20              25              30

Leu Gln His Tyr Tyr Val Asn Ala Ser Tyr Ile Val Trp Lys Thr Asn
            35              40              45

His Ala Ala Val Pro Arg Glu Gln Val Thr Val Ile Asn Arg Thr Thr
50              55              60

Ser Ser Val Thr Phe Thr Asp Val Val Leu Pro Ser Val Gln Leu Thr
65              70              75              80

Cys Asn Ile Leu Ser Phe Gly Gln Ile Glu Gln Asn Val Tyr Gly Val
            85              90              95

Thr Met Leu Ser Gly Phe Pro Pro Asp Lys Pro Thr Asn Leu Thr Cys
            100             105             110

Ile Val Asn Glu Gly Lys Asn Met Leu Cys Gln Trp Asp Pro Gly Arg
            115             120             125

Glu Thr Tyr Leu Glu Thr Asn Tyr Thr Leu Lys Ser Glu Trp Ala Thr
            130             135             140

Glu Lys Phe Pro Asp Cys Gln Ser Lys His Gly Thr Ser Cys Met Val
145             150             155             160

-continued

```
Ser Tyr Met Pro Thr Tyr Tyr Val Asn Ile Glu Val Trp Val Glu Ala
            165                 170                 175

Glu Asn Ala Leu Gly Lys Val Ser Ser Glu Ser Ile Asn Phe Asp Pro
        180                 185                 190

Val Asp Lys Val Lys Pro Thr Pro Pro Tyr Asn Leu Ser Val Thr Asn
        195                 200                 205

Ser Glu Glu Leu Ser Ser Ile Leu Lys Leu Ser Trp Val Ser Ser Gly
    210                 215                 220

Leu Gly Gly Leu Leu Asp Leu Lys Ser Asp Ile Gln Tyr Arg Thr Lys
225                 230                 235                 240

Asp Ala Ser Thr Trp Ile Gln Val Pro Leu Asp Thr Met Ser Pro
            245                 250                 255

Arg Thr Ser Phe Thr Val Gln Asp Leu Lys Pro Phe Thr Glu Tyr Val
            260                 265                 270

Phe Arg Ile Arg Ser Ile Lys Asp Ser Gly Lys Gly Tyr Trp Ser Asp
        275                 280                 285

Trp Ser Glu Glu Ala Ser Gly Thr Thr Tyr Glu Asp Arg Pro Ser Arg
    290                 295                 300

Pro Pro Ser Phe Trp Tyr Lys Thr Asn Pro Ser His Gly Gln Glu Tyr
305                 310                 315                 320

Arg Ser Val Arg Leu Ile Trp Lys Ala Leu Pro Leu Ser Glu Ala Asn
            325                 330                 335

Gly Lys Ile Leu Asp Tyr Glu Val Ile Leu Thr Gln Ser Lys Ser Val
            340                 345                 350

Ser Gln Thr Tyr Thr Val Thr Gly Thr Glu Leu Thr Val Asn Leu Thr
        355                 360                 365

Asn Asp Arg Tyr Val Ala Ser Leu Ala Ala Arg Asn Lys Val Gly Lys
    370                 375                 380

Ser Ala Ala Val Leu Thr Ile Pro Ser Pro His Val Thr Ala Ala
385                 390                 395                 400

Tyr Ser Val Val Asn Leu Lys Ala Phe Pro Lys Asp Asn Leu Leu Trp
            405                 410                 415

Val Glu Trp Thr Pro Pro Lys Pro Val Ser Lys Tyr Ile Leu Glu
            420                 425                 430

Trp Cys Val Leu Ser Glu Asn Ala Pro Cys Val Glu Asp Trp Gln Gln
        435                 440                 445

Glu Asp Ala Thr Val Asn Arg Thr His Leu Arg Gly Arg Leu Leu Glu
    450                 455                 460

Ser Lys Cys Tyr Gln Ile Thr Val Thr Pro Val Phe Ala Thr Gly Pro
465                 470                 475                 480

Gly Gly Ser Glu Ser Leu Lys Ala Tyr Leu Lys Gln Ala Ala Pro Ala
            485                 490                 495

Arg Gly Pro Thr Val Arg Thr Lys Lys Val Gly Lys Asn Glu Ala Val
            500                 505                 510

Leu Ala Trp Asp Gln Ile Pro Val Asp Asp Gln Asn Gly Phe Ile Arg
        515                 520                 525

Asn Tyr Ser Ile Ser Tyr Arg Thr Ser Val Gly Lys Glu Met Val Val
    530                 535                 540

His Val Asp Ser Ser His Thr Glu Tyr Thr Leu Ser Ser Leu Ser Ser
545                 550                 555                 560

Asp Thr Leu Tyr Met Val Arg Met Ala Ala Tyr Thr Asp Glu Gly Gly
            565                 570                 575
```

```
Lys Asp Gly Pro Glu Phe Thr Phe Thr Thr Pro Lys Phe Ala Gln Gly
            580                 585                 590

Glu Ile Glu Glu Gln Lys Leu Ile Ser Glu Glu Asp Leu Gly Gly Glu
        595                 600                 605

Gln Lys Leu Ile Ser Glu Glu Asp Leu His His His His His His
    610                 615                 620

<210> SEQ ID NO 197
<211> LENGTH: 824
<212> TYPE: PRT
<213> ORGANISM: Artificial Sequence
<220> FEATURE:
<223> OTHER INFORMATION: hGP130-hFc

<400> SEQUENCE: 197

Glu Leu Leu Asp Pro Cys Gly Tyr Ile Ser Pro Glu Ser Pro Val Val
1               5                   10                  15

Gln Leu His Ser Asn Phe Thr Ala Val Cys Val Leu Lys Glu Lys Cys
            20                  25                  30

Met Asp Tyr Phe His Val Asn Ala Asn Tyr Ile Val Trp Lys Thr Asn
        35                  40                  45

His Phe Thr Ile Pro Lys Glu Gln Tyr Thr Ile Asn Arg Thr Ala
    50                  55                  60

Ser Ser Val Thr Phe Thr Asp Ile Ala Ser Leu Asn Ile Gln Leu Thr
65                  70                  75                  80

Cys Asn Ile Leu Thr Phe Gly Gln Leu Glu Gln Asn Val Tyr Gly Ile
                85                  90                  95

Thr Ile Ile Ser Gly Leu Pro Pro Glu Lys Pro Lys Asn Leu Ser Cys
            100                 105                 110

Ile Val Asn Glu Gly Lys Lys Met Arg Cys Glu Trp Asp Gly Gly Arg
        115                 120                 125

Glu Thr His Leu Glu Thr Asn Phe Thr Leu Lys Ser Glu Trp Ala Thr
    130                 135                 140

His Lys Phe Ala Asp Cys Lys Ala Lys Arg Asp Thr Pro Thr Ser Cys
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
            180                 185                 190

Asp Pro Val Tyr Lys Val Lys Pro Asn Pro Pro His Asn Leu Ser Val
        195                 200                 205

Ile Asn Ser Glu Glu Leu Ser Ser Ile Leu Lys Leu Thr Trp Thr Asn
    210                 215                 220

Pro Ser Ile Lys Ser Val Ile Ile Leu Lys Tyr Asn Ile Gln Tyr Arg
225                 230                 235                 240

Thr Lys Asp Ala Ser Thr Trp Ser Gln Ile Pro Pro Glu Asp Thr Ala
                245                 250                 255

Ser Thr Arg Ser Ser Phe Thr Val Gln Asp Leu Lys Pro Phe Thr Glu
            260                 265                 270

Tyr Val Phe Arg Ile Arg Cys Met Lys Glu Asp Gly Lys Gly Tyr Trp
        275                 280                 285

Ser Asp Trp Ser Glu Glu Ala Ser Gly Ile Thr Tyr Glu Asp Arg Pro
    290                 295                 300

Ser Lys Ala Pro Ser Phe Trp Tyr Lys Ile Asp Pro Ser His Thr Gln
305                 310                 315                 320
```

Gly Tyr Arg Thr Val Gln Leu Val Trp Lys Thr Leu Pro Pro Phe Glu
            325                 330                 335

Ala Asn Gly Lys Ile Leu Asp Tyr Glu Val Thr Leu Thr Arg Trp Lys
        340                 345                 350

Ser His Leu Gln Asn Tyr Thr Val Asn Ala Thr Lys Leu Thr Val Asn
    355                 360                 365

Leu Thr Asn Asp Arg Tyr Leu Ala Thr Leu Thr Val Arg Asn Leu Val
370                 375                 380

Gly Lys Ser Asp Ala Ala Val Leu Thr Ile Pro Ala Cys Asp Phe Gln
385                 390                 395                 400

Ala Thr His Pro Val Met Asp Leu Lys Ala Phe Pro Lys Asp Asn Met
            405                 410                 415

Leu Trp Val Glu Trp Thr Thr Pro Arg Glu Ser Val Lys Lys Tyr Ile
        420                 425                 430

Leu Glu Trp Cys Val Leu Ser Asp Lys Ala Pro Cys Ile Thr Asp Trp
    435                 440                 445

Gln Gln Glu Asp Gly Thr Val His Arg Thr Tyr Leu Arg Gly Asn Leu
    450                 455                 460

Ala Glu Ser Lys Cys Tyr Leu Ile Thr Val Thr Pro Val Tyr Ala Asp
465                 470                 475                 480

Gly Pro Gly Ser Pro Glu Ser Ile Lys Ala Tyr Leu Lys Gln Ala Pro
            485                 490                 495

Pro Ser Lys Gly Pro Thr Val Arg Thr Lys Lys Val Gly Lys Asn Glu
        500                 505                 510

Ala Val Leu Glu Trp Asp Gln Leu Pro Val Asp Val Gln Asn Gly Phe
    515                 520                 525

Ile Arg Asn Tyr Thr Ile Phe Tyr Arg Thr Ile Ile Gly Asn Glu Thr
    530                 535                 540

Ala Val Asn Val Asp Ser Ser His Thr Glu Tyr Thr Leu Ser Ser Leu
545                 550                 555                 560

Thr Ser Asp Thr Leu Tyr Met Val Arg Met Ala Ala Tyr Thr Asp Glu
            565                 570                 575

Gly Gly Lys Asp Gly Pro Glu Phe Thr Phe Thr Thr Pro Lys Phe Ala
        580                 585                 590

Gln Gly Glu Ile Glu Asp Lys Thr His Thr Cys Pro Pro Cys Pro Ala
    595                 600                 605

Pro Glu Leu Leu Gly Gly Pro Ser Val Phe Leu Phe Pro Pro Lys Pro
    610                 615                 620

Lys Asp Thr Leu Met Ile Ser Arg Thr Pro Glu Val Thr Cys Val Val
625                 630                 635                 640

Val Asp Val Ser His Glu Asp Pro Glu Val Lys Phe Asn Trp Tyr Val
            645                 650                 655

Asp Gly Val Glu Val His Asn Ala Lys Thr Lys Pro Arg Glu Glu Gln
        660                 665                 670

Tyr Asn Ser Thr Tyr Arg Val Val Ser Val Leu Thr Val Leu His Gln
    675                 680                 685

Asp Trp Leu Asn Gly Lys Glu Tyr Lys Cys Lys Val Ser Asn Lys Ala
    690                 695                 700

Leu Pro Ala Pro Ile Glu Lys Thr Ile Ser Lys Ala Lys Gly Gln Pro
705                 710                 715                 720

Arg Glu Pro Gln Val Tyr Thr Leu Pro Pro Ser Arg Asp Glu Leu Thr
            725                 730                 735

Lys Asn Gln Val Ser Leu Thr Cys Leu Val Lys Gly Phe Tyr Pro Ser

```
                740               745               750
Asp Ile Ala Val Glu Trp Glu Ser Asn Gly Gln Pro Glu Asn Asn Tyr
            755               760               765

Lys Thr Thr Pro Pro Val Leu Asp Ser Asp Gly Ser Phe Phe Leu Tyr
    770               775               780

Ser Lys Leu Thr Val Asp Lys Ser Arg Trp Gln Gln Gly Asn Val Phe
785               790               795               800

Ser Cys Ser Val Met His Glu Ala Leu His Asn His Tyr Thr Gln Lys
                805               810               815

Ser Leu Ser Leu Ser Pro Gly Lys
                820

<210> SEQ ID NO 198
<211> LENGTH: 348
<212> TYPE: PRT
<213> ORGANISM: Artificial Sequence
<220> FEATURE:
<223> OTHER INFORMATION: hCNTFR-MMH

<400> SEQUENCE: 198

Gln Arg His Ser Pro Gln Glu Ala Pro His Val Gln Tyr Glu Arg Leu
1               5                   10                  15

Gly Ser Asp Val Thr Leu Pro Cys Gly Thr Ala Asn Trp Asp Ala Ala
                20                  25                  30

Val Thr Trp Arg Val Asn Gly Thr Asp Leu Ala Pro Asp Leu Leu Asn
            35                  40                  45

Gly Ser Gln Leu Val Leu His Gly Leu Glu Leu Gly His Ser Gly Leu
        50                  55                  60

Tyr Ala Cys Phe His Arg Asp Ser Trp His Leu Arg His Gln Val Leu
65                  70                  75                  80

Leu His Val Gly Leu Pro Pro Arg Glu Pro Val Leu Ser Cys Arg Ser
                85                  90                  95

Asn Thr Tyr Pro Lys Gly Phe Tyr Cys Ser Trp His Leu Pro Thr Pro
            100                 105                 110

Thr Tyr Ile Pro Asn Thr Phe Asn Val Thr Val Leu His Gly Ser Lys
        115                 120                 125

Ile Met Val Cys Glu Lys Asp Pro Ala Leu Lys Asn Arg Cys His Ile
130                 135                 140

Arg Tyr Met His Leu Phe Ser Thr Ile Lys Tyr Lys Val Ser Ile Ser
145                 150                 155                 160

Val Ser Asn Ala Leu Gly His Asn Ala Thr Ala Ile Thr Phe Asp Glu
                165                 170                 175

Phe Thr Ile Val Lys Pro Asp Pro Pro Glu Asn Val Val Ala Arg Pro
            180                 185                 190

Val Pro Ser Asn Pro Arg Arg Leu Glu Val Thr Trp Gln Thr Pro Ser
        195                 200                 205

Thr Trp Pro Asp Pro Glu Ser Phe Pro Leu Lys Phe Phe Leu Arg Tyr
    210                 215                 220

Arg Pro Leu Ile Leu Asp Gln Trp Gln His Val Glu Leu Ser Asp Gly
225                 230                 235                 240

Thr Ala His Thr Ile Thr Asp Ala Tyr Ala Gly Lys Glu Tyr Ile Ile
                245                 250                 255

Gln Val Ala Ala Lys Asp Asn Glu Ile Gly Thr Trp Ser Asp Trp Ser
            260                 265                 270

Val Ala Ala His Ala Thr Pro Trp Thr Glu Glu Pro Arg His Leu Thr
```

-continued

```
              275                 280                 285
Thr Glu Ala Gln Ala Ala Glu Thr Thr Thr Ser Thr Thr Ser Ser Leu
    290                 295                 300

Ala Pro Pro Pro Thr Thr Lys Ile Cys Asp Pro Gly Glu Leu Gly Ser
305                 310                 315                 320

Glu Gln Lys Leu Ile Ser Glu Glu Asp Leu Gly Gly Glu Gln Lys Leu
                325                 330                 335

Ile Ser Glu Glu Asp Leu His His His His His His
                340                 345
```

BISPECIFIC ANTIGEN BINDING MOLECULES THAT BIND LEPTIN RECEPTOR AND/OR GP130, AND METHODS OF USE THEREOF

This application claims the benefit of U.S. provisional patent application No. 62/607,137, filed Dec. 18, 2017 and 62/635,406, filed Feb. 26, 2018; each of which is herein incorporated by reference in its entirety.

FIELD OF THE INVENTION

The present invention relates to antigen-binding molecules, including bispecific antigen-binding molecules (e.g., bispecific antibodies) that bind human GP130 and/or human leptin receptor (LEPR), and the use of such antigen-binding molecules for the treatment of conditions and disorders related to leptin deficiency or leptin resistance.

SEQUENCE LISTING

An official copy of the sequence listing is submitted concurrently with the specification electronically via EFS-Web as an ASCII formatted sequence listing with a file name of "10397US01_SEQ_LIST_ST25.txt", a creations date of Dec. 17, 2018, and a size of about 151 KB. The sequence listing contained in this ASCII formatted document is part of the specification and is herein incorporated by reference in its entirety.

BACKGROUND

Glycoprotein 130 (GP130) is a component of a receptor complex that also comprises CNTRF-alpha and LIFR-beta. Signaling through this receptor complex activates JAK/STAT signaling which, in certain biological contexts, results in reduced appetite, food intake and weight loss.

Leptin is a polypeptide hormone predominantly expressed by adipose tissue and is involved in the regulation of metabolism, energy balance and food intake. Leptin activity is mediated by interaction with, and signaling through, the leptin receptor. Leptin receptor, (also known as "LEPR," "WSX," "OB receptor," "OB-R," and "CD295") is a single-pass transmembrane receptor of the class I cytokine receptor family with a large (818 amino acid) extracellular domain. Leptin deficiency, leptin resistance, and certain LEPR signaling-defective/signaling impaired mutations, are associated with obesity, type 2 diabetes, dyslipidemia, lipodystrophies, hepatic steatosis, non-alcoholic and alcoholic fatty liver diseases, severe insulin resistance, Leprechaunism/Donohue syndrome, Rabson-Mendenhall syndrome, and related complications. Therapeutic approaches to address leptin resistance, leptin deficiency, and hypoleptinemia (e.g., lipodystrophy) have mostly focused on the delivery of supplemental leptin or leptin analogues to affected individuals. Such approaches, however, have generally shown limited efficacy, particularly in leptin-resistant individuals, and are frequently associated with adverse side effects. Thus, a need exists in the art for alternative approaches to treating leptin resistance and other conditions associated with leptin deficiency or hypoleptinemia.

BRIEF SUMMARY OF THE INVENTION

The present invention relates, in part, to the concept of antibody-mediated heterodimerization of the LEPR and GP130 to activate both receptors and thereby stimulate the anorexegenic effects associated with signaling through these receptors. Accordingly, the present invention provides antigen-binding molecules (e.g., antibodies and antigen-binding fragments of antibodies) that bind human GP130 and/or human leptin receptor (LEPR). According to certain embodiments, the present invention provides bispecific antigen-binding molecules comprising a first antigen-binding domain (D1) that specifically binds human GP130, and a second antigen-binding domain (D2) that specifically binds human leptin receptor (LEPR). The present invention includes LEPR×GP130 bispecific molecules (e.g., bispecific antibodies). In certain exemplary embodiments of the invention, the anti-GP130 antigen-binding domain (D1) and the anti-LEPR (D2) antigen-binding domain each comprise different, distinct heavy chain variable regions (HCVRs) paired with the same or a different light chain variable regions (LCVRs).

The antigen-binding molecules (e.g., bispecific antigen-binding molecules) of the present invention are useful, inter alia, for targeting cells that express LEPR and/or cells that express GP130, or both. According to certain embodiments, the bispecific antigen-binding molecules of the present invention are useful for physically linking LEPR and GP130 to one another on the surface of a cell in order to stimulate LEPR signaling. In this manner, the bispecific antigen binding molecules of the present invention may serve as LEPR agonists in a variety of therapeutic applications where leptin and/or LEPR-mediated signaling would be beneficial (e.g., in the treatment of obesity, lipodystrophies and other diseases and disorders associated with or caused by leptin deficiency or leptin resistance).

Other embodiments will become apparent from a review of the ensuing detailed description.

BRIEF DESCRIPTION OF THE FIGURES

FIG. 1 shows the effects of LEPR×GP130 bispecific antibody treatment (open squares and open diamonds) on obese mice, fed a high fat diet, expressing human LEPR and human GP130, compared to treatment with isotype control antibody (closed circles). Antibodies were administered subcutaneously at 30 mg/kg on day 0 and day 7 (indicated by "Dose" and upward arrows), and the effects of antibody treatment on body weight (expressed in terms of average percent change in body weight from pre-dose) are plotted over time for each treatment group over time. Open squares represent mice treated with bsAb21236 (alternatively referred to as "H4H21236D"). Open diamonds represent mice treated with bsAb21237 (alternatively referred to as "H4H21237D"). (*) indicates P<0.05 isotype control vs. bsAb21236. (#) indicates P<0.05 isotype control vs. bsAb21237.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

GP130 Protein

The expressions "Glycoprotein 130," "GP130," "gp130," and the like, as used herein, refer to the human GP130 protein comprising the amino acid sequence as set forth in SEQ ID NO:185 (see also UniProtKB Q17RA0). The expression "GP130" includes both monomeric and multimeric GP130 molecules. As used herein, the expression "monomeric human GP130" means a GP130 protein or portion thereof that does not contain or possess any multimerizing domains and that exists under normal conditions as a single GP130 molecule without a direct physical connection to another GP130 molecule. An exemplary monomeric GP130 molecule is the molecule referred to herein as "hGP130.mmh" comprising the amino acid sequence of SEQ ID NO:191 (see, e.g., Example 3, herein). As used herein, the expression "dimeric human GP130" means a construct comprising two GP130 molecules connected to one another through a linker, covalent bond, non-covalent bond, or through a multimerizing domain such as an antibody Fc domain. An exemplary dimeric GP130 molecule is the molecule referred to herein as "hGP130.hFc" comprising the amino acid sequence of SEQ ID NO:197 or "hGP130.mFc" comprising the amino acid sequence of SEQ ID NO:190 (see, e.g., Example 3, herein).

All references to proteins, polypeptides and protein fragments herein are intended to refer to the human version of the respective protein, polypeptide or protein fragment unless explicitly specified as being from a non-human species. Thus, the expression "GP130" means human GP130 unless specified as being from a non-human species, e.g., "mouse GP130," "monkey GP130," etc.

As used herein, the expression "cell surface-expressed GP130" means one or more GP130 protein(s), or the extracellular domain thereof, that is/are expressed on the surface of a cell in vitro or in vivo, such that at least a portion of a GP130 protein is exposed to the extracellular side of the cell membrane and is accessible to an antigen-binding portion of an antibody. A "cell surface-expressed GP130" can comprise or consist of a GP130 protein expressed on the surface of a cell which normally expresses GP130 protein. Alternatively, "cell surface-expressed GP130" can comprise or consist of GP130 protein expressed on the surface of a cell that normally does not express human GP130 on its surface but has been artificially engineered to express GP130 on its surface.

Anti-GP130 Antibodies and Antigen-Binding Fragments Thereof

According to one aspect of the present invention, anti-GP130 antibodies are provided (e.g., monospecific anti-GP130 antibodies). Exemplary anti-GP130 antibodies according to this aspect of the invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-GP130 antibodies from which the bispecific antigen-binding molecules of the present invention may be derived. Table 2 sets forth the nucleic acid sequence identifiers of the HCVRs, LCVRs, HCDR1, HCDR2 HCDR3, LCDR1, LCDR2 and LCDR3 of the exemplary anti-GP130 antibodies.

The present invention provides antibodies or antigen-binding fragments thereof that specifically bind GP130, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind GP130, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind GP130, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-GP130 antibodies listed in Table 1. In certain embodiments, the HCVR/LCVR amino acid sequence pair is SEQ ID NOs: 154/10.

The present invention also provides antibodies or antigen-binding fragments thereof that specifically bind GP130, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind GP130, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind GP130, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind GP130, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind GP130, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind GP130, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind GP130, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-GP130 antibodies listed in Table 1. In certain embodiments, the HCDR3/LCDR3 amino acid sequence pair is SEQ ID NOs: 160/16.

The present invention also provides antibodies or antigen-binding fragments thereof that specifically bind GP130, comprising a set of six CDRs (i.e., HCDR1-HCDR2-HCDR3-LCDR1-LCDR2-LCDR3) contained within any of the exemplary anti-GP130 antibodies listed in Table 1. In certain embodiments, the HCDR1-HCDR2-HCDR3-LCDR1-LCDR2-LCDR3 amino acid sequences set is selected from the group consisting of: SEQ ID NOs: 20-22-24-12-14-16, 28-30-32-12-14-16, 36-38-40-12-14-16, 44-46-48-12-14-16, 52-54-56-12-14-16, 60-62-64-12-14-16, 68-70-72-12-14-16, 76-78-80-12-14-16, 84-86-88-12-14-16, 92-94-96-12-14-16, 100-102-104-12-14-16, 108-110-112-12-14-16, 116-118-120-12-14-16, 124-126-128-12-14-16, 132-134-136-12-14-16, 140-142-144-12-14-16, 148-150-152-12-14-16 and 156-158-160-12-14-16.

In a related embodiment, the present invention provides antibodies, or antigen-binding fragments thereof that specifically bind GP130, comprising a set of six CDRs (i.e., HCDR1-HCDR2-HCDR3-LCDR1-LCDR2-LCDR3) contained within an HCVR/LCVR amino acid sequence pair as defined by any of the exemplary anti-GP130 antibodies listed in Table 1. For example, the present invention includes antibodies or antigen-binding fragments thereof that specifically bind GP130, comprising the HCDR1-HCDR2-HCDR3-LCDR1-LCDR2-LCDR3 amino acid sequences set contained within an HCVR/LCVR amino acid sequence pair of: SEQ ID NOs: 154/10.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides nucleic acid molecules encoding anti-GP130 antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-GP130 antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-GP130 antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-GP130 antibody listed in Table 1.

The present invention also provides recombinant expression vectors capable of expressing a polypeptide comprising a heavy or light chain variable region of an anti-GP130 antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

The present invention includes anti-GP130 antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

LEPR Protein

The expression "leptin receptor," "LEPR," and the like, as used herein, refers to the human leptin receptor, comprising the amino acid sequence as set forth in SEQ ID NO:186 (see also UniProtKB/Swiss-Prot Accession No. P48357). Alternative names for LEPR used in the scientific literature include "OB receptor," "OB-R," and "CD295." LEPR is also referred to as "WSX" (see, e.g., U.S. Pat. No. 7,524,937). The expression "LEPR" includes both monomeric and multimeric LEPR molecules. As used herein, the expression "monomeric human LEPR" means a LEPR protein or portion thereof that does not contain or possess any multimerizing domains and that exists under normal conditions as a single LEPR molecule without a direct physical connection to another LEPR molecule. An exemplary monomeric LEPR molecule is the molecule referred to herein as "hLEPR.mmh" comprising the amino acid sequence of SEQ ID NO:187 (see, e.g., Example 10, herein). As used herein, the expression "dimeric human LEPR" means a construct comprising two LEPR molecules connected to one another through a linker, covalent bond, non-covalent bond, or through a multimerizing domain such as an antibody Fc domain. An exemplary dimeric LEPR molecule is the molecule referred to herein as "hLEPR.hFc" comprising the amino acid sequence of SEQ ID NO:189 (see, e.g., Example 10, herein).

All references to proteins, polypeptides and protein fragments herein are intended to refer to the human version of the respective protein, polypeptide or protein fragment unless explicitly specified as being from a non-human species. Thus, the expression "LEPR" means human LEPR unless specified as being from a non-human species, e.g., "mouse LEPR," "monkey LEPR," etc.

As used herein, the expression "cell surface-expressed LEPR" means one or more LEPR protein(s), or the extracellular domain thereof, that is/are expressed on the surface of a cell in vitro or in vivo, such that at least a portion of a LEPR protein is exposed to the extracellular side of the cell membrane and is accessible to an antigen-binding portion of an antibody. A "cell surface-expressed LEPR" can comprise or consist of a LEPR protein expressed on the surface of a cell which normally expresses LEPR protein. Alternatively, "cell surface-expressed LEPR" can comprise or consist of LEPR protein expressed on the surface of a cell that normally does not express human LEPR on its surface but has been artificially engineered to express LEPR on its surface.

Several isoforms of the LEPR are generated through alternative splicing, resulting in a long isoform b (LEPR-b) and several short forms, including isoform a (LEPR-a) which shows the highest and broadest expression pattern (Tartaglia L A. The leptin receptor. J Biol Chem 1997; 272: 6093-6096). LEPR-b is the predominant isoform expressed in the brain, while LEPR-a is broadly expressed in the liver. All the isoforms share the same extracellular domain, transmembrane region and a short stretch of the cytoplasmic domain, containing the Box 1 region, followed by a variable region. The long form contains intracellular sequence motifs required for mediating all the signaling capabilities of leptin whereas the short forms are lacking these regions. The extracellular domain of the short forms is identical to the signaling competent long form.

LEPR×GP130 Bispecific Antigen-Binding Molecules

The present invention is based on the concept of stimulating LEPR and GP130 signaling by bridging LEPR and GP130 on the surface of a cell. In particular, the present invention relates to the premise that a bispecific antigen-binding molecule, such as a LEPR×GP130 bispecific antibody (as described in detail elsewhere herein), is capable of stimulating LEPR-dependent signaling of STAT3 by bringing GP130 into relative proximity of the leptin receptor on the surface of cells, even in the absence leptin. In this manner, the bispecific antigen-binding molecules of the present invention may serve as LEPR agonists which may find use in therapeutic contexts where induced leptin/LEPR signaling is beneficial and/or desirable.

Accordingly, the present invention provides bispecific antigen binding molecules comprising a first antigen-binding domain (also referred to herein as "D1") that binds human GP130, and a second antigen-binding domain (also referred to herein as "D2") that binds human LEPR. According to the present invention, and as demonstrated in the working examples herein, the simultaneous binding LEPR and GP130 by the bispecific antigen-binding molecules of the invention results in stimulation of LEPR signaling.

The bispecific antigen-binding molecules of the present invention, may be referred to herein as "LEPR×GP130 bispecific antibodies," or other related terminology.

LEPR×GP130 bispecific antigen-binding molecules of the present invention may be constructed using the antigen-binding domains derived from mono-specific (conventional) anti-LEPR antibodies and anti-GP130 antibodies. For example, a collection of monoclonal, monospecific, anti-LEPR and/or anti-GP130 antibodies may be produced using standard methods known in the art, and the antigen-binding domains thereof can be used to construct LEPR×GP130 bispecific antigen-binding molecules (e.g., bispecific antibodies) using conventional techniques known in the art.

Exemplary anti-LEPR antibodies that can be used in the context of the present invention to produce LEPR×GP130 bispecific antigen binding molecules include any of the anti-LEPR antibodies described in US Patent Application Publication No. 2017/0101477, the disclosure of which is incorporated herein in its entirety. Anti-LEPR antibodies that can be used to construct the LEPR×GP130 bispecific antigen-binding molecules of the present invention may be agonist antibodies, i.e., antibodies that bind human LEPR and activate LEPR signaling. In other embodiments, anti-LEPR antibodies that can be used to construct LEPR×GP130 bispecific antigen-binding molecules may be potentiating antibodies, i.e., antibodies that enhance leptin-mediated signaling through LEPR. Anti-LEPR antibodies that are useful for constructing LEPR×GP130 bispecific antigen-binding molecules may be antibodies that are able to bind LEPR in complexed with leptin. Such antibodies include those that bind LEPR and do not block the LEPR:leptin interaction. Alternatively, anti-LEPR antibodies that are useful for constructing LEPR×GP130 bispecific antigen-binding molecules may be antibodies that compete with leptin for binding to LEPR, and/or only bind LEPR in the absence of leptin. Non-limiting examples of particular anti-LEPR antibodies that can be used to construct LEPR×GP130 bispecific antigen-binding molecules include the anti-LEPR antibodies referred to herein as "mAb18445" and "mAb18446".

In some embodiments, the LEPR×GP130 bispecific antigen-binding molecule is derived from an anti-LEPR antibody that potentiates leptin-mediated signaling in vitro through the LEPR-b isoform.

In some embodiments, the LEPR×GP130 bispecific antigen-binding molecule is derived from an anti-LEPR antibody that does not activate leptin-mediated signaling in vitro through the LEPR-a isoform.

Exemplary anti-GP130 antibodies that can be used in the context of the present invention to produce LEPR×GP130 bispecific antigen binding molecules include any of the anti-GP130 antibodies described elsewhere herein. Anti-GP130 antibodies that are useful for constructing LEPR×GP130 bispecific antigen-binding molecules include anti-GP130 antibodies with one or more of the following properties: binds monkey GP130, does not bind mouse or rat GP130, binds to an epitope within the FNIII domain of GP130, does not inhibit GP130 ligand-mediated signaling, and/or does not activate GP130 signaling in the absence of a GP130 ligand. GP130 ligands include, e.g., human oncostatin M (OSM), human leukemia inhibitory factor (LIF), and human ciliary neurotrophic factor (CNTF). A non-limiting example of a particular anti-GP130 antibody that can be used to construct LEPR×GP130 bispecific antigen-binding molecules include the anti-GP130 antibody referred to herein as "mAb16683".

According to the present invention, a bispecific antigen-binding molecule can be a single multifunctional polypeptide, or it can be a multimeric complex of two or more polypeptides that are covalently or non-covalently associated with one another. As will be made evident by the present disclosure, any antigen binding construct which has an antigen-binding domain that specifically binds human LEPR and an antigen-binding domain that specifically binds human GP130 is regarded as a "bispecific antigen-binding molecule." Any of the bispecific antigen-binding molecules of the invention, or variants thereof, may be constructed using standard molecular biological techniques (e.g., recombinant DNA and protein expression technology), as will be known to a person of ordinary skill in the art.

The bispecific antigen-binding molecules of the invention may be "isolated." An "isolated bispecific antigen-binding molecule," as used herein, means a bispecific antigen-binding molecule that has been identified and separated and/or recovered from at least one component of its natural environment. For example, a bispecific antibody that has been separated or removed from at least one component of an organism, or from a tissue or cell in which the antibody is produced, is an "isolated bispecific antibody" for purposes of the present invention. An isolated bispecific antigen-binding molecule also includes molecules in situ within a recombinant cell. Isolated bispecific antigen-binding molecules are molecules that have been subjected to at least one purification or isolation step. According to certain embodiments, an isolated bispecific antigen-binding molecule may be substantially free of other cellular material and/or chemicals.

Antigen-Binding Domains

The bispecific antigen-binding molecules of the present invention comprise two separate antigen-binding domains (D1 and D2). As used herein, the expression "antigen-binding domain" means any peptide, polypeptide, nucleic acid molecule, scaffold-type molecule, peptide display molecule, or polypeptide-containing construct that is capable of specifically binding a particular antigen of interest (e.g., human LEPR or human GP130). The term "specifically binds" or the like, as used herein in reference to an antigen-binding domain, means that the antigen-binding domain is capable of forming a complex with a particular antigen and does not bind other unrelated antigens under ordinary test conditions. "Unrelated antigens" are proteins, peptides or polypeptides that have less than 95% amino acid identity to one another.

Exemplary categories of antigen-binding domains that can be used in the context of the present invention include antibodies, antigen-binding portions of antibodies, peptides that specifically interact with a particular antigen (e.g., peptibodies), receptor molecules that specifically interact with a particular antigen, proteins comprising a ligand-binding portion of a receptor that specifically binds a particular antigen, antigen-binding scaffolds (e.g., DARPins, HEAT repeat proteins, ARM repeat proteins, tetratricopeptide repeat proteins, and other scaffolds based on naturally occurring repeat proteins, etc., [see, e.g., Boersma and Plückthun, 2011, *Curr. Opin. Biotechnol.* 22:849-857, and references cited therein]), and aptamers or portions thereof.

Methods for determining whether two molecules specifically bind one another are well known in the art and include, for example, equilibrium dialysis, surface plasmon resonance, and the like. The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, NJ).

As indicated above, an "antigen-binding domain" (D1 and/or D2) may comprise or consist of an antibody or antigen-binding fragment of an antibody. The term "antibody," as used herein, means any antigen-binding molecule or molecular complex comprising at least one complementarity determining region (CDR) that specifically binds to or interacts with a particular antigen (e.g., human MET). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the antibodies of the invention (or antigen-binding portion thereof) may be identical to the human germline sequences, or may be naturally or artificially modified. An amino acid consensus sequence may be defined based on a side-by-side analysis of two or more CDRs.

The D1 and/or D2 components of the bispecific antigen-binding molecules of the present invention may comprise or consist of antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The bispecific antigen-binding molecules of the present invention may comprise or consist of human antibodies and/or recombinant human antibodies, or fragments thereof. The term "human antibody", as used herein, includes antibodies having variable and constant regions derived from human germline immunoglobulin sequences. Human antibodies may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The bispecific antigen-binding molecules of the present invention may comprise or consist of recombinant human antibodies or antigen-binding fragments thereof. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Methods for making bispecific antibodies are known in the art and may be used to construct bispecific antigen-binding molecules of the present invention. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and $Mab^2$ bispecific formats (see, e.g., Klein et al. 2012, mAbs 4:6, 1-11, and references cited therein, for a review of the foregoing formats).

Exemplary antigen-binding domains (D1 and D2) that can be included in the LEPR×GP130 bispecific antigen-binding molecules of the present invention include antigen-binding domains derived from any of the anti-LEPR and/or anti-GP130 antibodies disclosed herein or otherwise known in the art.

For example, the present invention includes LEPR× GP130 bispecific antigen-binding molecules comprising a D1 (GP130-binding) antigen-binding domain comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides LEPR×GP130 bispecific antigen-binding molecules comprising a D1 (GP130-binding) antigen-binding domain comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides LEPR×GP130 bispecific antigen-binding molecules comprising a D1 (GP130-binding) antigen-binding domain comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides LEPR×GP130 bispecific antigen-binding molecules comprising a D1 (GP130-binding) domain comprising an HCVR/LCVR amino acid sequence pair contained within any of the exemplary anti-MET antibodies listed in Table 1.

The present invention also provides LEPR×GP130 bispecific antigen-binding molecules comprising a D1 (GP130-binding) antigen-binding domain comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides LEPR×GP130 bispecific antigen-binding molecules comprising a D1 (GP130-binding) antigen-binding domain comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides LEPR×GP130 bispecific antigen-binding molecules comprising a D1 (GP130-binding) antigen-binding domain comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides LEPR×GP130 bispecific antigen-binding molecules comprising a D1 (GP130-binding) antigen-binding domain comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides LEPR×GP130 bispecific antigen-binding molecules comprising a D1 (GP130-binding) antigen-binding domain comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides LEPR×GP130 bispecific antigen-binding molecules comprising a D1 (GP130-binding) antigen-binding domain comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides LEPR×GP130 bispecific antigen-binding molecules comprising a D1 (GP130-binding) antigen-binding domain comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-MET antibodies listed in Table 1.

The present invention also provides LEPR×GP130 bispecific antigen-binding molecules comprising a D1 (GP130-binding) antigen-binding domain comprising a set of six CDRs (i.e., HCDR1-HCDR2-HCDR3-LCDR1-LCDR2-LCDR3) contained within any of the exemplary anti-MET antibodies listed in Table 1.

In a related embodiment, the present invention provides LEPR×GP130 bispecific antigen-binding molecules comprising a D1 (GP130-binding) antigen-binding domain comprising a set of six CDRs (i.e., HCDR1-HCDR2-HCDR3-LCDR1-LCDR2-LCDR3) contained within an HCVR/LCVR amino acid sequence pair as defined by any of the exemplary anti-MET antibodies listed in Table 1.

The present invention includes LEPR×GP130 bispecific antigen-binding molecules comprising a D2 (LEPR-binding) antigen-binding domain comprising a variable domain (HCVR and/or LCVR), and/or complementary determining region (HCDR1, HCDR2, HCDR3, LCDR1, LCDR2, and/or LCDR3), derived from any of the anti-LEPR antibodies described herein, described in US Patent Application Publication No. 2017/0101477, the disclosure of which is incorporated herein in its entirety, or otherwise known in the art.

As non-limiting illustrative examples, the present invention includes LEPR×GP130 bispecific antigen binding molecules comprising a D1 (GP130-binding) antigen-binding domain and a D2 (LEPR-binding) antigen-binding domain, wherein the D1 antigen binding domain comprises an HCVR/LCVR amino acid sequence pair of SEQ ID NOs: 154/10, or a set of heavy and light chain CDRs (HCDR1-HCDR2-HCDR3-LCDR1-LCDR2-LCDR3) comprising SEQ ID NOs: 156-158-160-12-14-16, and wherein the D2 (LEPR-binding) antigen-binding domain comprises an HCVR/LCVR amino acid sequence pair of SEQ ID NOs: 170/10 or 178/10, or a set of heavy and light chain CDRs (HCDR1-HCDR2-HCDR3-LCDR1-LCDR2-LCDR3) comprising SEQ ID NOs: 172-174-176-12-14-16, or 180-182-184-12-14-16. An exemplary LEPR×GP130 bispecific antibody having these sequence characteristics is the bispecific antibody designated bsAb21236, which comprises a D1 derived from mAb16683 and a D2 derived from mAb18445. Another exemplary LEPR×GP130 bispecific antibody having these sequence characteristics is the bispecific antibody designated bsAb21237, which comprises a D1 derived from mAb16683 and a D2 derived from mAb18446. Other specific examples of bispecific antibodies of the present invention are set forth in Example 9, Table 20 herein.

Multimerizing Components

The bispecific antigen-binding molecules of the present invention, in certain embodiments, may also comprise one or more multimerizing component(s). The multimerizing components can function to maintain the association between the antigen-binding domains (D1 and D2). As used herein, a "multimerizing component" is any macromolecule, protein, polypeptide, peptide, or amino acid that has the ability to associate with a second multimerizing component of the same or similar structure or constitution. For example, a multimerizing component may be a polypeptide comprising an immunoglobulin $C_H3$ domain. A non-limiting example of a multimerizing component is an Fc portion of an immunoglobulin, e.g., an Fc domain of an IgG selected from the isotypes IgG1, IgG2, IgG3, and IgG4, as well as any allotype within each isotype group. In certain embodiments, the multimerizing component is an Fc fragment or an amino acid sequence of 1 to about 200 amino acids in length containing at least one cysteine residues. In other embodiments, the multimerizing component is a cysteine residue, or a short cysteine-containing peptide. Other multimerizing domains include peptides or polypeptides comprising or consisting of a leucine zipper, a helix-loop motif, or a coiled-coil motif.

In certain embodiments, the bispecific antigen-binding molecules of the present invention comprise two multimerizing domains, M1 and M2, wherein D1 is attached to M1 and D2 is attached to M2, and wherein the association of M1 with M2 facilitates the physical linkage of D1 and D2 to one another in a single bispecific antigen-binding molecule. In certain embodiments, M1 and M2 are identical to one another. For example, M1 can be an Fc domain having a particular amino acid sequence, and M2 is an Fc domain with the same amino acid sequence as M1. Alternatively, M1 and M2 may differ from one another at one or more amino acid position. For example, M1 may comprise a first immunoglobulin (Ig) $C_H3$ domain and M2 may comprise a second Ig $C_H3$ domain, wherein the first and second Ig $C_H3$ domains differ from one another by at least one amino acid, and wherein at least one amino acid difference reduces binding of the targeting construct to Protein A as compared to a reference construct having identical M1 and M2 sequences. In one embodiment, the Ig $C_H3$ domain of M1 binds Protein A and the Ig $C_H3$ domain of M2 contains a mutation that reduces or abolishes Protein A binding such as an H95R modification (by IMGT exon numbering; H435R by EU numbering). The $C_H3$ of M2 may further comprise a Y96F modification (by IMGT; Y436F by EU). Further modifications that may be found within the $C_H3$ of M2 include: D16E, L18M, N44S, K52N, V57M, and V82I (by IMGT; D356E, L358M, N384S, K392N, V397M, and V422I by EU) in the case of an IgG1 Fc domain; N44S, K52N, and V82I (IMGT; N384S, K392N, and V422I by EU) in the case of an IgG2 Fc domain; and Q15R, N44S, K52N, V57M, R69K, E79Q, and V82I (by IMGT; Q355R, N384S, K392N, V397M, R409K, E419Q, and V422I by EU) in the case of an IgG4 Fc domain.

Variants

The bispecific antigen-binding molecules disclosed herein, or the antigen-binding domains thereof (D1 and/or D2) may comprise one or more amino acid substitutions, insertions and/or deletions in the framework and/or CDR regions of the heavy and light chain variable domains as compared to the corresponding germline sequences from which the antigen-binding proteins or antigen-binding domains were derived. Such mutations can be readily ascertained by comparing the amino acid sequences disclosed herein to germline sequences available from, for example, public antibody sequence databases. The present invention includes bispecific antigen-binding molecules disclosed herein, or the antigen-binding domains thereof (D1 and/or D2), which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous bispecific antigen-binding molecules, or antigen-binding domains thereof (D1 and/or D2), which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the bispecific antigen-binding molecules, or the antigen-binding domains thereof (D1 and/or D2), of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, bispecific antigen-binding molecules, or the antigen-binding domains thereof (D1 and/or D2), that contain one or more germline mutations can be easily tested for one or more desired property such as, improved binding specificity, increased binding affinity, improved or enhanced antagonistic or agonistic biological properties (as the case may be), reduced immunogenicity, etc. bispecific antigen-binding molecules, or the antigen-binding domains thereof (D1 and/or D2), obtained in this general manner are encompassed within the present invention.

The present invention also includes anti-LEPR antibodies, anti-GP130 antibodies, and bispecific antigen-binding molecules comprising variants of any of the HCVR, LCVR, and/or CDR amino acid sequences disclosed herein. Exemplary variants included within this aspect of the invention include variants of any of the HCVR, LCVR, and/or CDR amino acid sequences disclosed herein having one or more conservative substitutions. For example, the present invention includes anti-LEPR antibodies, anti-GP130 antibodies, and LEPR×GP130 bispecific antigen-binding molecules having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set herein.

Exemplary variants included within this aspect of the invention also include variants having substantial sequence identity to any of the HCVR, LCVR, and/or CDR amino acid sequences disclosed herein. As used herein in the context of amino acid sequences, the term "substantial identity" or "substantially identical" means that two amino acid sequences, when optimally aligned, such as by the programs GAP or BESTFIT using default gap weights, share at least 95%, 98% or 99% sequence identity. In certain embodiments, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence identity between two different amino acid sequences is typically measured using sequence analysis software. Sequence analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

LEPR×GP130 Bispecific Antigen-Binding Molecules Comprising Fc Variants

According to certain embodiments of the present invention, LEPR×GP130 bispecific antigen binding proteins are provided comprising an Fc domain comprising one or more mutations which enhance or diminish antibody binding to the FcRn receptor, e.g., at acidic pH as compared to neutral pH. For example, the present invention includes LEPR×GP130 bispecific antigen binding proteins comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428 L (e.g., M428L) and 434S (e.g., N434S) modification; a 428 L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes LEPR×GP130 bispecific antigen binding proteins comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the LEPR×GP130 Antigen-Binding Molecules of the Invention The present invention includes LEPR×GP130 bispecific antigen-binding molecules that bind human LEPR with high affinity. For example, the present invention includes LEPR× GP130 antigen-binding molecules that bind monomeric human LEPR (e.g., hLEPR.mmh) with a $K_D$ of less than about 110 nM as measured by surface plasmon resonance at 25° C., e.g., using an assay format as defined in Example 10 herein, or a substantially similar assay. According to certain embodiments, LEPR×GP130 bispecific antigen-binding molecules are provided that bind monomeric human LEPR (e.g., hLEPR.mmh) with a dissociative half-life ($t_{1/2}$) of greater than about 3 minutes as measured by surface plasmon resonance at 25° C., e.g., using an assay format as defined int Example 10 herein, or a substantially similar assay.

The present invention includes LEPR×GP130 bispecific antigen-binding molecules that bind human GP130 with high affinity. For example, the present invention includes LEPR×GP130 antigen-binding molecules that bind monomeric human GP130 (e.g., hGP130.mmh) with a $K_D$ of less than about 150 nM as measured by surface plasmon resonance at 25° C., e.g., using an assay format as defined in Example 10 herein, or a substantially similar assay. According to certain embodiments, LEPR×GP130 bispecific antigen-binding molecules are provided that bind monomeric human GP130 (e.g., hGP130.mmh) with a dissociative half-life ($t_{1/2}$) of greater than about 2.5 minutes as measured by surface plasmon resonance at 25° C., e.g., using an assay format as defined in Example 10 herein, or a substantially similar assay.

The present invention includes LEPR×GP130 bispecific antigen-binding molecules that are capable of binding cells that express human LEPR. In some aspects, the LEPR× GP130 bispecific antigen-binding molecules are capable of binding cells that express human LEPR, isoform b. In certain embodiments, LEPR×GP130 bispecific antigen-binding proteins are provided that bind cells expressing human LEPR in the presence and/or absence of leptin. The present invention includes LEPR×GP130 bispecific antigen-binding molecules that are capable of binding cells that express human GP130. Cell binding by a bispecific antigen-binding molecule of the present invention may be assessed by fluorescence activated cell sorting (FACS) on cells expressing LEPR and or GP130, e.g., using an assay format as defined in Example 11 herein, or a substantially similar assay.

The present invention includes LEPR×GP130 bispecific antigen-binding molecules that activate GP130-mediated cell signaling. In certain embodiments, the present invention includes LEPR×GP130 bispecific antigen-binding molecules that activate GP130-mediated cell signaling with a potency that is at least 20% the degree of activation observed by treatment with a GP130 ligand. For example, the present invention includes LEPR×GP130 bispecific antigen-binding molecules that activate GP130-mediated cell signaling with a potency that is at least 20% or 25% the degree of activation observed by treatment with human oncostatin M (OSM) under the same or similar experimental assay condition. Activation of GP130-mediated cell signaling by a bispecific antigen-binding molecule of the present invention may be assessed by an in vitro cell signaling assay, e.g., using an assay format as defined in Example 12 herein, or a substantially similar assay.

The present invention includes LEPR×GP130 bispecific antigen-binding molecules that specifically, or preferentially, activate signaling through LEPR isoform 'b' (long form) and do not substantially activate signaling through LEPR isoform 'a' (short form). According to certain embodiments, LEPR×GP130 bispecific antigen-binding molecules are provided that specifically, or preferentially, potentiate leptin signaling through LEPR isoform 'b' (long form) and do not substantially potentiate leptin signaling through LEPR isoform 'a' (short form). Activation or potentiating of signaling through LEPR isoform 'b' and/or LEPR isoform 'a' may be assessed by an in vitro assay using a reporter cell line that specifically expresses LEPR isoform 'b' or LEPR isoform 'a', e.g., using an assay format as defined in Example 14 herein, or a substantially similar assay.

The present invention includes LEPR×GP130 bispecific antigen-binding molecules that cause a reduction in body weight when administered to an animal. For example, the present invention includes LEPR×GP130 bispecific antigen-binding molecules that cause a 1% to 4% reduction in body weight in animals 2 to 14 days following administration of the bispecific antigen-binding molecule in a therapeutically effective dose to the animal. Weight loss induction by the bispecific antigen-binding molecules of the invention may be assessed using a genetically engineered model system, e.g., using an in vivo model as set forth in Example 13 herein, or a substantially similar model.

The bispecific antigen-binding molecules of the present invention may possess one or more of the aforementioned biological characteristics, or any combination thereof. The foregoing list of biological characteristics of the bispecific antigen-binding molecules of the invention is not intended to be exhaustive. Other biological characteristics of the bispecific antigen-binding molecules of the present invention will be evident to a person of ordinary skill in the art from a review of the present disclosure including the working Examples herein.

Epitope Mapping, Binding Domains, and Related Technologies

The epitope to which the antibodies and antigen-binding domains of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a LEPR or GP130 protein. Alternatively, the relevant epitope may consist of a plurality of non-contiguous amino acids (or amino acid sequences) of the target protein.

Various techniques known to persons of ordinary skill in the art can be used to determine the epitope on LEPR and/or GP130 with which the antibodies and antigen-binding domains of the present invention interact. Exemplary techniques that can be used to determine an epitope or binding domain of a particular antibody or antigen-binding domain include, e.g., point mutagenesis (e.g., alanine scanning mutagenesis, arginine scanning mutagenesis, etc.), peptide blots analysis (Reineke, 2004, Methods Mol Biol 248:443-463), protease protection, and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/ deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystal structure analysis can also be used to identify the amino acids within a polypeptide with which an antibody interacts.

The present invention includes LEPR×GP130 bispecific antigen-binding molecules comprising a D1 (GP130-binding) domain that binds to the same epitope as any of the specific exemplary anti-GP130 antibodies or antigen-binding domains described herein (e.g. antibodies comprising any of the amino acid sequences as set forth in Table 1 herein). The present invention includes LEPR×GP130 bispecific antigen-binding molecules comprising a D2 (LEPR-binding) domain that binds to the same epitope as any of the specific exemplary anti-LEPR antibodies or antigen-binding domains described herein (e.g. antibodies comprising any of the amino acid sequences as set forth in Table 18 herein). Likewise, the present invention also includes LEPR×GP130 bispecific antigen-binding molecules comprising a D1 (GP130-binding) domain that competes for binding to GP130 with any of the specific exemplary anti-GP130 antibodies described herein (e.g. antibodies comprising any of the amino acid sequences as set forth in Table 1 herein). Moreover, the present invention also includes LEPR×GP130 bispecific antigen-binding molecules comprising a D2 (LEPR-binding) domain that competes for binding to LEPR with any of the specific exemplary anti-LEPR antibodies described herein (e.g. antibodies comprising any of the amino acid sequences as set forth in Table 18 herein).

One can easily determine whether an antibody or antigen-binding domain binds to the same epitope as, or competes for binding with, a reference anti-GP130 or anti-LEPR antibody by using routine methods known in the art and exemplified herein. For example, to determine if a test antibody binds to the same epitope as a reference anti-GP130 or anti-LEPR antibody of the invention, the reference antibody is allowed to bind to a target molecule (i.e., GP130 or LEPR protein, as the case may be). Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies are deemed to bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-GP130 or anti-LEPR antibody, the above-described binding methodology is performed in two orientations: In a first orientation, the reference antibody is allowed to bind to the target molecule under saturating conditions followed by assessment of binding of the test antibody to the target molecule. In a second orientation, the test antibody is allowed to bind to a target molecule under saturating conditions followed by assessment of binding of the reference antibody to the target molecule. If, in both orientations, only the first (saturating) antibody is capable of binding to the target molecule, then it is concluded that the test antibody and the reference antibody compete for binding to the target molecule. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

The antigen-binding domains (D1 and/or D2) of the bispecific antigen-binding molecules of the present invention may be described in terms of the domains of GP130 or LEPR with which the antigen-binding domain interacts. GP130 and LEPR proteins comprise various domains referred to as D1, D2, D3 and FNIII. Accordingly, the D1 and D2 antigen-binding domains of the bispecific antigen-binding molecules of the present invention, may bind a domain of LEPR or GP130 selected from the group consisting of D1, D2, D3, or FNIII. According to certain exemplary embodiments, LEPR×GP130 bispecific antigen binding molecules are provided wherein the D1 (anti-GP130) antigen-binding domain binds to the FNIII domain of GP130, and the D2 (anti-LEPR) antigen-binding domain binds to the FNIII domain of LEPR. Other binding domain combinations are contemplated within the scope of the present invention.

Preparation of Human Antibodies

The anti-GP130, anti-LEPR antibodies, and LEPR× GP130 bispecific antibodies of the present invention can be fully human antibodies. Methods for generating monoclonal antibodies, including fully human monoclonal antibodies are known in the art. Any such known methods can be used in the context of the present invention to make human antibodies that specifically bind to human GP130 and/or human LEPR.

Using VELOCIMMUNE™ technology, for example, or any other similar known method for generating fully human monoclonal antibodies, high affinity chimeric antibodies to human GP130 and/or human LEPR are initially isolated having a human variable region and a mouse constant region. As in the experimental section below, the antibodies are characterized and selected for desirable characteristics, including affinity, ligand blocking activity, selectivity, epitope, etc. If necessary, mouse constant regions are replaced with a desired human constant region, for example wild-type or modified IgG1 or IgG4, to generate fully human anti-GP130 and/or anti-LEPR antibodies. While the constant region selected may vary according to specific use, high affinity antigen-binding and target specificity characteristics reside in the variable region. In certain instances, fully human anti-GP130 and/or anti-LEPR antibodies are isolated directly from antigen-positive B cells.

Bioequivalents

The present invention includes variant anti-GP130, anti-LEPR antibodies, and LEPR×GP130 bispecific antibodies having amino acid sequences that vary from those of the described antibodies but that retain the ability to bind the relevant target antigen(s) (GP130 and/or LEPR) and exert one or more of the biological function(s) of the parent antibodies from which such variants are derived. Such variant antibodies and antibody fragments comprise one or more additions, deletions, or substitutions of amino acids when compared to parent sequence, but exhibit biological activity that is essentially equivalent to that of the described antibodies. Likewise, the present invention includes DNA sequences encoding anti-GP130, anti-LEPR antibodies, and LEPR×GP130 bispecific antibodies of the present invention, wherein such DNA sequences comprise one or more additions, deletions, or substitutions of nucleotides when compared to the disclosed parental sequence, but that encode anti-GP130, anti-LEPR antibodies, and LEPR×GP130 bispecific antibodies that are essentially bioequivalent to the exemplary antibodies disclosed herein. Examples of such variant amino acid and DNA sequences are discussed elsewhere herein.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Species Selectivity and Species Cross-Reactivity

The present invention, according to certain embodiments, provides anti-GP130, anti-LEPR antibodies, and LEPR× GP130 bispecific antibodies (and other antigen-binding molecules comprising anti-GP130 and/or anti-LEPR antigen-binding domains) that bind to human GP130 and human LEPR but not to the corresponding proteins from other species. The present invention also includes anti-GP130, anti-LEPR antibodies, and LEPR×GP130 bispecific antibodies (and antigen-binding molecules comprising anti-GP130 and/or anti-LEPR antigen-binding domains) that bind to human GP130 and human LEPR and to GP130 and LEPR from one or more non-human species. For example, the present invention includes bispecific antigen-binding molecules comprising a first and second antigen-binding domain, wherein the first antigen binding domain binds human and monkey (e.g., *Macaca fascicularis*) GP130 but does not bind rodent (rat and/or mouse) GP130. The present invention includes bispecific antigen-binding molecules comprising a first and second antigen-binding domain, wherein the second antigen binding domain binds human and monkey (e.g., *Macaca fascicularis*) LEPR but does not bind rodent (rat and/or mouse) LEPR.

The present invention further provides anti-GP130, anti-LEPR antibodies, and LEPR×GP130 bispecific antibodies (and other antigen-binding molecules comprising anti-GP130 and/or anti-LEPR antigen-binding domains) that bind to human GP130 and/or human LEPR, and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee versions of the corresponding GP130 and/or LEPR proteins.

Therapeutic Formulation and Administration

The invention provides pharmaceutical compositions comprising anti-GP130, anti-LEPR antibodies, and LEPR× GP130 bispecific antibodies (and other antigen-binding molecules comprising anti-GP130 and/or anti-LEPR antigen-binding domains) of the present invention. The pharmaceutical compositions of the invention may be formulated with suitable carriers, excipients, and other agents that provide improved transfer, delivery, tolerance, and the like.

Therapeutic Uses of the Antibodies

The present invention includes methods comprising administering to a subject in need thereof (e.g., a mammal such as a human) a therapeutic composition comprising a LEPR×GP130 bispecific antigen-binding molecule (e.g., a LEPR×GP130 bispecific antigen-binding molecule comprising any of the D1 and D2 components as set forth in Table 20 herein). The therapeutic composition can comprise any of the LEPR×GP130 bispecific antigen-binding molecules disclosed herein, and a pharmaceutically acceptable carrier or diluent.

The LEPR×GP130 bispecific antigen-binding molecules of the invention are useful, inter alia, for the treatment, prevention and/or amelioration of any disease or disorder associated with or mediated by leptin deficiency, leptin resistance, hypoleptinemia, or otherwise treatable by stimulating or activating LEPR signaling or mimicking the natural activity of leptin in vitro or in vivo. For example, the bispecific antigen-binding molecules of the present invention are useful for treating lipodystrophy conditions. Exemplary lipodystrophy conditions that are treatable by the bispecific antigen-binding molecules of the present invention include, e.g., congenital generalized lipodystrophy, acquired generalized lipodystrophy, familial partial lipodystrophy, acquired partial lipodystrophy, centrifugal abdominal lipodystrophy, lipoatrophia annularis, localized lipodystrophy, and HIV-associated lipodystrophy.

The LEPR×GP130 bispecific antigen-binding molecules of the present invention are also useful for the treatment or prevention of one or more diseases or disorders selected from the group consisting of obesity, metabolic syndrome, diet-induced food craving, functional hypothalamic amenorrhea, type 1 diabetes, type 2 diabetes, insulin resistance, severe insulin resistance including severe insulin resistance due to mutation in insulin receptor, severe insulin resistance not caused by mutation in the insulin receptor, severe insulin resistance caused by a mutation in downstream signaling pathways or induced by other causes, non-alcoholic and alcoholic fatty liver diseases, Alzheimer's disease, leptin deficiency, leptin resistance, lipodystrophies, Leprechaunism/Donohue syndrome, Rabson-Mendenhall syndrome.

In the context of the methods of treatment described herein, the LEPR×GP130 bispecific antigen-binding molecule may be administered as a monotherapy (i.e., as the only therapeutic agent) or in combination with one or more additional therapeutic agents (examples of which are described elsewhere herein).

Combination Therapies and Formulations

The present invention includes compositions and therapeutic formulations comprising any of the LEPR×GP130 bispecific antigen-binding molecules described herein in combination with one or more additional therapeutically active components, and methods of treatment comprising administering such combinations to subjects in need thereof.

The LEPR×GP130 bispecific antigen-binding molecules of the present invention may be co-formulated with and/or administered in combination with one or more additional therapeutically active component(s), such as. e.g., pharmaceutical products prescribed for the treatment of obesity, hypercholesterolemia, hyperlipidemia, type 2 diabetes, type 1 diabetes, appetite control, infertility, etc. Examples of such additional therapeutically active components include, e.g., recombinant human leptin (e.g., metreleptin [MYALEPT]), PCSK9 inhibitors (e.g., anti-PCSK9 antibodies [alirocumab, evolocumab, bococizumab, lodelcizumab, ralpancizumab, etc.]), statins (atorvastatin, rosuvastatin, cerivastatin, pitavastatin, fluvastatin, simvastatin, lovastatin, pravastatin, etc.), ezetimibe, insulin, insulin variants, insulin secretagogues, metformin, sulfonylureas, sodium glucose cotransporter 2 (SGLT2) Inhibitors (e.g., dapaglifozin, canaglifozin, empagliflozin, etc.), GLP-1 agonists/analogues (e.g., extendin-4, exenatide, liraglutide, lixisenatide, albiglutide, dulaglutide, etc.), glucagon (GCG) inhibitors (e.g., anti-GCG antibodies), glucagon receptor (GCGR) inhibitors (e.g., anti-GCGR antibodies, small molecule GCGR antagonists, GCGR-specific antisense oligonucleotides, anti-GCGR aptamers [e.g., Spiegelmers], etc.), angiopoietin-like protein (ANGPTL) inhibitors (e.g., anti-ANGPTL3 antibodies, anti-ANGPTL4 antibodies, anti-ANGPTL8 antibodies, etc.), Phentermine, Orlistat, Topiramate, Bupropion, Topiramate/Phentermine, Bupropion/Naltrexone, Bupropion/Zonisamide, Pramlintide/Metrelepin, Lorcaserin, Cetilistat, Tesofensine, Velneperit, etc.

The additional therapeutically active component(s), e.g., any of the agents listed above or derivatives thereof, may be administered just prior to, concurrent with, or shortly after the administration of a LEPR×GP130 bispecific antigen-binding molecule of the present invention; (for purposes of the present disclosure, such administration regimens are considered the administration of a LEPR×GP130 bispecific antigen-binding molecule "in combination with" an additional therapeutically active component). The present invention includes pharmaceutical compositions in which a LEPR×GP130 bispecific antigen-binding molecule of the present invention is co-formulated with one or more of the additional therapeutically active component(s) as described elsewhere herein.

Administration Regimens

According to certain embodiments of the present invention, multiple doses of a LEPR×GP130 bispecific antigen-binding molecule (or a pharmaceutical composition comprising a combination of a LEPR×GP130 bispecific antigen-binding molecule and any of the additional therapeutically active agents mentioned herein) may be administered to a subject over a defined time course. The methods according to this aspect of the invention comprise sequentially administering to a subject multiple doses of a LEPR×GP130 bispecific antigen-binding molecule of the invention. As used herein, "sequentially administering" means that each dose of LEPR×GP130 bispecific antigen-binding molecule is administered to the subject at a different point in time, e.g., on different days separated by a predetermined interval (e.g., hours, days, weeks or months). The present invention includes methods which comprise sequentially administering to the patient a single initial dose of a LEPR×GP130 bispecific antigen-binding molecule, followed by one or more secondary doses of the LEPR×GP130 bispecific antigen-binding molecule, and optionally followed by one or more tertiary doses of the LEPR×GP130 bispecific antigen-binding molecule.

The terms "initial dose," "secondary doses," and "tertiary doses," refer to the temporal sequence of administration of the LEPR×GP130 bispecific antigen-binding molecule of the invention. Thus, the "initial dose" is the dose which is administered at the beginning of the treatment regimen (also referred to as the "baseline dose," "loading dose," "starting dose," and the like); the "secondary doses" are the doses which are administered after the initial dose; and the "tertiary doses" are the doses which are administered after the secondary doses. The initial, secondary, and tertiary doses may all contain the same amount of LEPR×GP130 bispecific antigen-binding molecule, but generally may differ from one another in terms of frequency of administration. In certain embodiments, however, the amount of LEPR×GP130 bispecific antigen-binding molecule contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

Devices

The present invention also provides a vessel (e.g., a vial or chromatography column) or injection device (e.g., syringe, pre-filled syringe or autoinjector) comprising a bispecific antigen binding molecule (e.g., pharmaceutical formulation thereof) set forth herein. The vessel or injection device may be packaged into a kit.

An injection device is a device that introduces a substance into the body of a subject (e.g., a human) via a parenteral route, e.g., intraocular, intravitreal, intramuscular, subcutaneous or intravenous. For example, an injection device may be a syringe (e.g., pre-filled with the pharmaceutical formulation, such as an auto-injector) which, for example, includes a cylinder or barrel for holding fluid to be injected (e.g., comprising the antibody or fragment or a pharmaceutical formulation thereof), a needle for piecing skin, blood vessels or other tissue for injection of the fluid; and a plunger for pushing the fluid out of the cylinder and through the needle bore and into the body of the subject.

The present invention includes methods for administering a bispecific antigen binding molecule of the present invention comprising introducing e.g., injecting, the molecule into the body of the subject, e.g., with an injection device.

Expression Methods

The present invention includes recombinant methods for making a bispecific antigen binding molecule of the present invention, or an immunoglobulin chain thereof, comprising (i) introducing, into a host cell, one or more polynucleotides encoding light and/or heavy immunoglobulin chains of such a bispecific antigen binding molecule, for example, wherein the polynucleotide is in a vector; and/or integrates into the host cell chromosome and/or is operably linked to a promoter; (ii) culturing the host cell (e.g., mammalian, fungal, Chinese hamster ovary (CHO), *Pichia* or *Pichia pastoris*) under conditions favorable to expression of the polynucleotide and, (iii) optionally, isolating the bispecific antigen binding molecule or immunoglobulin chain from the host cell and/or medium in which the host cell is grown. The product of such a method also forms part of the present invention along with a pharmaceutical composition thereof.

In an embodiment of the invention, a method for making a bispecific antigen binding molecule includes a method of purifying the molecule, e.g., by column chromatography, precipitation and/or filtration. The product of such a method also forms part of the present invention along with a pharmaceutical composition thereof.

Host cells comprising a bispecific antigen binding molecule of the present invention and/or a polynucleotide encoding immunoglobulin chains of such a molecule (e.g., in a vector) are also part of the present invention. Host cells include, for example, mammalian cells such as Chinese hamster ovary (CHO) cells and fungal cells such as *Pichia* cells (e.g., *P. pastoris*).

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Anti-GP130 Antibodies

Anti-GP130 antibodies were obtained by immunizing a genetically engineered mouse comprising DNA encoding human immunoglobulin heavy and kappa light chain variable regions with an immunogen comprising recombinant human GP130 extracellular domain. The mice used for the immunizations express a "universal light chain." That is, the antibodies produced in this mouse have different heavy chain variable regions but essentially identical light chain variable domains.

The antibody immune response was monitored by a GP130-specific immunoassay. When a desired immune response was achieved splenocytes were harvested and fused with mouse myeloma cells to preserve their viability and from hybridoma cell lines. The hybridoma cell lines were screened and selected to identify cell lines that produce GP130-specific antibodies. Using this technique several anti-GP130 chimeric antibodies (i.e., antibodies possessing human variable domains and mouse constant domains) were obtained. In addition, several fully human anti-GP130 antibodies were isolated directly from antigen-positive B cells without fusion to myeloma cells, as described in US 2007/0280945A1.

Certain biological properties of the exemplary anti-GP130 antibodies generated in accordance with the methods of this Example, and bispecific antibodies constructed therefrom, are described in detail in the Examples set forth below.

Example 2. Heavy and Light Chain Variable Region Amino Acid and Nucleic Acid Sequences of Anti-GP130

Table 1 sets forth the amino acid sequence identifiers of the heavy and light chain variable regions and CDRs of selected anti-LEPR antibodies of the invention. (As noted above, all antibodies generated in Example 1 possess the same light chain variable region and the same light chain CDR sequences as well). The corresponding nucleic acid sequence identifiers are set forth in Table 2.

TABLE 1

Anti-GP130 Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| MAb16614 | 18 | 20 | 22 | 24 | 10 | 12 | 14 | 16 |
| MAb16618 | 26 | 28 | 30 | 32 | 10 | 12 | 14 | 16 |
| MAb16622 | 34 | 36 | 38 | 40 | 10 | 12 | 14 | 16 |
| MAb16623 | 42 | 44 | 46 | 48 | 10 | 12 | 14 | 16 |
| MAb16636 | 50 | 52 | 54 | 56 | 10 | 12 | 14 | 16 |
| MAb16637 | 58 | 60 | 62 | 64 | 10 | 12 | 14 | 16 |
| MAb16656 | 66 | 68 | 70 | 72 | 10 | 12 | 14 | 16 |
| MAb16659 | 74 | 76 | 78 | 80 | 10 | 12 | 14 | 16 |
| MAb16662 | 82 | 84 | 86 | 88 | 10 | 12 | 14 | 16 |

TABLE 1-continued

Anti-GP130 Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| MAb16664 | 90 | 92 | 94 | 96 | 10 | 12 | 14 | 16 |
| MAb16665 | 98 | 100 | 102 | 104 | 10 | 12 | 14 | 16 |
| MAb16666 | 106 | 108 | 110 | 112 | 10 | 12 | 14 | 16 |
| MAb16669 | 114 | 116 | 118 | 120 | 10 | 12 | 14 | 16 |
| MAb16673 | 122 | 124 | 126 | 128 | 10 | 12 | 14 | 16 |
| MAb16676 | 130 | 132 | 134 | 136 | 10 | 12 | 14 | 16 |
| MAb16680 | 138 | 140 | 142 | 144 | 10 | 12 | 14 | 16 |
| MAb16682 | 146 | 148 | 150 | 152 | 10 | 12 | 14 | 16 |
| MAb16683 | 154 | 156 | 158 | 160 | 10 | 12 | 14 | 16 |

TABLE 2

Anti-GP130 Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| MAb16614 | 17 | 19 | 21 | 23 | 9 | 11 | 13 | 15 |
| MAb16618 | 25 | 27 | 29 | 31 | 9 | 11 | 13 | 15 |
| MAb16622 | 33 | 35 | 37 | 39 | 9 | 11 | 13 | 15 |
| MAb16623 | 41 | 43 | 45 | 47 | 9 | 11 | 13 | 15 |
| MAb16636 | 49 | 51 | 53 | 55 | 9 | 11 | 13 | 15 |
| MAb16637 | 57 | 59 | 61 | 63 | 9 | 11 | 13 | 15 |
| MAb16656 | 65 | 67 | 69 | 71 | 9 | 11 | 13 | 15 |
| MAb16659 | 73 | 75 | 77 | 79 | 9 | 11 | 13 | 15 |
| MAb16662 | 81 | 83 | 85 | 87 | 9 | 11 | 13 | 15 |
| MAb16664 | 89 | 91 | 93 | 95 | 9 | 11 | 13 | 15 |
| MAb16665 | 97 | 99 | 101 | 103 | 9 | 11 | 13 | 15 |
| MAb16666 | 105 | 107 | 109 | 111 | 9 | 11 | 13 | 15 |
| MAb16669 | 113 | 115 | 117 | 119 | 9 | 11 | 13 | 15 |
| MAb16673 | 121 | 123 | 125 | 127 | 9 | 11 | 13 | 15 |
| MAb16676 | 129 | 131 | 133 | 135 | 9 | 11 | 13 | 15 |
| MAb16680 | 137 | 139 | 141 | 143 | 9 | 11 | 13 | 15 |
| MAb16682 | 145 | 147 | 149 | 151 | 9 | 11 | 13 | 15 |
| MAb16683 | 153 | 155 | 157 | 159 | 9 | 11 | 13 | 15 |

The antibodies of the present invention can be of any isotype. For example, anti-GP130 antibodies of the invention may comprise variable domain and CDR sequences as set forth in Tables 1 and 2 and a human Fc domain of isotype IgG4, IgG1, etc. For certain applications or experiments the Fc domain may be a mouse Fc domain. As will be appreciated by a person of ordinary skill in the art, an antibody having a particular Fc isotype can be converted to an antibody with a different Fc isotype (e.g., an antibody with a mouse IgG4 Fc can be converted to an antibody with a human IgG1, etc.), but in any event, the variable domains (including the CDRs)—which are indicated by the numerical identifiers shown in Tables 1 and 2—will remain the same, and the binding properties are expected to be identical or substantially similar regardless of the nature of the Fc domain.

Example 3. Biacore Binding Kinetics of Anti-GP130 Monoclonal Antibodies Binding to Different GP130 Reagents Measured at 25° C. and 37° C.

Equilibrium dissociation constant ($K_D$) for different GP130 reagents binding to purified anti-GP130 monoclonal antibodies were determined using a real-time surface plasmon resonance based Biacore 4000 biosensor. All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore sensor surface was first derivatized by amine coupling with a monoclonal mouse anti-human Fc antibody (GE, #BR-1008-39) to capture anti-GP130 monoclonal antibodies. Binding studies were performed on the following monomeric and dimeric GP130 reagents: human GP130 extracellular domain expressed with a C-terminal myc-myc-hexahistidine tag (hGP130-mmH; SEQ ID NO:191), *Macaca fascicularis* GP130 extracellular domain expressed with a C-terminal myc-myc-hexahistidine tag (mfGP130-mmH; SEQ ID NO:194), human GP130 extracellular domain expressed with a C-terminal mouse IgG2a Fc tag (hGP130-hFc; SEQ ID NO:197), mouse GP130 extracellular domain expressed with a C-terminal myc-myc-hexahistidine tag (mGP130-mmH; SEQ ID NO:196) and rat GP130 extracellular domain expressed with a C-terminal myc-myc-hexahistidine tag (rGP130-mmH; SEQ ID NO:195). Reagents tagged with "mmH" are monomeric, whereas reagents tagged with "mFc" are dimeric. Thus, for example, "hGP130-mmH" is also referred to as "monomeric human GP130," and "hGP130-mFc" is also referred to as "dimeric human GP130."

Different concentrations of hGP130-mmH, mfGP130-mmH, hGP130-mFc (100 nM-3.7 nM; 3-fold serial dilution) or 100 nM of mGP130-mmH and rGP130-mmH were first prepared in HBS-ET running buffer and were injected over anti-human Fc captured anti-GP130 monoclonal antibody surface for 4 minutes at a flow rate of 304/minute, while the dissociation of monoclonal antibody bound GP130 reagent was monitored for 10 minutes in HBS-ET running buffer. The association rate ($k_a$) and dissociation rate ($k_d$) were determined by fitting the real-time binding sensorgrams to a 1:1 binding model with mass transport limitation using Scrubber 2.0c curve-fitting software. Binding dissociation equilibrium constant ($K_D$) and dissociative half-life ($t_{1/2}$) were calculated from the kinetic rates as:

$$K_D(M) = \frac{kd}{ka}, \text{ and } t\frac{1}{2}(\min) = \frac{\ln(2)}{60 * kd}$$

Binding kinetics parameters for hGP130-MMH, mfGP130-MMH, hGP130.mFc, mGP130-MMH or rGP130-MMH binding to different anti-GP130 monoclonal antibodies of the invention at 25° C. and 37° C. are shown in Tables 3 through 12.

TABLE 3

Binding kinetics parameters of hGP130-MMH binding to GP130 monoclonal antibodies at 25° C.

| mAb Captured | mAb Capture Level (RU) | 100 nM Ag Bound (RU) | ka (1/Ms) | kd (1/s) | KD (M) | t½ (min) |
|---|---|---|---|---|---|---|
| MAb16614 | 143 ± 0.67 | 18 | 5.52E+04 | 1.01E−02 | 1.83E−07 | 1.1 |
| MAb16618 | 182 ± 0.52 | 52 | 3.54E+05 | 4.25E−02 | 1.20E−07 | 0.3 |
| MAb16622 | 197 ± 0.95 | 36 | 1.20E+05 | 2.43E−02 | 2.03E−07 | 0.5 |
| MAb16623 | 243 ± 1.48 | 77 | 1.80E+05 | 3.77E−03 | 2.10E−08 | 3 |
| MAb16636 | 195 ± 0.45 | 37 | 2.70E+04 | 9.93E−04 | 3.68E−08 | 12 |
| MAb16637 | 306 ± 1.71 | 91 | 7.11E+04 | 1.10E−03 | 1.55E−08 | 10 |
| MAb16641 | 154 ± 0.93 | 111 | 3.56E+05 | 8.87E−04 | 2.49E−09 | 13 |
| MAb16646 | 167 ± 0.45 | 58 | 5.88E+04 | 7.73E−04 | 1.31E−08 | 15 |
| MAb16656 | 189 ± 0.44 | 44 | 3.59E+04 | 8.25E−04 | 2.30E−08 | 14 |
| MAb16659 | 212 ± 0.39 | 77 | 6.93E+05 | 4.59E−04 | 6.63E−10 | 25 |
| MAb16662 | 215 ± 0.67 | 22 | 2.35E+05 | 2.90E−02 | 1.23E−07 | 0.4 |
| MAb16664 | 217 ± 0.69 | 14 | 6.98E+05 | 1.64E−03 | 2.35E−09 | 7 |
| MAb16665 | 294 ± 1.48 | 20 | 1.15E+05 | 4.73E−02 | 4.11E−07 | 0.2 |
| MAb16666 | 317 ± 2.83 | 138 | 3.17E+05 | 4.56E−03 | 1.44E−08 | 3 |
| MAb16669 | 152 ± 0.5 | 17 | 1.14E+04 | 4.03E−04 | 3.54E−08 | 29 |
| MAb16673 | 158 ± 0.32 | 58 | 2.15E+05 | 1.41E−02 | 6.55E−08 | 0.8 |
| MAb16676 | 176 ± 0.33 | 51 | 2.87E+05 | 6.31E−04 | 2.19E−09 | 18 |
| MAb16680 | 270 ± 0.91 | 57 | 1.47E+05 | 4.75E−04 | 3.24E−09 | 24 |
| MAb16682 | 186 ± 0.55 | 21 | 1.21E+05 | 1.64E−02 | 1.36E−07 | 0.7 |
| MAb16683 | 238 ± 2.72 | 54 | 6.97E+04 | 3.25E−03 | 4.67E−08 | 4 |
| MAb16684 | 204 ± 1.09 | 40 | 5.32E+04 | 6.22E−03 | 1.17E−07 | 1.9 |
| MAb16687 | 172 ± 0.55 | 111 | 2.04E+05 | 4.86E−04 | 2.38E−09 | 24 |
| MAb16692 | 182 ± 1.08 | 121 | 2.40E+05 | 6.98E−04 | 2.91E−09 | 17 |
| MAb16693 | 159 ± 0.52 | 29 | 1.50E+05 | 1.51E−02 | 1.00E−07 | 0.8 |
| MAb16695 | 186 ± 0.79 | 122 | 2.80E+05 | 1.05E−03 | 3.77E−09 | 11 |
| MAb16702 | 208 ± 0.78 | 75 | 1.39E+05 | 3.74E−04 | 2.69E−09 | 31 |
| IgG4 Isotype Control | 229 ± 1.42 | 2 | NB | NB | NB | NB |

NB indicates that no binding was observed under the current experimental conditions.

TABLE 4

Binding kinetics parameters of hGP130-MMH binding to GP130 monoclonal antibodies at 37° C.

| mAb Captured | mAb Capture Level (RU) | 100 nM Ag Bound (RU) | ka (1/Ms) | kd (1/s) | KD (M) | t½ (min) |
|---|---|---|---|---|---|---|
| MAb16614 | 176 ± 2.98 | 10 | 2.47E+05 | 3.00E−02 | 1.21E−07 | 0.4 |
| MAb16618 | 219 ± 2.04 | 36 | 1.08E+06 | 1.12E−01 | 1.03E−07 | 0.1 |
| MAb16622 | 238 ± 3.05 | 30 | 2.55E+05 | 5.74E−02 | 2.25E−07 | 0.2 |
| MAb16623 | 285 ± 3.24 | 68 | 3.81E+05 | 1.23E−02 | 3.22E−08 | 0.9 |
| MAb16636 | 231 ± 2.35 | 50 | 6.16E+04 | 4.41E−03 | 7.16E−08 | 2.6 |
| MAb16637 | 352 ± 2.31 | 110 | 1.97E+05 | 3.42E−03 | 1.73E−08 | 3 |
| MAb16641 | 188 ± 3.13 | 107 | 7.65E+05 | 2.49E−03 | 3.25E−09 | 5 |
| MAb16646 | 212 ± 2.83 | 66 | 9.81E+04 | 3.31E−03 | 3.38E−08 | 3.5 |
| MAb16656 | 214 ± 1.6 | 50 | 7.01E+04 | 4.26E−03 | 6.07E−08 | 2.7 |
| MAb16659 | 239 ± 1.56 | 82 | 9.28E+05 | 1.71E−03 | 1.84E−09 | 7 |
| MAb16662 | 245 ± 0.93 | 17 | 4.36E+05 | 5.85E−02 | 1.34E−07 | 0.2 |
| MAb16664 | 251 ± 2.08 | 16 | 5.80E+05 | 8.26E−03 | 1.42E−08 | 1.4 |
| MAb16665 | 336 ± 2.56 | 19 | 4.23E+05 | 6.93E−02 | 1.64E−07 | 0.2 |
| MAb16666 | 350 ± 4.52 | 104 | 5.88E+05 | 1.01E−02 | 1.71E−08 | 1.1 |
| MAb16669 | 173 ± 1.38 | 25 | 5.51E+04 | 1.06E−03 | 1.93E−08 | 11 |

TABLE 4-continued

Binding kinetics parameters of hGP130-MMH binding to GP130 monoclonal antibodies at 37° C.

| mAb Captured | mAb Capture Level (RU) | 100 nM Ag Bound (RU) | ka (1/Ms) | kd (1/s) | KD (M) | t½ (min) |
|---|---|---|---|---|---|---|
| MAb16673 | 180 ± 1.31 | 40 | 5.36E+05 | 4.04E-02 | 7.54E-08 | 0.3 |
| MAb16676 | 192 ± 1.72 | 52 | 3.93E+05 | 2.36E-03 | 6.01E-09 | 5 |
| MAb16680 | 291 ± 1.59 | 58 | 9.48E+04 | 2.06E-03 | 2.17E-08 | 6 |
| MAb16682 | 211 ± 2.32 | 16 | 3.01E+05 | 3.41E-02 | 1.13E-07 | 0.3 |
| MAb16683 | 262 ± 1.88 | 38 | 1.07E+05 | 1.25E-02 | 1.17E-07 | 0.9 |
| MAb16684 | 220 ± 1.73 | 18 | 1.63E+05 | 3.60E-02 | 2.21E-07 | 0.3 |
| MAb16687 | 184 ± 1.85 | 107 | 3.22E+05 | 1.82E-03 | 5.66E-09 | 6 |
| MAb16692 | 197 ± 1.78 | 107 | 7.24E+05 | 3.05E-03 | 4.21E-09 | 4 |
| MAb16693 | 180 ± 1.26 | 22 | 3.82E+05 | 4.02E-02 | 1.05E-07 | 0.3 |
| MAb16695 | 192 ± 1.56 | 87 | 4.94E+05 | 6.27E-03 | 1.27E-08 | 1.8 |
| MAb16702 | 216 ± 0.72 | 68 | 2.35E+05 | 1.66E-03 | 7.05E-09 | 7 |
| IgG4 Isotype Control | 258 ± 1.09 | 2 | NB | NB | NB | NB |

NB indicates that no binding was observed under the current experimental conditions.

At 25° C., anti-GP130 monoclonal antibodies bound to hGP130-MMH with $K_D$ values ranging from 663 pM to 411 nM, as shown in Table 3. At 37° C., anti-GP130 monoclonal antibodies bound to hGP130-MMH with $K_D$ values ranging from 1.84 nM to 225 nM, as shown in Table 4.

TABLE 5

Binding kinetics parameters of mfGP130-MMH binding to GP130 monoclonal antibodies at 25° C.

| mAb Captured | mAb Capture Level (RU) | 100 nM Ag Bound (RU) | ka (1/Ms) | kd (1/s) | KD (M) | t½ (min) |
|---|---|---|---|---|---|---|
| MAb16614 | 142 ± 0.65 | 16 | 7.44E+04 | 1.04E-02 | 1.39E-07 | 1.1 |
| MAb16618 | 181 ± 0.48 | 40 | 3.74E+05 | 6.21E-02 | 1.66E-07 | 0.2 |
| MAb16622 | 195 ± 0.74 | 34 | 1.32E+05 | 2.00E-02 | 1.51E-07 | 0.6 |
| MAb16623 | 240 ± 0.79 | 74 | 1.87E+05 | 4.76E-03 | 2.55E-08 | 2.4 |
| MAb16636 | 193 ± 0.49 | 23 | 2.01E+04 | 2.16E-03 | 1.07E-07 | 5 |
| MAb16637 | 304 ± 3.59 | 87 | 6.83E+04 | 1.09E-03 | 1.59E-08 | 11 |
| MAb16641 | 153 ± 3.55 | 109 | 3.44E+05 | 8.60E-04 | 2.50E-09 | 13 |
| MAb16646 | 166 ± 0.29 | 52 | 4.79E+04 | 7.72E-04 | 1.61E-08 | 15 |
| MAb16656 | 187 ± 0.26 | 42 | 4.44E+04 | 8.46E-04 | 1.90E-08 | 14 |
| MAb16659 | 211 ± 0.43 | 74 | 5.42E+05 | 4.40E-04 | 8.12E-10 | 26 |
| MAb16662 | 214 ± 1.92 | 15 | 2.07E+05 | 3.80E-02 | 1.84E-07 | 0.3 |
| MAb16664 | 216 ± 1.31 | 13 | 5.43E+05 | 1.75E-03 | 3.21E-09 | 7 |
| MAb16665 | 294 ± 1.19 | 16 | 2.17E+05 | 5.05E-02 | 2.33E-07 | 0.2 |
| MAb16666 | 317 ± 2.67 | 123 | 2.90E+05 | 5.30E-03 | 1.83E-08 | 2.2 |
| MAb16669 | 151 ± 0.6 | 3 | NB | NB | NB | NB |
| MAb16673 | 157 ± 0.25 | 86 | 3.12E+05 | 6.93E-03 | 2.22E-08 | 1.7 |
| MAb16676 | 175 ± 0.54 | 49 | 2.72E+05 | 5.97E-04 | 2.20E-09 | 19 |
| MAb16680 | 267 ± 0.84 | 52 | 1.20E+05 | 4.89E-04 | 4.07E-09 | 24 |
| MAb16682 | 184 ± 0.48 | 20 | 1.28E+05 | 1.68E-02 | 1.32E-07 | 0.7 |
| MAb16683 | 236 ± 1.97 | 59 | 6.57E+04 | 2.46E-03 | 3.74E-08 | 5 |
| MAb16684 | 203 ± 0.61 | 4 | IC | IC | IC | IC |
| MAb16687 | 170 ± 0.58 | 108 | 1.84E+05 | 5.24E-04 | 2.85E-09 | 22 |
| MAb16692 | 179 ± 0.96 | 109 | 2.09E+05 | 7.45E-04 | 3.56E-09 | 16 |
| MAb16693 | 159 ± 0.33 | 6 | NB | NB | NB | NB |
| MAb16695 | 184 ± 0.5 | 120 | 2.67E+05 | 9.98E-04 | 3.74E-09 | 12 |
| MAb16702 | 205 ± 0.74 | 48 | 5.63E+04 | 5.95E-04 | 1.06E-08 | 19 |
| IgG4 Isotype Control | 227 ± 2.09 | 2 | NB | NB | NB | NB |

NB indicates that no binding was observed under the current experimental conditions.

IC indicates that observed binding was inclusive and was unable to fit the real time binding data under the current experimental conditions.

TABLE 6

Binding kinetics parameters of mfGP130-MMH binding to GP130 monoclonal antibodies at 37° C.

| mAb Captured | mAb Capture Level (RU) | 100 nM Ag Bound (RU) | ka (1/Ms) | kd (1/s) | KD (M) | t½ (min) |
|---|---|---|---|---|---|---|
| MAb16614 | 168 ± 1.52 | 8 | 3.70E+05 | 2.67E-02 | 7.22E-08 | 0.4 |
| MAb16618 | 210 ± 1.02 | 26 | 1.33E+06 | 1.20E-01 | 9.03E-08 | 0.1 |
| MAb16622 | 229 ± 2 | 28 | 2.72E+05 | 5.37E-02 | 1.98E-07 | 0.2 |
| MAb16623 | 274 ± 1.25 | 60 | 3.52E+05 | 1.56E-02 | 4.43E-08 | 0.7 |
| MAb16636 | 222 ± 1.09 | 25 | 3.95E+04 | 9.45E-03 | 2.39E-07 | 1.2 |
| MAb16637 | 342 ± 1.61 | 104 | 1.78E+05 | 2.63E-03 | 1.48E-08 | 4 |
| MAb16641 | 179 ± 1.7 | 98 | 6.94E+05 | 2.42E-03 | 3.48E-09 | 5 |
| MAb16646 | 202 ± 1.18 | 58 | 8.64E+04 | 3.37E-03 | 3.91E-08 | 3.4 |
| MAb16656 | 208 ± 1.42 | 47 | 6.70E+04 | 4.11E-03 | 6.13E-08 | 2.8 |
| MAb16659 | 232 ± 1.18 | 78 | 7.47E+05 | 1.74E-03 | 2.34E-09 | 7 |
| MAb16662 | 238 ± 0.85 | 14 | 3.55E+05 | 5.92E-02 | 1.67E-07 | 0.2 |
| MAb16664 | 243 ± 1.68 | 16 | 6.80E+05 | 7.88E-03 | 1.16E-08 | 1.5 |
| MAb16665 | 330 ± 0.88 | 14 | 4.92E+05 | 1.01E-01 | 2.05E-07 | 0.1 |
| MAb16666 | 340 ± 3.16 | 90 | 5.28E+05 | 1.31E-02 | 2.47E-08 | 0.9 |
| MAb16669 | 167 ± 0.83 | 8 | NB | NB | NB | NB |
| MAb16673 | 175 ± 1.1 | 64 | 6.17E+05 | 2.11E-02 | 3.41E-08 | 0.5 |
| MAb16676 | 187 ± 1.43 | 48 | 3.41E+05 | 2.43E-03 | 7.12E-09 | 5 |
| MAb16680 | 284 ± 1.39 | 51 | 9.07E+04 | 2.17E-03 | 2.39E-08 | 5 |
| MAb16682 | 205 ± 0.85 | 15 | 3.11E+05 | 3.86E-02 | 1.24E-07 | 0.3 |
| MAb16683 | 256 ± 1.73 | 43 | 9.65E+04 | 1.21E-02 | 1.25E-07 | 1.0 |
| MAb16684 | 214 ± 1.12 | 2 | NB | NB | NB | NB |
| MAb16687 | 179 ± 1.38 | 101 | 2.84E+05 | 1.97E-03 | 6.93E-09 | 6 |
| MAb16692 | 191 ± 1.17 | 97 | 6.39E+05 | 2.97E-03 | 4.65E-09 | 4 |
| MAb16693 | 175 ± 0.86 | 8 | NB | NB | NB | NB |
| MAb16695 | 186 ± 1.27 | 84 | 4.33E+05 | 5.92E-03 | 1.37E-08 | 2.0 |
| MAb16702 | 211 ± 0.9 | 46 | 8.66E+04 | 2.19E-03 | 2.52E-08 | 5 |
| IgG4 Isotype Control | 253 ± 1.16 | 3 | NB | NB | NB | NB |

NB indicates that no binding was observed under the current experimental conditions.

23 out of 26 anti-GP130 monoclonal antibodies of the invention bound to mfGP130-MMH. At 25° C., anti-GP130 monoclonal antibodies bound to mfGP130-MMH with $K_D$ values ranging from 812 pM to 233 nM, as shown in Table 5. At 37° C., anti-GP130 monoclonal antibodies bound to mfGP130-MMH with $K_D$ values ranging from 2.34 nM to 239 nM, as shown in Table 6.

TABLE 7

Binding kinetics parameters of hGP130-mFc binding to GP130 monoclonal antibodies at 25° C.

| mAb Captured | mAb Capture Level (RU) | 100 nM Ag Bound (RU) | ka (1/Ms) | kd (1/s) | KD (M) | t½ (min) |
|---|---|---|---|---|---|---|
| MAb16614 | 143 ± 0.19 | 83 | 8.57E+04 | 3.83E-04 | 4.47E-09 | 30 |
| MAb16618 | 181 ± 0.44 | 202 | 1.19E+06 | 2.79E-04 | 2.36E-10 | 41 |
| MAb16622 | 196 ± 0.81 | 164 | 4.97E+05 | 3.06E-04 | 6.15E-10 | 38 |
| MAb16623 | 242 ± 1.53 | 184 | 4.44E+05 | 2.08E-04 | 4.68E-10 | 56 |
| MAb16636 | 194 ± 0.62 | 91 | 5.88E+04 | 1.13E-04 | 1.92E-09 | 102 |
| MAb16637 | 306 ± 1.48 | 189 | 2.32E+05 | 1.50E-04 | 6.47E-10 | 77 |
| MAb16641 | 153 ± 1.08 | 142 | 7.70E+05 | 2.97E-04 | 3.86E-10 | 39 |
| MAb16646 | 167 ± 0.41 | 77 | 7.19E+04 | 2.25E-04 | 3.13E-09 | 51 |
| MAb16656 | 188 ± 0.42 | 98 | 7.81E+04 | 1.32E-04 | 1.68E-09 | 88 |
| MAb16659 | 212 ± 0.34 | 186 | 1.72E+06 | 6.28E-05 | 3.66E-11 | 184 |
| MAb16662 | 215 ± 1.08 | 90 | 6.20E+05 | 4.79E-04 | 7.72E-10 | 24 |
| MAb16664 | 217 ± 0.62 | 26 | 3.05E+06 | 3.54E-04 | 1.16E-10 | 33 |
| MAb16665 | 293 ± 1.36 | 158 | 3.99E+05 | 1.09E-03 | 2.72E-09 | 11 |
| MAb16666 | 317 ± 2.14 | 253 | 1.14E+06 | 1.37E-04 | 1.20E-10 | 85 |
| MAb16669 | 152 ± 0.46 | 40 | 2.93E+04 | 2.41E-04 | 8.21E-09 | 48 |
| MAb16673 | 158 ± 0.38 | 169 | 5.60E+05 | 9.66E-05 | 1.73E-10 | 120 |

TABLE 7-continued

Binding kinetics parameters of hGP130-mFc binding to GP130 monoclonal antibodies at 25° C.

| mAb Captured | mAb Capture Level (RU) | 100 nM Ag Bound (RU) | ka (1/Ms) | kd (1/s) | KD (M) | t½ (min) |
|---|---|---|---|---|---|---|
| MAb16676 | 176 ± 0.22 | 119 | 8.53E+05 | 7.13E−05 | 8.36E−11 | 162 |
| MAb16680 | 269 ± 0.69 | 79 | 1.72E+05 | 2.31E−04 | 1.34E−09 | 50 |
| MAb16682 | 186 ± 0.74 | 126 | 1.72E+05 | 3.61E−04 | 2.10E−09 | 32 |
| MAb16683 | 236 ± 0.73 | 107 | 1.67E+05 | 3.11E−04 | 1.86E−09 | 37 |
| MAb16684 | 204 ± 0.27 | 96 | 1.28E+05 | 4.59E−04 | 3.60E−09 | 25 |
| MAb16687 | 171 ± 0.64 | 178 | 4.44E+05 | 4.21E−05 | 9.50E−11 | 274 |
| MAb16692 | 180 ± 0.69 | 174 | 6.13E+05 | 1.18E−04 | 1.93E−10 | 98 |
| MAb16693 | 159 ± 0.41 | 123 | 2.09E+05 | 2.51E−04 | 1.20E−09 | 46 |
| MAb16695 | 185 ± 0.29 | 189 | 6.83E+05 | 2.06E−04 | 3.01E−10 | 56 |
| MAb16702 | 206 ± 1.11 | 159 | 6.22E+05 | 2.52E−04 | 4.05E−10 | 46 |
| IgG4 Isotype Control | 228 ± 1.43 | 5 | NB | NB | NB | NB |

NB indicates that no binding was observed under the current experimental conditions

TABLE 8

Binding kinetics parameters of hGP130-mFc binding to GP130 monoclonal antibodies at 37° C.

| mAb Captured | mAb Capture Level (RU) | 100 nM Ag Bound (RU) | ka (1/Ms) | kd (1/s) | KD (M) | t½ (min) |
|---|---|---|---|---|---|---|
| MAb16614 | 172 ± 1.78 | 85 | 1.80E+05 | 1.72E−03 | 9.56E−09 | 7 |
| MAb16618 | 214 ± 1.83 | 236 | 1.39E+06 | 9.34E−04 | 6.74E−10 | 12 |
| MAb16622 | 232 ± 1.75 | 201 | 6.39E+05 | 8.25E−04 | 1.29E−09 | 14 |
| MAb16623 | 280 ± 2 | 224 | 5.80E+05 | 3.25E−04 | 5.60E−10 | 36 |
| MAb16636 | 225 ± 2.06 | 136 | 1.39E+05 | 1.67E−04 | 1.20E−09 | 69 |
| MAb16637 | 349 ± 2.73 | 246 | 4.96E+05 | 3.23E−04 | 6.50E−10 | 36 |
| MAb16641 | 184 ± 1.98 | 151 | 1.60E+06 | 8.28E−04 | 5.18E−10 | 14 |
| MAb16646 | 207 ± 1.7 | 99 | 1.59E+05 | 6.56E−04 | 4.14E−09 | 18 |
| MAb16656 | 212 ± 0.97 | 123 | 1.75E+05 | 2.97E−04 | 1.70E−09 | 39 |
| MAb16659 | 235 ± 1.2 | 227 | 1.91E+06 | 4.76E−05 | 2.49E−11 | 243 |
| MAb16662 | 240 ± 1.17 | 114 | 6.39E+05 | 2.65E−03 | 4.15E−09 | 4 |
| MAb16664 | 248 ± 1.36 | 37 | 1.33E+06 | 1.09E−04 | 8.15E−11 | 106 |
| MAb16665 | 334 ± 3.31 | 172 | 6.53E+05 | 2.56E−03 | 3.92E−09 | 5 |
| MAb16666 | 347 ± 3.54 | 285 | 1.21E+06 | 3.60E−04 | 2.98E−10 | 32 |
| MAb16669 | 170 ± 1.24 | 59 | 6.51E+04 | 3.80E−04 | 5.85E−09 | 30 |
| MAb16673 | 178 ± 1.09 | 199 | 6.84E+05 | 3.13E−04 | 4.57E−10 | 37 |
| MAb16676 | 190 ± 0.61 | 140 | 1.67E+06 | 9.45E−05 | 5.66E−11 | 122 |
| MAb16680 | 288 ± 0.8 | 81 | 2.43E+05 | 4.89E−04 | 2.01E−09 | 24 |
| MAb16682 | 207 ± 1.28 | 130 | 2.36E+05 | 1.96E−03 | 8.33E−09 | 6 |
| MAb16683 | 260 ± 1.27 | 111 | 1.96E+05 | 1.14E−03 | 5.80E−09 | 10 |
| MAb16684 | 217 ± 0.75 | 103 | 2.02E+05 | 9.96E−04 | 4.94E−09 | 12 |
| MAb16687 | 183 ± 1.22 | 193 | 5.89E+05 | 1.00E−05[#] | 1.70E−11 | 1155[#] |
| MAb16692 | 195 ± 0.86 | 196 | 1.30E+06 | 3.29E−04 | 2.52E−10 | 35 |
| MAb16693 | 178 ± 1.04 | 140 | 4.35E+05 | 1.25E−03 | 2.88E−09 | 9 |
| MAb16695 | 189 ± 0.93 | 183 | 1.32E+06 | 7.63E−04 | 5.80E−10 | 15 |
| MAb16702 | 214 ± 0.89 | 139 | 1.29E+06 | 7.35E−04 | 5.70E−10 | 16 |
| IgG4 Isotype Control | 256 ± 0.83 | 6 | NB | NB | NB | NB |

NB indicates that no binding was observed under the current experimental conditions.

[#]means no dissociation of hGP130-mFc from captured GP130 monoclonal antibody was observed and the $k_d$ value was manually fixed at 1.00E−05 during the analysis.

At 25° C., anti-GP130 monoclonal antibodies bound to hGP130-mFc with $K_D$ values ranging from 36.6 pM to 8.21 nM, as shown in Table 7. At 37° C., anti-GP130 monoclonal antibodies bound to hGP130-mFc with $K_D$ values ranging from 17 pM to 9.56 nM, as shown in Table 8.

TABLE 9

Binding kinetics parameters of mGP130-MMH binding to GP130 monoclonal antibodies at 25° C.

| mAb Captured | mAb Capture Level (RU) | 100 nM Ag Bound (RU) | ka (1/Ms) | kd (1/s) | KD (M) | t½ (min) |
|---|---|---|---|---|---|---|
| MAb16614 | 142 | 1 | NB | NB | NB | NB |
| MAb16618 | 181 | 1 | NB | NB | NB | NB |
| MAb16622 | 195 | 1 | NB | NB | NB | NB |
| MAb16623 | 240 | 0 | NB | NB | NB | NB |
| MAb16636 | 194 | 0 | NB | NB | NB | NB |
| MAb16637 | 304 | 1 | NB | NB | NB | NB |
| MAb16641 | 152 | −1 | NB | NB | NB | NB |
| MAb16646 | 167 | −1 | NB | NB | NB | NB |
| MAb16656 | 187 | 0 | NB | NB | NB | NB |
| MAb16659 | 210 | 1 | NB | NB | NB | NB |
| MAb16662 | 213 | −1 | NB | NB | NB | NB |
| MAb16664 | 216 | 0 | NB | NB | NB | NB |
| MAb16665 | 295 | 0 | NB | NB | NB | NB |
| MAb16666 | 315 | 1 | NB | NB | NB | NB |
| MAb16669 | 151 | 0 | NB | NB | NB | NB |
| MAb16673 | 157 | 0 | NB | NB | NB | NB |
| MAb16676 | 175 | 0 | NB | NB | NB | NB |
| MAb16680 | 267 | 0 | NB | NB | NB | NB |
| MAb16682 | 184 | 1 | NB | NB | NB | NB |
| MAb16683 | 235 | 0 | NB | NB | NB | NB |
| MAb16684 | 202 | 0 | NB | NB | NB | NB |
| MAb16687 | 170 | 1 | NB | NB | NB | NB |
| MAb16692 | 179 | −1 | NB | NB | NB | NB |
| MAb16693 | 158 | −1 | NB | NB | NB | NB |
| MAb16695 | 183 | 0 | NB | NB | NB | NB |
| MAb16702 | 206 | 0 | NB | NB | NB | NB |
| IgG4 Isotype Control | 225 | 0 | NB | NB | NB | NB |

NB indicates that no binding was observed under the current experimental conditions.

TABLE 10

Binding kinetics parameters of mGP130-MMH binding to GP130 monoclonal antibodies at 37° C.

| mAb Captured | mAb Capture Level (RU) | 100 nM Ag Bound (RU) | ka (1/Ms) | kd (1/s) | KD (M) | t½ (min) |
|---|---|---|---|---|---|---|
| MAb16614 | 167 | 0 | NB | NB | NB | NB |
| MAb16618 | 209 | 0 | NB | NB | NB | NB |
| MAb16622 | 227 | 1 | NB | NB | NB | NB |
| MAb16623 | 272 | 0 | NB | NB | NB | NB |
| MAb16636 | 220 | 0 | NB | NB | NB | NB |
| MAb16637 | 343 | −1 | NB | NB | NB | NB |
| MAb16641 | 178 | 0 | NB | NB | NB | NB |
| MAb16646 | 200 | 1 | NB | NB | NB | NB |
| MAb16656 | 208 | 0 | NB | NB | NB | NB |
| MAb16659 | 230 | 1 | NB | NB | NB | NB |
| MAb16662 | 235 | 1 | NB | NB | NB | NB |
| MAb16664 | 246 | 1 | NB | NB | NB | NB |
| MAb16665 | 330 | −1 | NB | NB | NB | NB |
| MAb16666 | 346 | 0 | NB | NB | NB | NB |
| MAb16669 | 166 | −1 | NB | NB | NB | NB |
| MAb16673 | 173 | 1 | NB | NB | NB | NB |
| MAb16676 | 187 | 0 | NB | NB | NB | NB |
| MAb16680 | 283 | 0 | NB | NB | NB | NB |
| MAb16682 | 204 | 0 | NB | NB | NB | NB |
| MAb16683 | 255 | 0 | NB | NB | NB | NB |
| MAb16684 | 214 | −1 | NB | NB | NB | NB |
| MAb16687 | 179 | 1 | NB | NB | NB | NB |
| MAb16692 | 191 | 0 | NB | NB | NB | NB |
| MAb16693 | 174 | 0 | NB | NB | NB | NB |
| MAb16695 | 185 | −1 | NB | NB | NB | NB |
| MAb16702 | 211 | 0 | NB | NB | NB | NB |
| IgG4 Isotype Control | 253 | 0 | NB | NB | NB | NB |

NB indicates that no binding was observed under the current experimental conditions.

None of the anti-GP130 monoclonal antibodies of the invention bound to mGP130-MMH at 25° C. or at 37° C. as shown in Tables 9 and 10.

TABLE 11

Binding kinetics parameters of rGP130-MMH binding to GP130 monoclonal antibodies at 25° C.

| mAb Captured | mAb Capture Level (RU) | 100 nM Ag Bound (RU) | ka (1/Ms) | kd (1/s) | KD (M) | t½ (min) |
|---|---|---|---|---|---|---|
| MAb16614 | 142 ± 0.12 | 0 | NB | NB | NB | NB |
| MAb16618 | 180 ± 0.54 | 6 | NB | NB | NB | NB |
| MAb16622 | 196 ± 0.63 | 0 | NB | NB | NB | NB |
| MAb16623 | 240 ± 0.25 | 0 | NB | NB | NB | NB |
| MAb16636 | 194 ± 0.4 | 1 | NB | NB | NB | NB |
| MAb16637 | 306 ± 2.86 | 0 | NB | NB | NB | NB |
| MAb16641 | 153 ± 0.22 | −2 | NB | NB | NB | NB |
| MAb16646 | 166 ± 0.18 | 17 | 3.84E+04 | 1.32E−02 | 3.44E−07 | 0.9 |
| MAb16656 | 188 ± 1.11 | −1 | NB | NB | NB | NB |
| MAb16659 | 210 ± 0.3 | 2 | NB | NB | NB | NB |
| MAb16662 | 213 ± 0.1 | −1 | NB | NB | NB | NB |
| MAb16664 | 215 ± 0.95 | 0 | NB | NB | NB | NB |
| MAb16665 | 291 ± 0.16 | 0 | NB | NB | NB | NB |
| MAb16666 | 316 ± 1.11 | 1 | NB | NB | NB | NB |
| MAb16669 | 151 ± 0.14 | −2 | NB | NB | NB | NB |
| MAb16673 | 157 ± 0.13 | 0 | NB | NB | NB | NB |
| MAb16676 | 174 ± 0.16 | 0 | NB | NB | NB | NB |
| MAb16680 | 267 ± 1 | 2 | NB | NB | NB | NB |
| MAb16682 | 184 ± 0.2 | 0 | NB | NB | NB | NB |
| MAb16683 | 233 ± 0.76 | 0 | NB | NB | NB | NB |
| MAb16684 | 202 ± 0.47 | 1 | NB | NB | NB | NB |
| MAb16687 | 170 ± 0.18 | 0 | NB | NB | NB | NB |

TABLE 11-continued

Binding kinetics parameters of rGP130-MMH binding to GP130 monoclonal antibodies at 25° C.

| mAb Captured | mAb Capture Level (RU) | 100 nM Ag Bound (RU) | ka (1/Ms) | kd (1/s) | KD (M) | t½ (min) |
|---|---|---|---|---|---|---|
| MAb16692 | 180 ± 0.67 | 8 | 1.78E+05 | 8.19E−02 | 4.60E−07 | 0.14 |
| MAb16693 | 158 ± 0.01 | −1 | NB | NB | NB | NB |
| MAb16695 | 183 ± 0.21 | 0 | NB | NB | NB | NB |
| MAb16702 | 206 ± 0.36 | 1 | NB | NB | NB | NB |
| IgG4 Isotype Control | 226 ± 0.27 | 0 | NB | NB | NB | NB |

NB indicates that no binding was observed under the current experimental conditions.

TABLE 12

Binding kinetics parameters of rGP130-MMH binding to GP130 monoclonal antibodies at 37° C.

| mAb Captured | mAb Capture Level (RU) | 100 nM Ag Bound (RU) | ka (1/Ms) | kd (1/s) | KD (M) | t½ (min) |
|---|---|---|---|---|---|---|
| MAb16614 | 167 ± 0.23 | 0 | NB | NB | NB | NB |
| MAb16618 | 207 ± 0.91 | 2 | NB | NB | NB | NB |
| MAb16622 | 227 ± 0.51 | 1 | NB | NB | NB | NB |
| MAb16623 | 270 ± 0.14 | 0 | NB | NB | NB | NB |
| MAb16636 | 219 ± 0.61 | 0 | NB | NB | NB | NB |
| MAb16637 | 337 ± 1.83 | 0 | NB | NB | NB | NB |
| MAb16641 | 177 ± 0.86 | −1 | NB | NB | NB | NB |
| MAb16646 | 199 ± 0.44 | 7 | 1.77E+05 | 7.12E−02 | 4.03E−07 | 0.16 |
| MAb16656 | 207 ± 0.08 | 0 | NB | NB | NB | NB |
| MAb16659 | 229 ± 0.21 | 1 | NB | NB | NB | NB |
| MAb16662 | 235 ± 0.57 | 1 | NB | NB | NB | NB |
| MAb16664 | 243 ± 0.44 | 0 | NB | NB | NB | NB |
| MAb16665 | 328 ± 1.24 | −1 | NB | NB | NB | NB |
| MAb16666 | 341 ± 2.48 | 1 | NB | NB | NB | NB |
| MAb16669 | 166 ± 0.15 | −2 | NB | NB | NB | NB |
| MAb16673 | 172 ± 0.18 | 2 | NB | NB | NB | NB |
| MAb16676 | 186 ± 0.58 | 0 | NB | NB | NB | NB |
| MAb16680 | 282 ± 0.79 | 1 | NB | NB | NB | NB |
| MAb16682 | 203 ± 0.54 | 1 | NB | NB | NB | NB |
| MAb16683 | 256 ± 0.27 | 0 | NB | NB | NB | NB |
| MAb16684 | 212 ± 1.24 | −2 | NB | NB | NB | NB |
| MAb16687 | 179 ± 0.18 | 1 | NB | NB | NB | NB |
| MAb16692 | 191 ± 0.49 | 7 | 2.39E+05 | 2.27E−01 | 9.50E−07 | 0.05 |
| MAb16693 | 174 ± 0.66 | 1 | NB | NB | NB | NB |
| MAb16695 | 184 ± 0.36 | 0 | NB | NB | NB | NB |
| MAb16702 | 210 ± 0.16 | 1 | NB | NB | NB | NB |
| IgG4 Isotype Control | 252 ± 0.45 | 1 | NB | NB | NB | NB |

NB indicates that no binding was observed under the current experimental conditions.

As shown in Tables 11 and 12, 2 out of 26 anti-GP130 monoclonal antibodies of the invention bound to rGP130-MMH. At 25° C., anti-GP130 monoclonal antibodies bound to rGP130-MMH with $K_D$ values ranging from 344 nM to 460 nM, as shown in Table 11. At 37° C., anti-GP130 monoclonal antibodies bound to rGP130-MMH with $K_D$ values ranging from 403 nM to 950 as shown in Table 12.

Example 4: Anti-GP130 Antibody Cell Binding by FACS Analysis

In order to assess cell binding by anti-GP130 antibodies of the invention two cell lines were generated. One cell line generated was HEK293 cells stably over-expressing full length (FL) human gp130 (amino acids 1-918 of accession #P40189 with leucine at position 2 changed to valine, a natural variant) along with a luciferase reporter (Stat3-luciferase, Stat3-luc, SA Bioscience, #CLS-6028L). The cells were sorted twice using flow cytometry for high expression of gp130. It is known hereafter as HEK293/Stat3-luc/gp130-2× Sort. IMR-32 cells (human Neuroblastoma, ATCC), were also evaluated for cell binding as these cells express gp130 endogenously and were used for bioassays. The cells used for binding were generated to stably express a luciferase reporter (Stat3-luciferase, Stat3-luc, SA Bioscience, #CLS-6028L), and are referred to hereafter as IMR-32/STAT3-Luc cells.

For the FACS analysis, 10 nM of the antibodies were used to stain 0.5×106 cells/well of each cell type at 4° C. in PBS (without calcium and magnesium) containing 2% FBS for 30 minutes. IMR-32/STAT3-luc cells were incubated with 1 mg/mL mouse IgG for 30 minutes at 4° C. to block Fc receptors prior to adding the antibodies. To test whether the anti-gp130 antibody binding is specific for gp130 on the IMR-32 cells, antibodies were added to IMR-32/Stat3-luc cells with or without being pre-bound to 1000 nM of recombinant protein of the ecto-domain of human gp130 fused to myc-myc-his tag (hgp130.mmh) for 30 minutes at 25° C. After incubation with primary antibodies, the cells were stained with 8 µg/mL of Alexa Fluor®-647 conjugated secondary antibody (Jackson ImmunoResearch Laboratories Inc., anti-human #109-607-003) for 30 minutes. Cells were fixed using BD CytoFix™ (Becton Dickinson, #554655) and analyzed on an IQue® (Intellicyt®) Flow Cytometer. Unstained and secondary antibody alone controls were also tested for all cell lines. The results were analyzed using ForeCyt® (IntelliCyt®) software to determine the geometric means of fluorescence for viable cells.

As shown in Table 13, twenty-six anti-gp130 antibodies of the invention tested at 10 nM demonstrated binding to HEK293/Stat3-luc/gp130-2× Sort cells with binding ratios ranging from 29- to 159-fold. The anti-gp130 antibodies demonstrated binding to the HEK293 parental cells with binding ratios 4- to 45-fold. Binding ratios to the IMR-32/Stat3-luc cells ranged from 5- to 23-fold without hgp130.mmh and from 4- to 9-fold with hGP130.mmh. The isotype control antibodies and secondary antibodies alone samples demonstrated binding ratios ranging from 1- to 3-fold for HEK293 cell lines, and 1- to 8-fold for IMR-32/Stat3-luc cells.

TABLE 13

Binding of 10 nM anti-gp130 antibodies to HEK293/Stat3-luc/gp130-2X Sort and IMR-32/Stat3-luc cells.

| | MFI - Normalized to Unstained Control | | | |
|---|---|---|---|---|
| | | | IMR-32/Stat3-luc | |
| Antibody | 293 Parental | 293/Stat3-luc/ GP130 2X sort | No hGP130.mmh | 1 uM hGP130.mmh |
| MAb16614 | 13 | 94 | 7 | 6 |
| MAb16618 | 13 | 105 | 7 | 8 |
| MAb16622 | 9 | 91 | 5 | 7 |
| MAb16623 | 14 | 96 | 8 | 7 |
| MAb16636 | 20 | 92 | 8 | 7 |
| MAb16637 | 22 | 121 | 9 | 7 |
| MAb16641 | 13 | 81 | 8 | 7 |
| MAb16646 | 6 | 29 | 5 | 6 |
| MAb16656 | 20 | 132 | 12 | 7 |
| MAb16659 | 14 | 81 | 8 | 8 |
| MAb16662 | 7 | 49 | 5 | 6 |
| MAb16664 | 8 | 45 | 7 | 8 |
| MAb16665 | 4 | 55 | 5 | 6 |
| MAb16666 | 45 | 159 | 23 | 8 |
| MAb16669 | 9 | 53 | 6 | 5 |
| MAb16673 | 15 | 107 | 10 | 7 |
| MAb16676 | 13 | 74 | 9 | 8 |
| MAb16680 | 21 | 99 | 11 | 9 |
| MAb16682 | 5 | 80 | 6 | 8 |
| MAb16683 | 13 | 75 | 9 | 7 |
| MAb16684 | 7 | 60 | 5 | 4 |
| MAb16687 | 12 | 71 | 9 | 7 |
| MAb16692 | 23 | 103 | 12 | 6 |
| MAb16693 | 4 | 51 | 7 | 7 |
| MAb16695 | 13 | 64 | 10 | 9 |
| MAb16702 | 25 | 111 | 11 | 6 |
| hIg4 Isotype Control | 3 | 2 | 6 | 7 |
| a-h 2" alone | 2 | 2 | 4 | 8 |
| Unstained | 1 | 1 | 1 | 1 |

Example 5: Octet Cross-Competition Between Different Anti-GP130 Monoclonal Antibodies Binding competition between a panel of anti-GP130 monoclonal antibodies was determined using a real time, label-free bio-layer interferometry assay on the Octet HTX biosensor platform (Pall ForteBio Corp.). The entire experiment was performed at 25° C. in 10 mM HEPES, 150 mM NaCl, 3 mM EDTA, 0.05% v/v Surfactant Tween-20, and 1 mg/mL BSA, pH7.4 (HBS-EBT) buffer with the plate shaking at the speed of 1000 rpm. To assess whether 2 antibodies compete with one another for binding to their respective epitopes on the recombinant human GP130 (hGP130-mmH; expressed with a C-terminal myc-myc-hexahistidine tag SEQ ID:188), about 0.4-0.5 nm of hGP130-mmH was first captured onto anti-Penta-His antibody coated Octet biosensor tips (Fortebio Inc, #18-5122) by submerging the biosensor tips for 4 minutes in wells containing 40-501.1 g/mL solution of hGP130-MMH. The antigen captured biosensor tips were then saturated with the first anti-GP130 monoclonal antibody (mAb-1) by dipping into wells containing 50 µg/mL solution of mAb-1 for 4 minutes. The biosensor tips were then dipped into wells containing 50 µg/mL solution of the second anti-GP130 monoclonal antibody (mAb-2) for 3 minutes. The biosensor tips were washed in HBS-ETB buffer between every step of the experiment. The real-time binding response was monitored during the entire course of the experiment and the binding response at the end of every step was recorded. The response of mAb-2 binding to hGP130-MMH pre-complexed with mAb-1 was compared and competitive/non-competitive behavior of different anti-GP130 monoclonal antibodies was determined as shown in Table 14.

TABLE 14

Cross-competition between anti-GP130 monoclonal antibodies

| mAb-1 | mAb-2 that competes with mAb-1 |
|---|---|
| MAb16659 | MAb16676 |
| | MAb16695 |
| | MAb16664 |
| | MAb16622 |
| | MAb16637 |
| MAb16676 | MAb16659 |
| | MAb16695 |
| | MAb16664 |
| | MAb16622 |
| | MAb16637 |
| MAb16695 | MAb16659 |
| | MAb16676 |
| | MAb16664 |
| | MAb16622 |
| | MAb16637 |
| MAb16664 | MAb16659 |
| | MAb16676 |
| | MAb16695 |
| | MAb16622 |
| | MAb16637 |
| MAb16622 | MAb16659 |
| | MAb16676 |
| | MAb16695 |
| | MAb16664 |
| | MAb16637 |
| | MAb16665 |
| | MAb16687 |
| | MAb16656 |
| MAb16637 | MAb16659 |
| | MAb16676 |
| | MAb16695 |
| | MAb16664 |
| | MAb16622 |

TABLE 14-continued

Cross-competition between anti-GP130 monoclonal antibodies

| mAb-1 | mAb-2 that competes with mAb-1 |
|---|---|
|  | MAb16665 |
|  | MAb16687 |
|  | MAb16656 |
| MAb16665 | MAb16622 |
|  | MAb16637 |
|  | MAb16687 |
|  | MAb16656 |
| MAb16687 | MAb16622 |
|  | MAb16637 |
|  | MAb16665 |
|  | MAb16656 |
| MAb16656 | MAb16622 |
|  | MAb16637 |
|  | MAb16665 |
|  | MAb16687 |
| MAb16641 | No mAb |
| MAb16666 | MAb16662 |
| MAb16662 | MAb16666 |
| MAb16618 | MAb16673 |
|  | MAb16636 |
|  | MAb16692 |
| MAb16673 | MAb16618 |
|  | MAb16636 |
|  | MAb16692 |
| MAb16636 | MAb16618 |
|  | MAb16673 |
|  | MAb16692 |
|  | MAb16614 |
|  | MAb16682 |
| MAb16692 | MAb16618 |
|  | MAb16673 |
|  | MAb16636 |
|  | MAb16614 |
|  | MAb16682 |
| MAb16614 | MAb16636 |
|  | MAb16692 |
|  | MAb16682 |
| MAb16682 | MAb16636 |
|  | MAb16692 |
|  | MAb16614 |
| MAb16623 | MAb16684 |
|  | MAb16702 |
|  | MAb16693 |
|  | MAb16669 |
| MAb16684 | MAb16623 |
|  | MAb16702 |
|  | MAb16693 |
|  | MAb16669 |
| MAb16702 | MAb16623 |
|  | MAb16684 |
|  | MAb16693 |
|  | MAb16669 |
| MAb16693 | MAb16623 |
|  | MAb16684 |
|  | MAb16702 |
|  | MAb16669 |
| MAb16669 | MAb16623 |
|  | MAb16684 |
|  | MAb16702 |
|  | MAb16693 |
| MAb16646 | MAb16680 |
| MAb16680 | MAb16646 |
| MAb16683 | No mAb |

Example 6: Monoclonal Antibodies Binding to GP130 Domain Proteins in Luminex-GP130 Delta D1-mmH and GP130 Delta D1-3-mmH CHO Supernatant To identify the binding region of human GP130 with which anti-GP130 antibodies of the invention interact, a Luminex FLEXMAP (FM3DD, LuminexCorp) flow cytometry based analysis was utilized to characterize the interaction of recombinant human GP130 protein domains. For the assay, approximately 3 million carboxylated Microplex$^R$ microspheres (Luminex, Cat #LC1000A), were washed, vortexed and sonicated in 0.1 M NaPO4, pH 6.2 (activation buffer) and then centrifuged to remove the supernatant. The microspheres were re-suspended in 120 μL of activation buffer and the carboxylate groups (—COOH) were activated by addition of 15 μL of 50 mg/mL of N-hydroxysuccinimide (NHS, Thermo Scientific, Cat #24500) followed by addition of 15 μL of 50 mg/mL of 1-ethyl-3-[3-dimethylaminopropyl]carbodiimide (EDC, ThermoScientific, Cat #22980) at 25° C. After 10 minutes, the pH of the reaction was reduced to 5.0 with the addition of 600 μL of 50 mM MES, pH 5 (coupling buffer), and the microspheres were vortexed, and centrifuged to remove supernatant. The activated beads were immediately mixed with 500 μL of 20 μg/mL monoclonal anti-myc antibodies with mouse IgG, in coupling buffer and incubated for two hours at 25° C. The coupling reaction was quenched by addition of 50 μL of 1M TRIS-HCl, pH 8.0 and the microspheres were rapidly vortexed, centrifuged, and washed four times with 1 mL of Dulbecco's 1× Phosphate Buffered Saline (DPBS, pH 7.2, ThermoScientific Cat #14190136), to remove uncoupled proteins and other reaction components.

The transiently expressed GP130 proteins, including human GP130 delta D1 expressed with a C-terminal myc-myc hexahistidine tag (human GP130 delta D1-MMH, SEQ ID NO:192) and human GP130 delta D1-D3 expressed with a C-terminal myc-myc hexahistidine tag (human GP130 delta D1-D3-MMH, SEQ ID NO:193), were suspended in serum free CHO—S-SFM II Medium (Thermo Fisher, Cat #31033020) and were then clarified by centrifugation. Purified GP130 full length extracellular domain expressed with a C-terminal myc-myc hexahistidine tag (human GP130-MMH, SEQ ID NO:191) was prepared at 10 ug/mL in PBS. Aliquots of microspheres with immobilized anti-myc monoclonal antibodies, prepared as described above, were added individually to 1 mL of the each of these protein supernatants and to 500 uL of purified GP130 protein. The microspheres were gently mixed, incubated for two hours at 25° C., washed twice with 1 mL of DBPS, centrifuged to remove the supernatant and finally resuspended in 1 mL of DPBS buffer. Forty eight μL of anti-myc IgG coupled microspheres from individual reactions with full length human GP130 and with each of the human GP130 domain proteins were withdrawn and mixed together in 3.6 mL of PBS+20 mg/mL BSA+0.05% sodium azide (blocking buffer).

From this mixed pool, 754 of microspheres were plated per well on a 96 well filter plate (Millipore, Cat. No: MSBVN1250) and mixed with 25 μL of individual anti-human GP130 monoclonal antibodies (0.5 or 5 μg/mL), incubated for two hours at 25° C. and then washed twice with 200 μL of DPBS with 0.05% Tween 20 (washing buffer). To detect and quantify the amounts of bound anti-GP130 antibody levels to individual microspheres, either 100 μL of 2.5 μg/mL R-Phycoerythrin conjugated goat F(ab')2 anti-human kappa (Southern Biotech, Cat #2063-09) in blocking buffer, was added and incubated for 30 minutes at 25° C. After 30 minutes, the samples were washed twice with 200 μL of washing buffer and resuspended in 150 μL of wash buffer. The Median Fluorescence intensity (MFI) of the microspheres was measured in a Luminex Analyzer.

TABLE 15

Luminex MFI signal of anti-GP130 antibodies binding to myc tag captured full-length extracellular domain of human GP130, isolated human GP130 delta D1 and delta D1-D3 domains.

| Antibody | GP130 Delta D1 extracellular domain | GP130 Delta D1-D3 extracellular domain | GP130 Full length extracellular domain | Interacting Domain(s) |
| --- | --- | --- | --- | --- |
| mAb16614 | 2899 | 56 | 18690 | D2-D3 |
| mAb16618 | 2634 | 19 | 18986 | D2-D3 |
| mAb16622 | 391 | 20 | 18462 | D2-D3 |
| mAb16623 | 12565 | 16012 | 17617 | FNIII |
| mAb16636 | 4261 | 1067 | 17617 | D2-D3 |
| mAb16637 | 342 | 861 | 16899 | D1 |
| mAb16641 | 51 | 27 | 17298 | D1 |
| mAb16646 | 11329 | 18005 | 13957 | FNIII |
| mAb16656 | 48 | 17 | 15911 | D1 |
| mAb16659 | 49 | 22 | 17092 | D1 |
| mAb16662 | 3050 | 16 | 13926 | D2-D3 |
| mAb16664 | 442 | 419 | 19306 | D1 |
| mAb16665 | 119 | 116 | 16332 | D1 |
| mAb16666 | 7280 | 319 | 16676 | D2-D3 |
| mAb16669 | 12643 | 15063 | 17640 | FNIII |
| mAb16673 | 2344 | 33 | 15065 | D2-D3 |
| mAb16676 | 364 | 686 | 18074 | D1 |
| mAb16680 | 10911 | 18713 | 14422 | FNIII |
| mAb16682 | 1380 | 13 | 13825 | D2-D3 |
| mAb16683 | 12026 | 20857 | 15220 | FNIII |
| mAb16684 | 9126 | 11992 | 14398 | FNIII |
| mAb16687 | 37 | 18 | 15485 | D1 |
| mAb16692 | 3893 | 17 | 16202 | D2-D3 |
| mAb16693 | 9449 | 12009 | 12943 | FNIII |
| mAb16695 | 30 | 7 | 14533 | D1 |
| mAb16702 | 11721 | 12500 | 14951 | FNIII |

The results of the Luminex based analysis are tabulated in Table 15. Luminex MFI signal intensities indicate that the twenty six anti-GP130 antibodies of the invention bound to the human GP130 full length extracellular domain.

Anti-GP130 antibodies mAb16637, mAb16641, mAb16656, mAb16659, mAb16664, mAb16665, mAb16676, mAb16687 and MAb16695 lost binding to both deletion proteins, suggesting binding epitopes within the D1 domain of human GP130. Anti-GP130 antibodies mAb16614, mAb16618, mAb16622, mAb16636, mAb16662, mAb16666, mAb16673, mAb16682, mAb16692 lost binding to GP130 delta D1-D3 while retaining binding to GP130 delta D1, indicating their binding epitope is within domains D2-D3 of human GP130.

Anti-GP130 antibodies mAb16623, mAb16646, mAb16669, mAb16680, mAb16683, mAb16684, mAb16693, mAb16702 bound to GP130 delta D1 and GP130 delta D1-D3, indicating their binding domain is within FNIII of human GP130.

Example 7: Functional Cell-Based Assay with in IMR-32/Stat3-Luc Cells, without Ligands or with hOncostain M, hLIF, or hCNTF In order to assess transcriptional activation or inhibition of anti-GP130 antibodies, IMR-32 cells (human Neuroblastoma ATCC) were generated to stably express a luciferase reporter (STAT3-Luc; SABiosciences, #CLS-6028L). The resulting cell line is referred to hereafter as IMR-32/STAT3-Luc (see Example 4 herein).

For the bioassay, IMR-32/STAT3-Luc cells were plated at 15,000 cells/well in a 96-well plate in assay buffer (0.1% FBS in Optimem with pen/strep) and incubated overnight at 37° C. in 5% $CO_2$. The following day anti-gp130 antibodies or an isotype control were serially diluted from 100 nM to 24.4 pM in assay buffer (plus a sample containing buffer alone without test molecule), added to the cells and incubated at 25° C. for 30 minutes. After 30 minutes, either 100 pM human Oncostatin M (hOSM, R&D System 293-OM), 20 pM human Leukemia Inhibitory Factor (hLIF, R&D Systems 7734-LF), 20 pM human Ciliary Neurotrophic Factor (hCNTF, R&D Systems 257-NT), or assay buffer was added to cells. hOSM, hLIF, and hCNTF were serially diluted from 10 nM to 0.17 pM in assay buffer (plus a sample containing buffer alone without test molecule) and added to cells not treated with antibodies. After 5 hours at 37° C. in 5% $CO_2$, luciferase activity was measured with OneGlo™ reagent (Promega, #E6031) and Victor™ X multilabel plate reader (Perkin Elmer). The results were analyzed using nonlinear regression (4-parameter logistics) with Prism 5 software (Graph Pad) to obtain $EC_{50}$ and $IC_{50}$ values. Activation of antibodies was calculated with the maximum range of RLU achieved by the antibody over the maximum range of RLU achieved by hOSM. The percentage of inhibition was calculated with the RLU values by using the following equation:

$$\% \text{ Inhibition} = 100 \times \frac{RLU_{Baseline} - RLU_{Inhibition}}{RLU_{Baseline} - RLU_{Background}}$$

In this equation "RLUBaseline" is the luminescence value from the cells treated with a constant amount of ligand (hOSM, hLIF, or hCNTF) without antibodies. "RLUInhibition" is the luminescence value with 100 nM of a particular antibody with a particular concentration of ligand, and "RLUBackground" is the luminescence value from cells without any ligands or antibodies.

As shown in Table 16, twenty-six anti-human gp130 antibodies of the invention were tested for their ability to either activate or inhibit activation of IMR-32/Stat3-luc cells. As shown in Table 19, in the absence of any added ligands none of the antibodies of the invention tested showed any activation of IMR-32/Stat3-luc cells. One of the 26 antibodies of the invention, MAb16692, showed complete inhibition of all three ligands tested with $IC_{50}$ values of 48 pM, 140 pM, and 230 pM for hOSM, hLIF, and hCNTF, respectively. An additional ten antibodies of the invention tested showed some inhibition of at least one of the ligands with the % inhibition ranging from 17% to 95%, with $IC_{50}$ values for the inhibiting antibodies ranging from >100 nM to 88 pM. Fifteen antibodies of the invention did not show inhibition of any of ligands tested. An isotype control antibody did not demonstrate any measureable activation or inhibition of IMR-32/stat3-luc cells. The ligands activated IMR-32/STAT3-luc cells with $EC_{50}$ values of 54 pM for hOSM, 23 pM for hLIF, and 4 pM for hCNTF.

TABLE 16

Activation and inhibition of anti-gp130 antibodies in the absence or presence of GP130 ligands in IMR-32/Stat3-luc cells.

| mAb PID | OSM (100 pM) | | LIF (20 pM) | | CNTF (20 pM) | | No Ligand |
|---|---|---|---|---|---|---|---|
| | IC50 [M] | % inhibition | IC50 [M] | % inhibition | IC50 [M] | % inhibition | EC50 [M] |
| mAb16614 | No Inhibition | No Inhibition | No Inhibition | No Inhibition | No Inhibition | No Inhibition | No Activation |
| mAb16618 | >5.0E−08 | 52 | >1.0E−07 | 40 | >1.0E−07 | 33 | No Activation |
| mAb16622 | No Inhibition | No Inhibition | No Inhibition | No Inhibition | No Inhibition | No Inhibition | No Activation |
| mAb16623 | No Inhibition | No Inhibition | No Inhibition | No Inhibition | >1.0E−07 | 22 | No Activation |
| mAb16636 | >1.0E−08 | 82 | >1.0E−08 | 76 | >1.0E−08 | 62 | No Activation |
| mAb16637 | No Inhibition | No Inhibition | No Inhibition | No Inhibition | No Inhibition | No Inhibition | No Activation |
| mAb16641 | 8.8E−11 | 21 | No Inhibition | No Inhibition | No Inhibition | No Inhibition | No Activation |
| mAb16646 | >1.0E−07 | 47 | >1.0E−07 | 26 | >1.0E−07 | 30 | No Activation |
| mAb16656 | No Inhibition | No Inhibition | No Inhibition | No Inhibition | No Inhibition | No Inhibition | No Activation |
| mAb16659 | No Inhibition | No Inhibition | No Inhibition | No Inhibition | No Inhibition | No Inhibition | No Activation |
| mAb16662 | No Inhibition | No Inhibition | No Inhibition | No Inhibition | No Inhibition | No Inhibition | No Activation |
| mAb16664 | No Inhibition | No Inhibition | No Inhibition | No Inhibition | No Inhibition | No Inhibition | No Activation |
| mAb16665 | No Inhibition | No Inhibition | No Inhibition | No Inhibition | No Inhibition | No Inhibition | No Activation |
| mAb16666 | No Inhibition | No Inhibition | No Inhibition | No Inhibition | 7.1E−10 | 95 | No Activation |
| mAb16669 | No Inhibition | No Inhibition | No Inhibition | No Inhibition | No Inhibition | No Inhibition | No Activation |
| mAb16673 | >5.0E−08 | 62 | 9.0E−09 | 52 | >1.0E−07 | 46 | No Activation |
| mAb16676 | No Inhibition | No Inhibition | No Inhibition | No Inhibition | No Inhibition | No Inhibition | No Activation |
| mAb16680 | 1.8E−09 | 71 | 3.4E−09 | 80 | 9.6E−10 | 35 | No Activation |
| mAb16682 | >1E−07 | 23 | No Inhibition | No Inhibition | No Inhibition | No Inhibition | No Activation |
| mAb16683 | No Inhibition | No Inhibition | No Inhibition | No Inhibition | No Inhibition | No Inhibition | No Activation |
| mAb16684 | No Inhibition | No Inhibition | No Inhibition | No Inhibition | No Inhibition | No Inhibition | No Activation |
| mAb16687 | No Inhibition | No Inhibition | No Inhibition | No Inhibition | No Inhibition | No Inhibition | No Activation |
| mAb16692 | 4.8E−11 | 101 | 1.4E−10 | 101 | 2.3E−10 | 100 | No Activation |
| mAb16693 | No Inhibition | No Inhibition | No Inhibition | No Inhibition | No Inhibition | No Inhibition | No Activation |
| mAb16695 | No Inhibition | No Inhibition | No Inhibition | No Inhibition | No Inhibition | No Inhibition | No Activation |
| mAb16702 | No Inhibition | No Inhibition | No Inhibition | No Inhibition | >1E−07 | 17 | No Activation |
| Isotype Control mAb | No Inhibition | No Inhibition | No Inhibition | No Inhibition | No Inhibition | No Inhibition | No Activation |

Example 8: GP130 Purified Antibodies Blocking ELISA

GP130 (glycoprotein 130) is a type I cytokine receptor transmembrane protein which forms a high-affinity ternary complex with the ligand ciliary neurotropic factor (CNTF) when it is associated with CNTFRα (ciliary neurotropic factor receptor alpha subunit). The ability of anti-gp130 antibodies to block GP130 protein binding to plate bound CNTFRα/CNTF complex was measured using a competition sandwich ELISA. In this assay, various concentrations of anti-gp130 antibody were pre-mixed with a constant amount of dimeric GP130 protein and the reduction of the gp130 binding due to the presence of the antibody to the plate immobilized CNTFRα/CNTF complex was monitored.

The dimeric gp130 protein used in the experiments was comprised of a portion of the human gp130 extracellular domain (amino acids E23-E619 of accession number NP_002175.2) expressed with the Fc portion of the mouse IgG2a protein at the c-terminus (hGP130-mFc; SEQ ID:190, mw 94,210 daltons). The CNTFRα protein was purchased from R&D Systems (amino acids Q23-P346 of accession #6992, mw 36,000 daltons). The CNTF protein was purchased from R&D Systems (amino acids A2-M200 of accession #6441.1, mw 22,800 daltons). Isotype antibody control, anti-Fel d 1, and human IgG4$^P$ antibody were included as controls for IgG background detection.

The experiment was carried out using the following procedure. Human CNTFRα was coated at a concentration of 2 mg/mL in HBSS on a 96-well microtiter plate overnight at 4° C. Nonspecific binding sites were subsequently blocked using a 1% (w/v) solution of BSA in HBSS. Human CNTF at a concentration of 1 μg/ml in HBSS was added to the plate bound CNTFRα for 1 hour at room temperature. In separate dilution plates, a constant amount of 2.5 nM of human GP130-mFc protein was titrated with antibodies ranging from 3.4 pM to 200 nM in serial dilution and with no antibody present. These solutions were incubated for 1 hour at room temperature (RT) and subsequently transferred to the microtiter plates with CNTFRα/CNTF complex without washing. The plates were incubated for 2 hours at RT, washed with PBST buffer, and plate-bound hGP130-mFc was detected with an anti-mFc polyclonal antibody conjugated with horseradish peroxidase (HRP) (Jackson ImmunoResearch Inc). Samples were developed with a TMB solution (BD Biosciences, substrate A and B mixed at 1:1 ratio as per manufacturer's instructions) to produce a colorimetric reaction and then neutralized with 1M sulfuric acid before measuring absorbance at 450 nm on a Victor X5 plate reader.

Data analysis was performed using a sigmoidal dose-response model within Prism™ software (GraphPad). The calculated $IC_{50}$ value, defined as the concentration of antibody required to reduce 50% of GP130 binding to CNTFRα/CNTF complex, was used as an indicator of blocking potency. Percent blockade at maximum concentration tested was calculated as an indicator of the ability of the antibodies to block binding of GP130 to CNTFRα/CNTF on the plate as determined from the dose curve. The ratio of the reduction in signal observed in the presence of the highest tested concentration of 200 nM antibody, relative to the difference between the signal with 2.5 nM GP130 with no antibody (0% blocking) and the background signal from HRP-conjugated secondary antibody alone (100% blocking), was subtracted from 100% blocking.

The results of the blocking ELISA are shown in Table 17 with blocking percentages in the presence of 200 nM antibody reported for all antibodies. $IC_{50}$ values are reported only for antibodies blocking >30% of GP130 binding to CNTFRα/CNTF. Nineteen of twenty-six a-GP130 antibodies block <30% GP130 protein binding to plate-coated CNTFRα/CNTF. Negative numbers indicate an increase of GP130 binding detected in the presence of antibody. Seven antibodies blocked GP130 protein binding to CNTFRα/CNTF >30% and $IC_{50}$ values ranged from below the lower limit of quantitation for the assay of 1.25 nM to 6.5 nM, with four of them blocking 90% or more of the signal at the highest antibody concentration tested. The irrelevant blocking control antibody showed blocking of 4.5% at concentrations up to 200 nM.

TABLE 17

GP130 Purified Antibodies Blocking ELISA

| Antibody Identifier | Lot # | Max Blocking of Antibody at 200 nM (%) | Potency of Antibody Blocking 2.5 nM hGP130-mFc binding to plate-bound CNTFR/CNTF complex (M) |
|---|---|---|---|
| mAb16614 | MAb16614-L1 | −14.75 | — |
| mAb16618 | MAb16618-L1 | 86.65 | 2.374E−09 |
| mAb16622 | MAb16622-L1 | −84.14 | — |
| mAb16623 | MAb16623-L1 | −49.19 | — |
| mAb16636 | MAb16636-L1 | 94.76 | 1.104E−09 |
| mAb16637 | MAb16637-L1 | −38.86 | — |
| mAb16641 | MAb16641-L1 | 14.09 | — |
| mAb16646 | MAb16646-L1 | 5.24 | — |
| mAb16656 | MAb16656-L1 | −24.71 | — |
| mAb16659 | MAb16659-L1 | −18.81 | — |
| mAb16662 | MAb16662-L1 | 81.93 | 6.506E−09 |
| mAb16664 | MAb16664-L1 | −46.53 | — |
| mAb16665 | MAb16665-L1 | −47.12 | — |
| mAb16666 | MAb16666-L1 | 103.39 | 6.437E−10* |
| mAb16669 | MAb16669-L1 | 47.12 | 1.232E−08 |
| mAb16673 | MAb16673-L1 | 103.76 | 2.368E−09 |
| mAb16676 | MAb16676-L1 | −15.41 | — |
| mAb16680 | MAb16680-L1 | 11.95 | — |
| mAb16682 | MAb16682-L1 | −3.39 | — |
| mAb16683 | MAb16683-L1 | −22.79 | — |
| mAb16684 | MAb16684-L1 | 12.91 | — |
| mAb16687 | MAb16687-L1 | −17.40 | — |
| mAb16692 | MAb16692-L1 | 101.77 | 7.671E−10* |
| mAb16693 | MAb16693-L1 | 4.42 | — |
| mAb16695 | MAb16695-L1 | 21.17 | — |
| mAb16702 | MAb16702-L1 | 29.13 | — |
| hIgG4 Isotype Control | 07-120309 | 4.50 | — |

In this Example, 100% blocking is equal to OD450nm value HRP-conjugated secondary antibody with no GP130.
0% blocking is OD450nm value with 2.5 nM hGP130-mFc with no antibody.
Negative Max Blocking % indicates an increase of GP130 binding detected in the presence of antibody.
— $IC_{50}$ values are not quantitative for antibodies blocking <30% at the highest concentration tested.
*Indicates $IC_{50}$ value below the lower limit of quantitation of 1.25E−09M for the assay.

Example 9: LEPR×GP130 Focused Approach Bispecific Screening

This Example describes the generation of bispecific antibodies that bind to both LEPR and GP130 for the promotion of STAT3 signaling. Such antibodies are referred to herein as "LEPR×GP130 bispecific antibodies," or "LEPR×GP130 bsAbs," "anti-LEPR x anti-GP130 bispecific antibodies," or the like. In this Example, several anti-GP130 binding arms were paired with four different anti-LEPR binding arms. The anti-LEPR antibodies used to construct the bispecific antibodies of this Example are the agonistic antibodies referred to as mAb16679, mAb18445, mAb18446 and mAb18449 (see US Patent Appl. Publ. No. 2017/0101477, the disclosure of which is incorporated by reference herein in its entirety). The amino acid and nucleic acid sequences of the variable domains and CDRs of the anti-LEPR antibodies used in this Example are summarized in Tables 18 and 19, respectively.

TABLE 18 anti-LEPR Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb16679 | 2 | 4 | 6 | 8 | 10 | 12 | 14 | 16 |
| mAb18449 | 162 | 164 | 166 | 168 | 10 | 12 | 14 | 16 |
| mAb18445 | 170 | 172 | 174 | 176 | 10 | 12 | 14 | 16 |
| mAb18446 | 178 | 180 | 182 | 184 | 10 | 12 | 14 | 16 |

TABLE 19 anti-LEPR Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb16679 | 1 | 3 | 5 | 7 | 9 | 11 | 13 | 15 |
| mAb18449 | 161 | 163 | 165 | 167 | 9 | 11 | 13 | 15 |
| mAb18445 | 169 | 171 | 173 | 175 | 9 | 11 | 13 | 15 |
| mAb18446 | 177 | 179 | 181 | 183 | 9 | 11 | 13 | 15 |

Eighteen bispecific antibodies were generated through pairing of anti-LEPR binding arms from mAb16679 with binding arms from 18 different anti-GP130 antibodies. Six additional bispecific antibodies were created by pairing binding arms from anti-LEPR antibodies mAb18449, mAb18445 and mAb18446 with anti-GP130 binding arms. Standard methods were used to produce the bispecific antibodies described herein. All LEPR×GP130 bispecific antibodies shown in this example comprise the same ("common") light chain (comprising the light chain variable region [LCVR] amino acid sequence of SEQ ID NO:10, and light chain CDR [LCDR1, LCDR2 and LCDR3] amino acid sequences of SEQ ID NOs: 12, 14 and 16). The components of the bispecific antibodies of this Example are summarized in Table 20.

TABLE 20

LEPR × GP130 Bispecific Antibody Components Summary.

| Bispecific Antibody | LEPR Binding Arm Domain (D1) | | | | GP130 Binding Arm Domain (D2) | | | |
|---|---|---|---|---|---|---|---|---|
| | D1-HCVR | D1-HCDR1 | D1-HCDR2 | D1-HCDR3 | D2-HCVR | D2-HCDR1 | D2-HCDR2 | D2-HCDR3 |
| bsAb19139D | mAb16679 | | | | mAb 16614 | | | |
| | 2 | 4 | 6 | 8 | 18 | 20 | 22 | 24 |
| bsAb19140D | mAb 16679 | | | | mAb 16618 | | | |
| | 2 | 4 | 6 | 8 | 26 | 28 | 30 | 32 |
| bsAb19141D | mAb 16679 | | | | mAb 16622 | | | |
| | 2 | 4 | 6 | 8 | 34 | 36 | 38 | 40 |
| bsAb19142D | mAb 16679 | | | | mAb 16623 | | | |
| | 2 | 4 | 6 | 8 | 42 | 44 | 46 | 48 |
| bsAb19143D | mAb 16679 | | | | mAb 16636 | | | |
| | 2 | 4 | 6 | 8 | 50 | 52 | 54 | 56 |
| bsAb19144D | mAb 16679 | | | | mAb 16637 | | | |
| | 2 | 4 | 6 | 8 | 58 | 60 | 62 | 64 |
| bsAb19145D | mAb 16679 | | | | mAb 16656 | | | |
| | 2 | 4 | 6 | 8 | 66 | 68 | 70 | 72 |
| bsAb19146D | mAb 16679 | | | | mAb 16659 | | | |
| | 2 | 4 | 6 | 8 | 74 | 76 | 78 | 80 |
| bsAb19147D | mAb16679 | | | | mAb16662 | | | |
| | 2 | 4 | 6 | 8 | 82 | 84 | 86 | 88 |
| bsAb19148D | mAb16679 | | | | mAb16664 | | | |
| | 2 | 4 | 6 | 8 | 90 | 92 | 94 | 96 |
| bsAb19149D | mAb16679 | | | | mAb16665 | | | |
| | 2 | 4 | 6 | 8 | 98 | 100 | 102 | 104 |
| bsAb19150D | mAb16679 | | | | mAb16666 | | | |
| | 2 | 4 | 6 | 8 | 106 | 108 | 110 | 112 |
| bsAb19151D | mAb16679 | | | | mAb16669 | | | |
| | 2 | 4 | 6 | 8 | 114 | 116 | 118 | 120 |
| bsAb19152D | mAb16679 | | | | mAb16673 | | | |
| | 2 | 4 | 6 | 8 | 122 | 124 | 126 | 128 |
| bsAb19153D | mAb16679 | | | | mAb16676 | | | |
| | 2 | 4 | 6 | 8 | 130 | 132 | 134 | 136 |
| bsAb19154D | mAb16679 | | | | mAb16680 | | | |
| | 2 | 4 | 6 | 8 | 138 | 140 | 142 | 144 |
| bsAb19155D | mAb16679 | | | | mAb16682 | | | |
| | 2 | 4 | 6 | 8 | 146 | 148 | 150 | 152 |
| bsAb19156D | mAb16679 | | | | mAb16683 | | | |
| | 2 | 4 | 6 | 8 | 154 | 156 | 158 | 160 |
| bsAb19757D | mAb18449 | | | | mAb16622 | | | |
| | 162 | 164 | 166 | 168 | 34 | 36 | 38 | 40 |
| bsAb19758D | mAb18449 | | | | mAb16666 | | | |
| | 162 | 164 | 166 | 168 | 106 | 108 | 110 | 112 |
| bsAb21236D | mAb18445 | | | | mAb16683 | | | |
| | 170 | 172 | 174 | 176 | 154 | 156 | 158 | 160 |
| bsAb21237D | mAb18446 | | | | mAb16683 | | | |
| | 178 | 180 | 182 | 184 | 154 | 156 | 158 | 160 |
| bsAb27679D | mAb18445 | | | | mAb16683 | | | |
| | 170 | 172 | 174 | 176 | 154 | 156 | 158 | 160 |
| bsAb27680D | mAb18446 | | | | mAb16683 | | | |
| | 178 | 180 | 182 | 184 | 154 | 156 | 158 | 160 |

Example 10: Biacore Binding Kinetics of Anti-LEPR×Anti-GP130 Bispecific Antibodies Binding to Different GP130 Reagents Measured at 25° C. and 37° C.

Equilibrium dissociation constants ($K_D$ values) for LEPR and GP130 binding to purified anti-LEPR/GP130 bispecific antibodies were determined using a real-time surface plasmon resonance biosensor using a Biacore 4000 instrument. All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore sensor surface was first derivatized by amine coupling with a monoclonal mouse anti-human Fc antibody (GE, #BR-1008-39) to capture anti-LEPR/GP130 bispecific antibodies. Binding studies were performed on following reagents: human LEPR extracellular domain expressed with a C-terminal myc-myc-hexahistidine tag (hLEPR-MMH; SEQ ID NO:187), *Macaca fascicularis* LEPR extracellular domain expressed with a C-terminal myc-myc-hexahistidine tag (mfLEPR-MMH; SEQ ID NO: 188), human GP130 extracellular domain expressed with a C-terminal myc-myc-hexahistidine tag (hGP130-MMH; SEQ ID NO:191), and *Macaca fascicularis* GP130 extracellular domain expressed with a C-terminal myc-myc-hexahistidine tag (mfGP130-MMH; SEQ ID NO:194). Different concentrations of LEPR or GP130 reagents were first prepared in HBS-ET running buffer (100 nM-3.7 nM; 3-fold serial dilution) and were injected over anti-human Fc captured anti-LEPR/GP130 bispecific antibody surface for 4 minutes at a flow rate of 304/minute, while the dissociation of bispecific antibody bound LEPR or GP130 reagent was monitored for 10 minutes in HBS-ET running buffer. Kinetic association ($k_a$) and dissociation ($k_d$) rate constants were determined by fitting the real-time binding sensorgrams to a 1:1 binding model with mass transport limitation using Scrubber 2.0c curve-fitting software. Binding dissociation equilibrium constants ($K_D$) and dissociative half-lives ($t_{1/2}$) were calculated from the kinetic rate constants as:

$$K_D(M) = \frac{kd}{ka}, \text{ and } t\frac{1}{2}(\min) = \frac{\ln(2)}{60*kd}.$$

Binding kinetics parameters for hLEPR-MMH, mfLEPR-MMH, hGP130-MMH or mfGP130-MMH binding to different anti-LEPR/GP130 bispecific antibodies of the invention at 25° C. and 37° C. are shown in Tables 21 through 28.

TABLE 21

Binding kinetics parameters of hLEPR-MMH binding to anti-LEPR/GP130 bispecific antibodies at 25° C.

| Bispecific Antibody | mAb Capture Level (RU) | 100 nM hLEPR-MMH Bound (RU) | $k_a$ (1/Ms) | $k_d$ (1/s) | $K_D$ (M) | t½ (min) |
|---|---|---|---|---|---|---|
| bsAb19139D | 418 ± 0.5 | 41 | 2.41E+04 | 1.71E−04 | 7.09E−09 | 68 |
| bsAb19140D | 444 ± 0.7 | 47 | 2.45E+04 | 1.80E−04 | 7.36E−09 | 64 |
| bsAb19141D | 458 ± 2.5 | 45 | 2.54E+04 | 1.51E−04 | 5.91E−09 | 77 |
| bsAb19142D | 452 ± 2.1 | 46 | 2.25E+04 | 1.75E−04 | 7.76E−09 | 66 |
| bsAb19143D | 446 ± 1.6 | 45 | 2.49E+04 | 1.82E−04 | 7.31E−09 | 64 |
| bsAb19144D | 456 ± 2.6 | 48 | 2.46E+04 | 1.59E−04 | 6.48E−09 | 73 |
| bsAb19145D | 437 ± 1.2 | 41 | 2.49E+04 | 1.65E−04 | 6.62E−09 | 70 |
| bsAb19146D | 461 ± 1 | 45 | 2.20E+04 | 1.79E−04 | 8.16E−09 | 64 |
| bsAb19147D | 439 ± 0.7 | 42 | 2.27E+04 | 1.62E−04 | 7.13E−09 | 71 |
| bsAb19148D | 452 ± 1.1 | 44 | 2.36E+04 | 1.72E−04 | 7.31E−09 | 67 |
| bsAb19149D | 446 ± 1.4 | 36 | 2.71E+04 | 1.94E−04 | 7.16E−09 | 60 |
| bsAb19150D | 451 ± 2.9 | 41 | 2.40E+04 | 1.76E−04 | 7.35E−09 | 66 |
| bsAb19151D | 419 ± 1.3 | 46 | 2.11E+04 | 1.58E−04 | 7.49E−09 | 73 |
| bsAb19152D | 455 ± 2 | 47 | 2.45E+04 | 1.65E−04 | 6.75E−09 | 70 |
| bsAb19153D | 441 ± 1.9 | 40 | 2.55E+04 | 1.65E−04 | 6.46E−09 | 70 |
| bsAb19154D | 438 ± 0.7 | 40 | 2.26E+04 | 1.80E−04 | 7.95E−09 | 64 |
| bsAb19155D | 431 ± 0.7 | 40 | 2.40E+04 | 1.53E−04 | 6.36E−09 | 76 |
| bsAb19156D | 439 ± 0.8 | 39 | 2.31E+04 | 1.64E−04 | 7.11E−09 | 70 |
| bsAb19757D | 432 ± 1.3 | 57 | 2.07E+04 | 1.62E−04 | 7.85E−09 | 71 |
| bsAb19758D | 428 ± 4.1 | 54 | 1.59E+04 | 1.63E−04 | 1.03E−08 | 71 |
| bsAb21236D | 78 ± 0.3 | 8 | 3.51E+04 | 3.72E−03 | 1.06E−07 | 3.1 |
| bsAb21237D | 206 ± 0.6 | 11 | 1.53E+04 | 1.21E−03 | 7.87E−08 | 10 |
| Isotype Control | 427 ± 0.8 | −2 | NB* | NB* | NB* | NB* |

*NB indicates that no binding was observed under the current experimental conditions.

TABLE 22

Binding kinetics parameters of hLEPR-MMH binding to anti-LEPR/GP130 bispecific antibodies at 37° C.

| Bispecific Antibody | mAb Capture Level (RU) | 100 nM hLEPR-MMH Bound (RU) | $k_a$ (1/Ms) | $k_d$ (1/s) | $K_D$ (M) | t½ (min) |
|---|---|---|---|---|---|---|
| bsAb19139D | 527 ± 1.6 | 67 | 3.58E+04 | 7.62E-04 | 2.12E-08 | 15 |
| bsAb19140D | 559 ± 0.3 | 75 | 3.82E+04 | 8.18E-04 | 2.14E-08 | 14 |
| bsAb19141D | 582 ± 2.7 | 74 | 3.54E+04 | 5.89E-04 | 1.66E-08 | 20 |
| bsAb19142D | 551 ± 2.7 | 74 | 3.40E+04 | 6.33E-04 | 1.86E-08 | 18 |
| bsAb19143D | 558 ± 1.5 | 72 | 3.55E+04 | 7.63E-04 | 2.15E-08 | 15 |
| bsAb19144D | 568 ± 1.9 | 78 | 3.68E+04 | 5.97E-04 | 1.62E-08 | 19 |
| bsAb19145D | 558 ± 1.4 | 66 | 3.86E+04 | 8.05E-04 | 2.08E-08 | 14 |
| bsAb19146D | 576 ± 1 | 69 | 3.87E+04 | 8.25E-04 | 2.13E-08 | 14 |
| bsAb19147D | 547 ± 2.1 | 65 | 3.85E+04 | 7.91E-04 | 2.05E-08 | 15 |
| bsAb19148D | 565 ± 0.5 | 69 | 3.90E+04 | 7.98E-04 | 2.05E-08 | 14 |
| bsAb19149D | 566 ± 3.2 | 61 | 3.38E+04 | 6.22E-04 | 1.84E-08 | 19 |
| bsAb19150D | 544 ± 2.4 | 63 | 3.55E+04 | 6.91E-04 | 1.95E-08 | 17 |
| bsAb19151D | 525 ± 1.9 | 70 | 4.14E+04 | 7.60E-04 | 1.83E-08 | 15 |
| bsAb19152D | 568 ± 2 | 74 | 3.77E+04 | 7.87E-04 | 2.08E-08 | 15 |
| bsAb19153D | 557 ± 1.7 | 65 | 4.01E+04 | 7.91E-04 | 1.97E-08 | 15 |
| bsAb19154D | 540 ± 0.9 | 65 | 3.79E+04 | 7.29E-04 | 1.92E-08 | 16 |
| bsAb19155D | 536 ± 1.5 | 63 | 3.97E+04 | 7.92E-04 | 2.00E-08 | 15 |
| bsAb19156D | 539 ± 1 | 60 | 3.66E+04 | 8.42E-04 | 2.30E-08 | 14 |
| bsAb19757D | 543 ± 2.4 | 81 | 3.28E+04 | 6.25E-04 | 1.91E-08 | 18 |
| bsAb19758D | 519 ± 2.3 | 73 | 3.23E+04 | 6.63E-04 | 2.06E-08 | 17 |
| bsAb21236D | 68 ± 0.9 | 5 | 1.80E+04 | 1.31E-02 | 7.26E-07 | 0.9 |
| bsAb21237D | 269 ± 1.5 | 15 | 1.58E+04 | 4.42E-03 | 2.80E-07 | 2.6 |
| Isotype Control mAb | 540 ± 1.5 | -1 | NB* | NB* | NB* | NB* |

*NB indicates that no binding was observed under the current experimental conditions.

At 25° C., anti-LEPR/GP130 bispecific antibodies bound to hLEPR-MMH with $K_D$ values ranging from 5.91 nM to 106 nM, as shown in Table 21. At 37° C., anti-LEPR monoclonal antibodies bound to hLEPR-MMH with $K_D$ values ranging from 16.2 nM to 726 nM, as shown in Table 22.

TABLE 23

Binding kinetics parameters of mfLEPR-MMH binding to anti-LEPR/GP130 bispecific antibodies at 25° C.

| Bispecific Antibody | mAb Capture Level (RU) | 100 nM mfLEPR-MMH Bound (RU) | $k_a$ (1/Ms) | $k_d$ (1/s) | $K_D$ (M) | t½ (min) |
|---|---|---|---|---|---|---|
| bsAb19139D | 417 ± 0.9 | 103 | 4.36E+04 | 1.28E-04 | 2.93E-09 | 90 |
| bsAb19140D | 442 ± 0.7 | 112 | 4.50E+04 | 1.21E-04 | 2.69E-09 | 95 |
| bsAb19141D | 457 ± 0.9 | 110 | 4.33E+04 | 1.24E-04 | 2.86E-09 | 93 |
| bsAb19142D | 450 ± 1.8 | 112 | 4.59E+04 | 1.26E-04 | 2.74E-09 | 92 |
| bsAb19143D | 445 ± 1.7 | 111 | 4.48E+04 | 1.36E-04 | 3.04E-09 | 85 |
| bsAb19144D | 455 ± 3 | 114 | 4.11E+04 | 1.24E-04 | 3.02E-09 | 93 |
| bsAb19145D | 436 ± 1.2 | 102 | 4.49E+04 | 1.23E-04 | 2.75E-09 | 94 |
| bsAb19146D | 460 ± 0.9 | 107 | 4.29E+04 | 1.13E-04 | 2.63E-09 | 102 |
| bsAb19147D | 437 ± 0.6 | 107 | 4.25E+04 | 1.19E-04 | 2.80E-09 | 97 |
| bsAb19148D | 452 ± 0.7 | 107 | 4.13E+04 | 1.19E-04 | 2.88E-09 | 97 |
| bsAb19149D | 446 ± 1 | 96 | 4.19E+04 | 1.11E-04 | 2.65E-09 | 104 |
| bsAb19150D | 449 ± 3.6 | 102 | 4.18E+04 | 1.17E-04 | 2.79E-09 | 99 |
| bsAb19151D | 418 ± 1.5 | 109 | 4.25E+04 | 1.17E-04 | 2.74E-09 | 99 |
| bsAb19152D | 454 ± 2.7 | 113 | 4.18E+04 | 1.24E-04 | 2.97E-09 | 93 |
| bsAb19153D | 440 ± 1.5 | 102 | 4.26E+04 | 1.26E-04 | 2.96E-09 | 92 |
| bsAb19154D | 436 ± 0.7 | 102 | 4.08E+04 | 1.21E-04 | 2.96E-09 | 96 |
| bsAb19155D | 429 ± 0.9 | 103 | 4.20E+04 | 1.22E-04 | 2.90E-09 | 95 |
| bsAb19156D | 439 ± 0.7 | 97 | 4.04E+04 | 1.32E-04 | 3.27E-09 | 87 |
| bsAb19757D | 429 ± 1.5 | 7 | IC# | IC# | IC# | IC# |
| bsAb19758D | 426 ± 3 | 9 | 3.86E+04 | 2.25E-02 | 5.83E-07 | 0.5 |

TABLE 23-continued

Binding kinetics parameters of mfLEPR-MMH binding to anti-LEPR/GP130 bispecific antibodies at 25° C.

| Bispecific Antibody | mAb Capture Level (RU) | 100 nM mfLEPR-MMH Bound (RU) | $k_a$ (1/Ms) | $k_d$ (1/s) | $K_D$ (M) | $t\frac{1}{2}$ (min) |
|---|---|---|---|---|---|---|
| bsAb21236D | 119 ± 0.3 | 12 | 5.79E+04 | 4.82E−03 | 8.34E−08 | 2.4 |
| bsAb21237D | 190 ± 0.6 | 16 | 3.08E+04 | 1.16E−03 | 3.78E−08 | 10 |
| Isotype Control | 426 ± 1.1 | 1 | NB* | NB* | NB* | NB* |

*NB indicates that no binding was observed under the current experimental conditions.
IC indicates that observed binding signal was less than three-fold above to the non-specific binding observed for isotype control antibody surface and/or the data cannot be used to measure binding kinetic parameters.

TABLE 24

Binding kinetics parameters of mfLEPR-MMH binding to anti-LEPR/GP130 bispecific antibodies at 37° C.

| Bispecific Antibody | mAb Capture Level (RU) | 100 nM mfLEPR-MMH Bound (RU) | $k_a$ (1/Ms) | $k_d$ (1/s) | $K_D$ (M) | $t\frac{1}{2}$ (min) |
|---|---|---|---|---|---|---|
| bsAb19139D | 524 ± 1.2 | 163 | 1.03E+05 | 5.59E−04 | 5.42E−09 | 21 |
| bsAb19140D | 555 ± 0.8 | 175 | 1.02E+05 | 5.72E−04 | 5.60E−09 | 20 |
| bsAb19141D | 579 ± 1 | 173 | 1.03E+05 | 5.22E−04 | 5.05E−09 | 22 |
| bsAb19142D | 546 ± 3.5 | 172 | 9.49E+04 | 5.29E−04 | 5.57E−09 | 22 |
| bsAb19143D | 555 ± 1 | 171 | 9.59E+04 | 5.51E−04 | 5.74E−09 | 21 |
| bsAb19144D | 567 ± 1.5 | 178 | 9.91E+04 | 5.17E−04 | 5.22E−09 | 22 |
| bsAb19145D | 554 ± 1.3 | 162 | 1.03E+05 | 5.66E−04 | 5.48E−09 | 20 |
| bsAb19146D | 573 ± 1.6 | 164 | 1.00E+05 | 5.68E−04 | 5.68E−09 | 20 |
| bsAb19147D | 542 ± 1.3 | 163 | 1.00E+05 | 5.65E−04 | 5.64E−09 | 20 |
| bsAb19148D | 561 ± 1 | 163 | 9.25E+04 | 5.71E−04 | 6.17E−09 | 20 |
| bsAb19149D | 564 ± 1.8 | 154 | 6.25E+04 | 5.06E−04 | 8.09E−09 | 23 |
| bsAb19150D | 543 ± 3.4 | 158 | 9.89E+04 | 5.19E−04 | 5.25E−09 | 22 |
| bsAb19151D | 521 ± 1.2 | 167 | 1.05E+05 | 5.54E−04 | 5.30E−09 | 21 |
| bsAb19152D | 564 ± 1.7 | 169 | 9.99E+04 | 5.89E−04 | 5.90E−09 | 20 |
| bsAb19153D | 552 ± 1.2 | 158 | 6.58E+04 | 5.80E−04 | 8.81E−09 | 20 |
| bsAb19154D | 536 ± 1.2 | 159 | 9.60E+04 | 5.41E−04 | 5.64E−09 | 21 |
| bsAb19155D | 532 ± 1.3 | 155 | 1.03E+05 | 5.65E−04 | 5.49E−09 | 20 |
| bsAb19156D | 537 ± 1.4 | 148 | 9.64E+04 | 5.67E−04 | 5.88E−09 | 20 |
| bsAb19757D | 539 ± 1.3 | 7 | IC# | IC# | IC# | IC# |
| bsAb19758D | 517 ± 1.1 | 5 | IC# | IC# | IC# | IC# |
| bsAb21236D | 118 ± 1.3 | 9 | 6.19E+04 | 1.76E−02 | 2.84E−07 | 0.7 |
| bsAb21237D | 249 ± 0.6 | 27 | 2.81E+04 | 4.24E−03 | 1.51E−07 | 2.7 |
| Isotype Control | 536 ± 1.4 | 3 | NB* | NB* | NB* | NB* |

*NB indicates that no binding was observed under the current experimental conditions.
IC indicates that observed binding signal was less than three-fold above to the non-specific binding observed for isotype control antibody surface and/or the data cannot be used to measure binding kinetic parameters.

At 25° C., 21 out of 22 anti-LEPR/GP130 bispecific antibodies of the invention bound to mfLEPR-MMH with $K_D$ values ranging from 2.63 nM to 583 nM, as shown in Table 23. At 37° C., 20 out of 22 anti-LEPR/GP130 bispecific antibodies of the invention bound to mfLEPR-MMH with $K_D$ values ranging from 5.05 nM to 284 nM, as shown in Table 24.

TABLE 25

Binding kinetics parameters of hGP130-MMH binding to anti-LEPR/GP130 bispecific antibodies at 25° C.

| Bispecific Antibody | mAb Capture Level (RU) | 100 nM hGP130-MMH Bound (RU) | $k_a$ (1/Ms) | $k_d$ (1/s) | $K_D$ (M) | $t^{1/2}$ (min) |
|---|---|---|---|---|---|---|
| bsAb19139D | 168 ± 0.3 | 6 | IC# | IC# | IC# | IC# |
| bsAb19140D | 182 ± 0.3 | 23 | 4.55E+05 | 4.77E−02 | 1.05E−07 | 0.2 |
| bsAb19141D | 183 ± 0.5 | 15 | 1.06E+05 | 2.32E−02 | 2.19E−07 | 0.5 |
| bsAb19142D | 184 ± 0.8 | 31 | 1.73E+05 | 3.29E−03 | 1.90E−08 | 4 |
| bsAb19143D | 178 ± 0.6 | 16 | 3.20E+04 | 6.47E−04 | 2.02E−08 | 18 |
| bsAb19144D | 183 ± 1 | 27 | 6.43E+04 | 7.77E−04 | 1.21E−08 | 15 |
| bsAb19145D | 176 ± 0.3 | 19 | 3.41E+04 | 5.98E−04 | 1.75E−08 | 19 |
| bsAb19146D | 190 ± 0.6 | 31 | 6.09E+05 | 2.73E−04 | 4.48E−10 | 42 |
| bsAb19147D | 178 ± 0.3 | 7 | IC# | IC# | IC# | IC# |
| bsAb19148D | 186 ± 0.6 | 6 | IC# | IC# | IC# | IC# |
| bsAb19149D | 178 ± 0.5 | 7 | IC# | IC# | IC# | IC# |
| bsAb19150D | 183 ± 0.8 | 47 | 3.42E+05 | 4.80E−03 | 1.40E−08 | 2.4 |
| bsAb19151D | 168 ± 0.4 | 9 | 2.11E+04 | 2.21E−04 | 1.05E−08 | 52 |
| bsAb19152D | 184 ± 1.1 | 35 | 1.96E+05 | 1.13E−02 | 5.74E−08 | 1.0 |
| bsAb19153D | 179 ± 0.3 | 24 | 2.58E+05 | 4.19E−04 | 1.62E−09 | 28 |
| bsAb19154D | 180 ± 0.5 | 23 | 8.02E+04 | 2.04E−04 | 2.54E−09 | 57 |
| bsAb19155D | 176 ± 0.3 | 7 | IC# | IC# | IC# | IC# |
| bsAb19156D | 182 ± 0.4 | 27 | 8.95E+04 | 2.21E−03 | 2.47E−08 | 5 |
| bsAb19757D | 176 ± 0.4 | 16 | 1.12E+05 | 2.18E−02 | 1.96E−07 | 0.5 |
| bsAb19758D | 177 ± 1.2 | 51 | 3.13E+05 | 4.57E−03 | 1.46E−08 | 2.5 |
| bsAb21236D | 183 ± 0.4 | 12 | 3.03E+04 | 4.26E−03 | 1.40E−07 | 2.7 |
| bsAb21237D | 199 ± 0.5 | 17 | 4.96E+04 | 2.74E−03 | 5.52E−08 | 4 |
| Isotype Control | 175 ± 0.3 | 1 | NB* | NB* | NB* | NB* |

*NB indicates that no binding was observed under the current experimental conditions.

IC indicates that observed binding signal was less than three-fold above to the non-specific binding observed for isotype control antibody surface and/or the data cannot be used to measure binding kinetic parameters.

TABLE 26

Binding kinetics parameters of hGP130-MMH binding to anti-LEPR/GP130 bispecific antibodies at 37° C.

| Bispecific Antibody | mAb Capture Level (RU) | 100 nM hGP130-MMH Bound (RU) | $k_a$ (1/Ms) | $k_d$ (1/s) | $K_D$ (M) | $t^{1/2}$ (min) |
|---|---|---|---|---|---|---|
| bsAb19139D | 209 ± 0.4 | 3 | NB* | NB* | NB* | NB* |
| bsAb19140D | 230 ± 0.5 | 19 | 8.29E+05 | 1.20E−01 | 1.44E−07 | 0.1 |
| bsAb19141D | 229 ± 0.5 | 15 | 1.79E+05 | 6.21E−02 | 3.47E−07 | 0.2 |
| bsAb19142D | 226 ± 0.8 | 37 | 3.56E+05 | 6.22E−03 | 1.75E−08 | 1.9 |
| bsAb19143D | 219 ± 0.5 | 27 | 4.76E+04 | 2.12E−03 | 4.46E−08 | 5 |
| bsAb19144D | 231 ± 1.9 | 42 | 1.77E+05 | 1.88E−03 | 1.06E−08 | 6 |
| bsAb19145D | 223 ± 0.8 | 30 | 6.92E+04 | 2.22E−03 | 3.20E−08 | 5 |
| bsAb19146D | 240 ± 0.6 | 53 | 7.12E+05 | 6.41E−04 | 9.01E−10 | 18 |
| bsAb19147D | 217 ± 0.4 | 5 | IC# | IC# | IC# | IC# |
| bsAb19148D | 231 ± 0.6 | 8 | IC# | IC# | IC# | IC# |
| bsAb19149D | 222 ± 0.6 | 8 | IC# | IC# | IC# | IC# |
| bsAb19150D | 223 ± 1.2 | 52 | 4.33E+05 | 6.65E−03 | 1.54E−08 | 1.7 |
| bsAb19151D | 206 ± 0.4 | 16 | 2.24E+04 | 3.73E−04 | 1.66E−08 | 31 |
| bsAb19152D | 234 ± 0.8 | 28 | 4.07E+05 | 3.63E−02 | 8.91E−08 | 0.3 |
| bsAb19153D | 224 ± 0.3 | 33 | 3.19E+05 | 1.26E−03 | 3.95E−09 | 9 |
| bsAb19154D | 223 ± 0.3 | 37 | 2.69E+05 | 2.61E−04 | 9.73E−10 | 44 |
| bsAb19155D | 214 ± 0.6 | 4 | NB* | NB* | NB* | NB* |
| bsAb19156D | 222 ± 0.7 | 24 | 8.39E+04 | 7.97E−03 | 9.50E−08 | 1.4 |
| bsAb19757D | 216 ± 0.8 | 16 | 1.78E+05 | 6.35E−02 | 3.58E−07 | 0.2 |
| bsAb19758D | 216 ± 1.3 | 50 | 4.48E+05 | 7.47E−03 | 1.67E−08 | 1.5 |
| bsAb21236D | 220 ± 2.1 | 12 | 5.97E+04 | 1.48E−02 | 2.48E−07 | 0.8 |
| bsAb21237D | 263 ± 1 | 19 | 6.11E+04 | 8.79E−03 | 1.44E−07 | 1.3 |
| Isotype Control | 220 ± 0.7 | 4 | NB* | NB* | NB* | NB* |

*NB indicates that no binding was observed under the current experimental conditions.
IC indicates that observed binding signal was less than three-fold above to the non-specific binding observed for isotype control antibody surface and/or the data cannot be used to measure binding kinetic parameters.

At 25° C., 17 out of 22 anti-LEPR/GP130 bispecific antibodies of the invention bound to hGP130-MMH with $K_D$ values ranging from 448 pM to 219 nM, as shown in Table 25. At 37° C., 17 out of 22 anti-LEPR/GP130 bispecific antibodies bound to hGP130-MMH with $K_D$ values ranging from 901 pM to 358 nM, as shown in Table 26.

TABLE 27

Binding kinetics parameters of mfGP130-MMH binding to anti-LEPR/GP130 bispecific antibodies at 25° C.

| Bispecific Antibody | mAb Capture Level (RU) | 100 nM mfGP130-MMH Bound (RU) | $k_a$ (1/Ms) | $k_d$ (1/s) | $K_D$ (M) | $t^{1/2}$ (min) |
|---|---|---|---|---|---|---|
| bsAb19139D | 168 ± 0.3 | 6 | IC# | IC# | IC# | IC# |
| bsAb19140D | 182 ± 0.5 | 20 | 4.02E+05 | 5.46E−02 | 1.36E−07 | 0.2 |
| bsAb19141D | 183 ± 0.6 | 15 | 1.12E+05 | 2.07E−02 | 1.84E−07 | 0.6 |
| bsAb19142D | 183 ± 0.9 | 28 | 1.20E+05 | 3.74E−03 | 3.12E−08 | 3.1 |
| bsAb19143D | 177 ± 0.7 | 10 | 3.01E+04 | 1.30E−03 | 4.30E−08 | 9 |
| bsAb19144D | 183 ± 1.3 | 27 | 5.67E+04 | 7.62E−04 | 1.34E−08 | 15 |
| bsAb19145D | 175 ± 0.3 | 18 | 3.31E+04 | 5.76E−04 | 1.74E−08 | 20 |
| bsAb19146D | 190 ± 0.4 | 31 | 5.02E+05 | 2.58E−04 | 5.13E−10 | 45 |
| bsAb19147D | 177 ± 0.3 | 5 | IC# | IC# | IC# | IC# |
| bsAb19148D | 186 ± 0.6 | 6 | IC# | IC# | IC# | IC# |
| bsAb19149D | 178 ± 0.8 | 6 | IC# | IC# | IC# | IC# |
| bsAb19150D | 183 ± 1 | 44 | 3.08E+05 | 5.19E−03 | 1.68E−08 | 2.2 |
| bsAb19151D | 168 ± 0.5 | 3 | NB* | NB* | NB* | NB* |
| bsAb19152D | 184 ± 0.7 | 52 | 2.95E+05 | 5.53E−03 | 1.88E−08 | 2.1 |
| bsAb19153D | 178 ± 0.4 | 23 | 2.29E+05 | 3.96E−04 | 1.73E−09 | 29 |
| bsAb19154D | 180 ± 0.5 | 22 | 7.23E+04 | 2.02E−04 | 2.79E−09 | 57 |
| bsAb19155D | 175 ± 0.3 | 7 | 9.85E+04 | 1.84E−02 | 1.86E−07 | 0.6 |
| bsAb19156D | 182 ± 0.4 | 30 | 7.33E+04 | 1.62E−03 | 2.21E−08 | 7 |
| bsAb19757D | 175 ± 0.5 | 15 | 1.08E+05 | 2.04E−02 | 1.88E−07 | 0.6 |
| bsAb19758D | 176 ± 1.7 | 46 | 3.07E+05 | 5.07E−03 | 1.65E−08 | 2.3 |

TABLE 27-continued

Binding kinetics parameters of mfGP130-MMH binding to anti-LEPR/GP130 bispecific antibodies at 25° C.

| Bispecific Antibody | mAb Capture Level (RU) | 100 nM mfGP130-MMH Bound (RU) | $k_a$ (1/Ms) | $k_d$ (1/s) | $K_D$ (M) | t½ (min) |
|---|---|---|---|---|---|---|
| bsAb21236D | 240 ± 0.6 | 21 | 2.94E+04 | 3.05E−03 | 1.04E−07 | 3.8 |
| bsAb21237D | 212 ± 0.6 | 18 | 3.98E+04 | 2.13E−03 | 5.34E−08 | 5 |
| Isotype Control | 175 ± 0.5 | 1 | NB* | NB* | NB* | NB* |

*NB indicates that no binding was observed under the current experimental conditions.
IC indicates that observed binding signal was less than three-fold above to the non-specific binding observed for isotype control antibody surface and/or the data cannot be used to measure binding kinetic parameters.

TABLE 28

Binding kinetics parameters of mfGP130-MMH binding to anti-LEPR/GP130 bispecific antibodies at 37° C.

| Bispecific Antibody | mAb Capture Level (RU) | 100 nM mfGP130-MMH Bound (RU) | $k_a$ (1/Ms) | $k_d$ (1/s) | $K_D$ (M) | t½ (min) |
|---|---|---|---|---|---|---|
| bsAb19139D | 208 ± 0.4 | 2 | NB* | NB* | NB* | NB* |
| bsAb19140D | 229 ± 0.5 | 14 | 7.97E+05 | 1.46E−01 | 1.83E−07 | 0.1 |
| bsAb19141D | 228 ± 0.5 | 15 | 2.42E+05 | 5.13E−02 | 2.12E−07 | 0.2 |
| bsAb19142D | 226 ± 1.4 | 33 | 3.32E+05 | 7.15E−03 | 2.16E−08 | 1.6 |
| bsAb19143D | 217 ± 1.1 | 14 | 6.83E+04 | 3.96E−03 | 5.79E−08 | 2.9 |
| bsAb19144D | 230 ± 1.3 | 41 | 1.68E+05 | 1.83E−03 | 1.09E−08 | 6 |
| bsAb19145D | 222 ± 0.5 | 29 | 5.88E+04 | 2.21E−03 | 3.76E−08 | 5 |
| bsAb19146D | 239 ± 0.5 | 53 | 6.53E+05 | 6.26E−04 | 9.59E−10 | 18 |
| bsAb19147D | 216 ± 0.4 | 3 | NB* | NB* | NB* | NB* |
| bsAb19148D | 231 ± 0.5 | 8 | IC# | IC# | IC# | IC# |
| bsAb19149D | 221 ± 0.8 | 8 | IC# | IC# | IC# | IC# |
| bsAb19150D | 222 ± 1.3 | 46 | 4.01E+05 | 7.73E−03 | 1.93E−08 | 1.5 |
| bsAb19151D | 209 ± 7.1 | 6 | NB* | NB* | NB* | NB* |
| bsAb19152D | 233 ± 1 | 51 | 3.42E+05 | 1.77E−02 | 5.16E−08 | 0.7 |
| bsAb19153D | 223 ± 0.3 | 32 | 2.84E+05 | 1.23E−03 | 4.33E−09 | 9 |
| bsAb19154D | 223 ± 0.4 | 35 | 2.19E+05 | 3.43E−04 | 1.57E−09 | 34 |
| bsAb19155D | 213 ± 0.4 | 3 | NB* | NB* | NB* | NB* |
| bsAb19156D | 221 ± 0.6 | 26 | 8.75E+04 | 7.67E−03 | 8.76E−08 | 1.5 |
| bsAb19757D | 215 ± 0.9 | 14 | 1.33E+05 | 5.98E−02 | 4.50E−07 | 0.2 |
| bsAb19758D | 215 ± 1 | 45 | 4.02E+05 | 7.30E−03 | 1.82E−08 | 1.6 |
| bsAb21236D | 285 ± 2.1 | 18 | 6.98E+04 | 1.25E−02 | 1.79E−07 | 0.9 |
| bsAb21237D | 270 ± 1 | 21 | 3.69E+04 | 7.92E−03 | 2.15E−07 | 1.5 |
| Isotype Control | 219 ± 0.5 | 4 | NB* | NB* | NB* | NB* |

*NB indicates that no binding was observed under the current experimental conditions.
IC indicates that observed binding signal was less than three-fold above to the non-specific binding observed for isotype control antibody surface and/or the data cannot be used to measure binding kinetic parameters.

At 25° C., 17 out of 22 LEPR×GP130 bispecific antibodies of the invention bound to mfGP130-MMH with $K_D$ values ranging from 513 pnM to 188 nM, as shown in Table 27. At 37° C., 16 out of 22 LEPR×GP130 bispecific antibodies of the invention bound to mfGP130-MMH with $K_D$ values ranging from 959 pM to 450 nM, as shown in Table 28.

Example 11: LEPR×GP130 Bispecific Antibody Cell Binding Measured by FACS Analysis In order to assess cell binding by LEPR×GP130 bispecific antibodies, HEK293 stable cell lines were generated. One cell line was generated to stably over-express full length human GP130 (amino acids 1-918 of accession #P40189 with leucine at position 2 changed to valine, a natural variant) along with a luciferase reporter (Stat3-luciferase, Stat3-luc, SA Bioscience, #CLS-6028L), and was sorted twice using flow cytometry for high expression of GP130. This cell line is referred to hereafter as "HEK293/Stat3-luc/gp130-2× Sort." Another cell line used in this Example, known hereafter as "HEK293/hLEPR-GPI," stably expresses the extracellular domain of human LEPR (amino acids 22-839 of accession #P48357, Isoform B) with an N-terminal myc-myc tag and C-terminal peptide sequence from human carboxypeptidase M that guides the addition of GPI (Glycosylphosphatidylinositol) such that the protein can be GPI-anchored to the membrane.

For the FACS analysis, 0.5×106 cells/well of HEK293 parental cells, HEK293/Stat3-luc/gp130-2× Sort cells, and HEK293/hLEPR-GPI cells, were incubated with 200 nM of the conventional antibodies against either GP130 or LEPR or with LEPR×GP130 bispecific antibodies, along with isotype control antibodies at 4° C. in PBS (without calcium and magnesium) containing 2% FBS.

To test whether the anti-LEPR antibody binding or LEPR×GP130 bispecific antibody binding to cells was affected by the presence of Leptin, 1 pM human Leptin (R&D Systems, #398-LP) was incubated with the cells for 30 minutes, followed by the addition of anti-LEPR antibodies or isotype control antibody. After incubation with primary antibodies, the cells were stained with 8 mg/mL of Alexa Fluor®-647 conjugated secondary antibody (Jackson ImmunoResearch Laboratories Inc., #109-607-003) for 30 minutes. Cells were fixed using BD CytoFix™ (Becton Dickinson, #554655) and analyzed on an IQue® (Intellicyt) Flow Cytometer. Unstained and secondary antibody alone controls were also tested for all cell lines. The results were analyzed using ForeCyt® (IntelliCyt) and FlowJo version 10 softwares to determine the geometric means of fluorescence for viable cells.

As shown in Table 29, two LEPR×GP130 bispecific antibodies of the invention tested at 200 nM demonstrated binding to HEK293/gp130 2× Sort cells with binding ratios of 132- and 169-fold and binding to HEK293/hLEPR-GPI cells with binding ratios of 4423- and 6320-fold without Leptin, and 3596- and 5932-fold in the presence of 1 pM Leptin. The GP130-binding arm of the bispecific antibodies of the invention made as a conventional antibody (mAb16683) demonstrated binding to HEK293/gp130 2× Sort cells with a binding ratio of 235-fold and binding to HEK293/hLEPR-GPI cells with a binding ratio of 21-fold. The LEPR binding arms of the bispecifics (mAb18445 and mAb18446) made as a conventional antibody demonstrated binding to HEK293/hLEPR-GPI cells with binding ratios of 4711- and 7023-fold without Leptin, and 4246- and 6390-fold in the presence of 1 pM Leptin. The anti-GP130 and anti-LEPR conventional and bispecific antibodies demonstrated binding to the HEK293 parental cells with binding ratios ranging from 3- to 24-fold. The isotype control antibodies and secondary antibodies alone samples also did not demonstrate significant binding to any of the cell lines tested with or without Leptin, with binding ratios ranging from 1- to 3-fold.

Example 12: Functional Cell-Based Assays

The cytokine receptors GP130 (amino acids 1-918 of accession #P40189) and LEPR (amino acids 1-1165 of accession #P48357) have a non-covalently associated tyrosine kinase, JAK2, bound to the membrane proximal region of their cytoplasmic domains. Treatment with cognate ligand or agonist antibody culminates in activation of JAK2, which in turn phosphorylates key tyrosine residues on the cytoplasmic region of the receptor. The phosphorylated tyrosine residues serve as docking sites for signaling complexes that upon phosphorylation lead to stimulation of signaling pathways such as STAT3 and ERK. For the LEPR, tyrosine residue Y1141 mediates STAT3 signaling and mutation of this residue to phenylalanine (Y1141F) eliminates STAT3 signaling (Carpenter et al., 1998, Proc. Natl. Acad. Sci. USA 95:6061-6066).

A bioassay was developed to detect the transcriptional activation of STAT3 via the promotion of GP130 and LEPR heterodimerization following treatment with LEPR×GP130 bsAbs. In particular, a reporter cell line that stably expresses mutant human LEPR (Y1141F) and wild-type human GP130, along with a STAT3 responsive luciferase reporter (STAT3-Luc; Qiagen CLS-6028L) was generated. The resulting stable cell line, referred to as HEK293.STAT3.Luc.GP130.hLEPR (Y1141F), was isolated and maintained in DME medium supplemented with 10% FBS, 1 ug/mL Puromycin, 250 ug/mL of Hygromycin B, 500 ug/mL of G418 and Penicillin/Streptomycin/L-Glutamine. Two LEPR×GP130 bispecific antibodies were identified in this bioassay, bsAb21236 and bsAb21237, which promoted STAT3 activity in the presence of leptin.

For the bioassay, HEK293.STAT3.Luc.GP130.hLEPR (Y1141F) cells were plated at a density of 20,000 cells/well and then the following day the media was replaced with 80 uL of Opti-MEM supplemented with 1% BSA and 0.1% FBS (Assay Buffer). Subsequently, 10 uL of fixed-concentration of 10 nM of human Leptin (hLeptin; R&D Systems, #398-LP-01M) was added to the wells. Immediately following the hLeptin treatment, the bispecific antibodies were half-log serially diluted (12 points) to final concentrations ranging from 500 nM to 5 pM in Assay Buffer and were then

TABLE 29

Antibody Binding to Cells Assessed by FACS

| | Binding Ratio: Normalized to Unstained Sample of Each Cell Line (FL4-A) | | | |
|---|---|---|---|---|
| Antibody | HEK293 parental | HEK293/ gp130 2X Sort | HEK293/hLEPR-GPI cells (No Leptin) | HEK293/hLEPR-GPI cells (1 μM Leptin) |
| bsAb21236 (LEPR × GP130) | 13 | 132 | 4423 | 3596 |
| bsAb21237 (LEPR × GP130) | 24 | 169 | 6320 | 5932 |
| mAb16683 (anti-GP130 mAb) | 17 | 235 | 21 | Not Tested |
| mAB18445 (anti-LEPR mAb) | 3 | Not Tested | 4711 | 4246 |
| mAB18446 (anti-LEPR mAb) | 6 | Not Tested | 7023 | 6390 |
| Isotype control antibody | 2 | 2 | 3 | 3 |
| Secondary antibody alone | 1 | 1 | 3 | 2 |
| No Antibody | 1 | 1 | 1 | Not Tested | added to the cells. The isotype control and human OSM (hOSM; R&D Systems, #295-OM/CF) were half-log diluted (11 points) to final concentrations ranging from 100 nM to 1 pM in Assay Buffer and were then added to the cells. The plates were then placed in the incubator overnight at 37° C. in 5% $CO_2$. One-Glo reagent (Promega, #E6051) was then added to the samples and luciferase activity was measured on Envision Multilable Plate Reader (Perkin Elmer) in Luminescent mode. The relative light units (RLU) values were obtained and the results were analyzed using nonlinear regression with GraphPad Prism software (Graph Pad). The maximum RLU value obtained from the hOSM dose response was defined as 100% activation in the HEK293.STAT3.Luc.GP130.hLepR (Y1141F) cell-based assay.

The ability of LEPR×GP130 bispecific antibodies to activate via GP130-mediated cell signaling was evaluated in the HEK293.STAT3.Luc.gp130.hLepR (Y1141F) cell-based assay and the resulting $EC_{50}$ values and percentage activation are shown in Table 30. The responsiveness of the cell line was confirmed using a dose response of hOSM, which demonstrated activation in the assay with an $EC_{50}$ value of 592 pM. Both LEPR×GP130 bispecific antibodies tested, bsAb21236 and bsAb21237, demonstrated activation in this assay with $EC_{50}$ values of 2.11 nM and 2.46 nM, respectively. Both bispecific antibodies have approximately 20% of maximal activation observed with hOSM.

TABLE 30

Activation of HEK293.STAT3.Luc.GP130.hLEPR (Y1141F) Cell line by LEPR × GP130 Bispecific Antibodies

| Molecule tested | $EC_{50}$ (M) | Percentage activation as compared to hOSM |
|---|---|---|
| bsAb21236 | 2.109E−09 | 25% |
| bsAb21237 | 2.460E−09 | 20% |
| hOSM | 5.919E−10 | 100% |
| Isotype control antibody | No activation | No activation |

To confirm that the activation by LEPR×GP130 bispecific antibodies in the HEK293.STAT3.Luc.GP130.hLEPR (Y1141F) cell-based assay was due to activation through both LEPR and GP130, a competition bioassay was performed using soluble LEPR and GP130 proteins to block the activation by the bispecific antibodies. The competition bioassay utilized an excess fixed concentration, 500 nM, of the extracellular domain of human LEPR with a C-terminal hFc tag (hLEPR-hFc; SEQ ID NO:189), the extracellular domain of human LEPR with a C-terminal myc-myc-hexahistidine tag (hLEPR-MMH; SEQ ID NO:187), the extracellular domain of human GP130 with a C-terminal hFc tag (hGP130-hFc; SEQ ID NO:197), and the extracellular domain of human CNTFR with a C-terminal myc-myc-hexahistidine tag (hCNTFR-MMH; SEQ ID NO:198).

For the assay, HEK293.STAT3.Luc.GP130.hLEPR (Y1141F) cells were plated at the density of 20,000 cells/well and then the following day the media was replaced with 70 uL of Opti-MEM supplemented with 1% BSA and 0.1% FBS (Assay Buffer). 10 uL of fixed-concentration of 10 nM of human Leptin (hLeptin; R&D Systems, #398-LP-01M) was added to the wells. Immediately following the hLeptin treatment, 10 nM of the bispecific antibodies in Assay Buffer were then added to the cells. Immediately after, an excess amount, 500 nM, of the soluble proteins hLEPR-hFc, hLEPR-MMH, hGP130-hFc, and hCNTFR-MMH were added to the appropriate designated wells. The plates were then placed in the incubator overnight at 37° C. in 5% CO2. One-Glo reagent (Promega, #E6051) was then added to the samples and luciferase activity was measured on Envision Multilable Plate Reader (Perkin Elmer) in Luminescent mode. The relative light units (RLU) values were obtained and the results were analyzed using GraphPad Prism software (GraphPad).

The competition assay result demonstrated that soluble hLEPR-hFc, hLEPR-MMH and hGP130-hFc were able to block the bispecific antibody activity whereas soluble hCNTFR.mmh did not block the activity of the bispecific antibodies. The activity of the bispecific antibodies alone is defined as 100% whereas the activity of isotype control represents 0% activity.

Table 31, below shows activation of HEK293.STAT3.Luc.GP130.hLEPR cells by bispecific antibodies in the presence of soluble human LEPR, GP130 and CNTFR. Table 32 shows RLU production in the presence of hLEPR-MMH, hLEPR-hFc, hGP130-hFc or hCNTFR-MMH.

TABLE 31

Activation of HEK293.STAT3.Luc.GP130.hLEPR (Y1141F) cells by LEPR × GP130 bispecific antibodies in the presence of soluble human LEPR, GP130, and CNTFR

| Bispecific Antibody | RLU in the presence of hLEPR-MMH [500 nM] | | RLU in the presence of hLEPR-hFc [500 nM] | | RLU in the presence of hGP130-hFc [500 nM] | | RLU in the presence of hCNTFR-MMH [500 nM] | | Assay Buffer | |
|---|---|---|---|---|---|---|---|---|---|---|
| bsAb21236 | 12840 | 13160 | 11640 | 10320 | 15520 | 13840 | 48560 | 43080 | 48920 | 42160 |
| bsAb21237 | 11280 | 11800 | 10480 | 9480 | 14320 | 15680 | 39920 | 43400 | 44920 | 38080 |
| Isotype control | | | | | | | | | 12160 | 12080 |

TABLE 32

Activation of HEK293.STAT3.Luc.GP130.hLEPR (Y1141F) cells by LEPR × GP130 bispecific antibodies in the presence of soluble human LEPR, GP130, and CNTFR

| Bispecific Antibody | RLU in the presence of hLEPR-MMH [500 nM] | RLU in the presence of hLEPR-hFc [500 nM] | RLU in the presence of hGP130-hFc [500 nM] | RLU in the presence of hCNTFR-MMH [500 nM] | Assay Buffer |
|---|---|---|---|---|---|
| bsAb21236 | 3% | −3% | 8% | 101% | 100% |
| bsAb21237 | −2% | −7% | 10% | 101% | 100% |
| Isotype control | | | | | 0% |

Example 13: In Vivo Efficacy of LEPR×GP130 Bispecific Antibodies bsAb21236 and bsAb21237 in Diet-Induced Obese Mice The effects of two LEPR×GP130 bispecific antibodies of the invention, bsAb21236 and bsAb21237, on body weight were determined in an in vivo model using high fat diet fed obese LEPRHu/Hu;IL6STHu/Hu mice, that express a leptin receptor composed of the human LEPR extracellular domain sequence in place of the murine LEPR extracellular domain sequence and a GP130 protein composed of the human IL6ST extracellular domain sequence in place of the murine IL6ST extracellular domain sequence.

On day 0, twenty-three male LEPRHu/Hu;IL6STHu/Hu mice that were fed a high fat diet for 12 weeks were randomized into three groups of 7 to 8 mice based on body weight. On day 0 and 7, each group received via subcutaneous injection a dose of either isotype control antibody at 30 mg/kg, bsAb21236 at 30 mg/kg, or bsAb21237 at 30 mg/kg. The isotype control antibody used does not bind any known mouse protein. The body weight of each mouse was measured daily for the duration of the study. The percent change in body weight from day 0 was calculated for each animal at every time point measured. FIG. 1 summarizes the average percent change in body weight for animals in each treatment group. All results are expressed as mean±SEM.

As shown in FIG. 1, LEPRHu/Hu;IL6STHu/Hu mice treated with bsAb21236 at 30 mg/kg exhibited significant reductions in percent body weight change starting at three days post antibody treatment and at the other subsequent time points measured compared to mice injected with isotype control antibody. LEPRHu/Hu;IL6STHu/Hu mice treated with bsAb21237 at 30 mg/kg exhibited a significant reduction in percent body weight change starting at five days post antibody treatment and at the other subsequent time points measured compared to mice injected with isotype control antibody.

Example 14: Transcriptional Activation of STAT3 Via the Promotion of GP130 and LEPR (Short Form) Heterodimerization Following Treatment with LEPR×GP130 bsAbs GP130 serves a co-receptor for multiple cytokines and is expressed broadly in human tissues (Taga T., Kishimoto T. gp130 and the interleukin-6 family of cytokines. Annu. Rev. Immunol 1997; 15:797-819). Isoforms of the LEPR are generated through alternative splicing, resulting a long isoform b (LEPR-b) and several short forms, including isoform a (LEPR-a) which shows the highest and broadest expression pattern (Tartaglia L A. The leptin receptor. J Biol Chem 1997; 272: 6093-6096). All the isoforms share the same extracellular domain, transmembrane region and a short stretch of the cytoplasmic domain, containing the Box 1 region, followed by a variable region. The long form contains intracellular sequence motifs required for mediating all the signaling capabilities of leptin whereas the short forms are lacking these regions. Since the extracellular domain of the short forms is identical to the signaling competent long form, the bispecific antibodies can bind to the short forms and generate complexes with GP130. The primary intended target tissue for LEPR agonists in general (including LEPR× GP130 bispecific antigen binding molecules) is the brain where LEPR isoform b is predominantly expressed. Given the broad expression of GP130 and isoform a of LEPR, however, there existed the potential for unwanted STAT3 activation in tissues such as the liver.

In order to evaluate signaling outcomes resulting from complexing of LEPR short isoform a and GP130, a bioassay was developed to detect the transcriptional activation of STAT3 via the promotion of GP130 and LEPR (short form) heterodimerization following treatment with LEPR×GP130 bsAbs. In particular, a reporter cell line that stably expresses the dominant short form of LEPR (NP_001003679.1), to be referred to as hLEPR(a), and wild-type human GP130, along with a STAT3 responsive luciferase reporter (STAT3-Luc; Qiagen CLS-6028L) was generated. The resulting stable cell line, referred to as HEK293.STAT3.Luc.GP130.hLEPR(a), was isolated and maintained in DME medium supplemented with 10% FBS, 1 ug/mL Puromycin, 250 ug/mL of Hygromycin B, 500 ug/mL of G418 and Penicillin/Streptomycin/ L-Glutamine.

For the bioassay, HEK293.STAT3.Luc.GP130.hLEPR (a) cells were plated at a density of 20,000 cells/well and then the following day the media was replaced with 80 uL of Opti-MEM supplemented with 1% BSA and 0.1% FBS (Assay Buffer). Subsequently, 10 uL of fixed-concentration of 10 nM of human Leptin (hLeptin; R&D Systems, #398-LP-01 M) was added to the wells. Immediately following the hLeptin treatment, the bispecific antibodies were half-log serially diluted (12 points) to final concentrations ranging from 500 nM to 5 pM in Assay Buffer and were then added to the cells. As controls, human leptin and OSM (hOSM; R&D Systems, #295-OM/CF) were half-log diluted (11 points) to final concentrations ranging from 100 nM to 1 pM in Assay Buffer and were then added to the cells. The plates were then placed in the incubator overnight at 37° C. in 5% $CO_2$. One-Glo reagent (Promega, #E6051) was then added to the samples and luciferase activity was measured on Envision Multilable Plate Reader (Perkin Elmer) in Luminescent mode. The relative light units (RLU) values were obtained and the results were analyzed using nonlinear regression with GraphPad Prism software (GraphPad). The maximum RLU value obtained from the hOSM dose response was defined as 100% activation in the HEK293.STAT3.Luc.GP130.hLEPR (a) cell-based assay.

The ability of LEPR×GP130 bispecific antibodies to activate via GP130-mediated cell signaling was evaluated in the HEK293.STAT3.Luc.gp130.hLEPR (a) cell-based assay and the resulting responses are shown in Table 33. The responsiveness of the cell line was confirmed using a dose response of hOSM, which demonstrated activation in the assay with an $EC_{50}$ value of 121 pM and its maximum response was designated as 100% activation. Both LEPR×GP130 bispecific antibodies tested, bsAb21236 and bsAb21237, failed to activate STAT3 signaling with LEPR (a). Similar to leptin, the bispecific antigen-binding proteins of the present invention generate productive STAT3 signaling only in cell types containing the long form of LEPR.

TABLE 33

Activation of HEK293.STAT3.Luc.GP130.hLEPR (a) Cell line by LEPR × GP130 Bispecific Antibodies

| Molecule tested | $EC_{50}$ (M) | Percentage maximum activation as compared to hOSM |
|---|---|---|
| bsAb21236 + 10 nM leptin | No activation | No activation |
| bsAb21237 + 10 nM leptin | No activation | No activation |
| hOSM | 1.21E−10 | 100% |
| hLeptin | No activation | No activation |

In summary, the data shows that the LEPR×GP130 bispecific antibodies provided herein do not activate signaling through the "short form" of the leptin receptor (LEPR-a isoform), but do activate signaling through the "long form" of the leptin receptor (LEPR-b isoform). The relevance of this finding is that it suggests that these bispecific antibodies will exert their activity primarily in the brain where the 'b' isoform is predominantly expressed, but not in other tissues such as the liver where the 'a' form is broadly expressed. Given that these bispecific antibodies can be used to treat obesity by activating LEPR signaling in the brain, this work confirms that the bispecific antibodies provided herein are effective at targeting leptin signaling where it is needed (in the brain) while avoiding unwanted signaling elsewhere in the body (such as the liver, e.g. in inflammatory hepatocellular adenoma (see Rebouissou et al., Nature Letters, 457(8): 200-205, 2009)).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What it claimed is:

1. A bispecific antibody or antigen-binding fragment thereof, comprising:
   (a) a first immunoglobulin heavy chain variable region (HCVR) and a first immunoglobulin light chain variable region (LCVR) that binds human GP130 wherein the HCVR comprises three heavy chain complementarity determining regions (HCDR1, HCDR2 and HCDR3) from a HCVR comprising the amino acid sequence of SEQ ID NO: 154 and the LCVR comprises three light chain complementarity determining regions (LCDR1, LCDR2 and LCDR3) from a LCVR comprising the amino acid sequence of SEQ ID NO: 10; and
   (b) a second HCVR and second LCVR that binds human leptin receptor (LEPR).

2. The bispecific antibody or antigen-binding fragment of claim 1, wherein said
   HCDR1 comprises the amino acid sequence of SEQ ID NO: 156;
   HCDR2 comprises the amino acid sequence of SEQ ID NO: 158;
   HCDR3 comprises the amino acid sequence of SEQ ID NO: 160;
   LCDR1 comprises the amino acid sequence of SEQ ID NO: 12;
   LCDR2 comprises the amino acid sequence of SEQ ID NO: 14; and
   LCDR3 comprises the amino acid sequence of SEQ ID NO: 16.

3. The bispecific antibody or antigen-binding fragment of claim 2, wherein said first HCVR comprises the amino acid sequence of SEQ ID NO: 154; and said first LCVR comprises the amino acid sequence of SEQ ID NO:10.

4. The bispecific antibody or antigen-binding fragment of claim 1, wherein
   the second HCVR comprises
   three heavy chain complementarity determining regions (HCDR1, HCDR2 and HCDR3) from a HCVR comprising the amino acid sequence selected from the group consisting of SEQ ID NOs: 2, 162, 170 and 178; and
   the second LCVR comprises
   three light chain complementarity determining regions (LCDR1, LCDR2 and LCDR3) from a LCVR comprising the amino acid sequence of SEQ ID NO: 10.

5. The bispecific antibody or antigen-binding fragment of claim 4, wherein said second HCVR comprises an HCDR1, HCDR2, HCDR3 comprising amino acid sequences selected from the group consisting of
   SEQ ID NOs: 4, 6, 8, respectively,
   SEQ ID NOs: 164, 166, 168, respectively,
   SEQ ID NOs: 172, 174, 176, respectively, and
   SEQ ID NOs: 180, 182, 184, respectively; and
   wherein said second LCVR comprises an LCDR1, LCDR2, LCDR3 comprising amino acid sequences of SEQ ID NOs: 12, 14, 16, respectively.

6. The bispecific antibody or antigen-binding fragment of claim 5, wherein said second HCVR comprises an amino acid sequence selected from the group consisting of SEQ ID NOs: 2, 162, 170 and 178; and said second LCVR comprises the amino acid sequence of SEQ ID NO: 10.

7. A pharmaceutical composition comprising the bispecific antibody or antigen-binding fragment of claim 1, and a pharmaceutically acceptable carrier or diluent.

8. A vessel or injection device comprising the bispecific antibody or antigen-binding fragment of claim 1 or a pharmaceutical composition thereof.

9. A bispecific antibody or antigen-binding fragment thereof which is a product of a method comprising:
   introducing one or more polynucleotides encoding:
      (a) a first immunoglobulin heavy chain variable region (HCVR) and a first immunoglobulin light chain variable region (LCVR) that binds human GP130, wherein said first HCVR comprises three heavy chain complementarity determining regions (HCDR1, HCDR2 and HCDR3) from a HCVR comprising the amino acid sequence of SEQ ID NO: 154 and said first LCVR comprises three light chain complementarity determining regions (LCDR1, LCDR2 and LCDR3) from a LCVR comprising the amino acid sequence of SEQ ID NO: 10; and
      (b) a second HCVR and a second LCVR that binds human leptin receptor (LEPR);
   into a host cell;
   culturing the host cell under conditions favorable to expression of the polynucleotide(s); and
   optionally, isolating the antibody or antigen-binding fragment from the host cell and/or medium in which the host cell was grown.

\* \* \* \* \*